US010066027B2

(12) United States Patent
Wood et al.

(10) Patent No.: US 10,066,027 B2
(45) Date of Patent: Sep. 4, 2018

(54) PROTEIN PRODUCTION SYSTEMS AND METHODS THEREOF

(71) Applicant: Ohio State Innovation Foundation, Columbus, OH (US)

(72) Inventors: David Webster Wood, Dublin, OH (US); Changhua Shi, Tempe, AZ (US)

(73) Assignee: Ohio State Innovation Foundation, Columbus, OH (US)

( * ) Notice: Subject to any disclaimer, the term of this patent is extended or adjusted under 35 U.S.C. 154(b) by 136 days.

(21) Appl. No.: 14/992,491

(22) Filed: Jan. 11, 2016

(65) Prior Publication Data

US 2016/0207965 A1 Jul. 21, 2016

Related U.S. Application Data

(60) Provisional application No. 62/101,518, filed on Jan. 9, 2015.

(51) Int. Cl.

| | |
|---|---|
| C07K 17/00 | (2006.01) |
| C07K 17/08 | (2006.01) |
| C12N 9/16 | (2006.01) |
| C07K 14/535 | (2006.01) |
| C07K 1/22 | (2006.01) |
| C07K 14/315 | (2006.01) |

(52) U.S. Cl.
CPC ............ C07K 17/08 (2013.01); C07K 1/22 (2013.01); C07K 14/3153 (2013.01); C07K 14/535 (2013.01); C12N 9/16 (2013.01); C12Y 304/24029 (2013.01); C07K 2319/00 (2013.01); C07K 2319/21 (2013.01); C12Y 301/03001 (2013.01)

(58) Field of Classification Search
None
See application file for complete search history.

(56) References Cited

U.S. PATENT DOCUMENTS

2015/0353597 A1\* 12/2015 Chen ..................... C07K 1/22
435/196

OTHER PUBLICATIONS

Derbyshire, V., Wood, D. W., Wu, W., Dansereau, J. T., Dalgaard, J. Z., & Belfort, M. (1997). Genetic definition of a protein-splicing domain: functional mini-inteins support structure predictions and a model for intein evolution. Proceedings of the National Academy of Sciences, 94(21), 11466-11471.
Dhar, T., & Mootz, H. D. (2011). Modification of transmembrane and GPI-anchored proteins on living cells by efficient protein trans-splicing using the Npu DnaE intein. Chemical Communications, 47(11), 3063-3065.
Ding, Y., Xu, M. Q., Ghosh, I., Chen, X., Ferrandon, S., Lesage, G., & Rao, Z. (2003). Crystal structure of a mini-intein reveals a conserved catalytic module involved in side chain cyclization of asparagine during protein splicing. Journal of Biological Chemistry, 278(40), 39133-39142.
Duan, X., Gimble, F. S., & Quiocho, F. A. (1997). Crystal structure of PI-SceI, a homing endonuclease with protein splicing activity. Cell, 89(4), 555-564.
Evans, T. C., Martin, D., Kolly, R., Panne, D., Sun, L., Ghosh, I., . . . & Xu, M. Q. (2000). Protein trans-Splicing and Cyclization by a Naturally Split Intein from the dnaE Gene ofSynechocystis Species PCC6803. Journal of Biological Chemistry, 275(13), 9091-9094.
Guan D, Ramirez M, Chen Z (2013) Split intein mediated ultra-rapid purification of tagless protein (SIRP). Biotechnol Bioeng 110: 2471-2481.
Ichiyanagi, K., Ishino, Y., Ariyoshi, M., Komori, K., & Morikawa, K. (2000). Crystal structure of an archaeal intein-encoded homing endonuclease PI-PfuI. Journal of molecular biology, 300(4), 889-901.
Klabunde, T., Sharma, S., Telenti, A., Jacobs, W. R., & Sacchettini, J. C. (1998). Crystal structure of GyrA intein from *Mycobacterium xenopi* reveals structural basis of protein splicing. Nature Structural & Molecular Biology, 5(1), 31-36.
Kwon, Y., Coleman, M. A., & Camarero, J. A. (2006). Selective Immobilization of Proteins onto Solid Supports through Split-Intein-Mediated Protein Trans-Splicing. Angewandte Chemie International Edition, 45(11), 1726-1729.
Iwai, H., Züger, S., Jin, J., & Tam, P. H. (2006). Highly efficient protein trans-splicing by a naturally split DnaE intein from Nostoc punctiforme. FEBS letters, 580(7), 1853-1858.
Liu, X. Q., & Yang, J. (2003). Split dnaE genes encoding multiple novel inteins in Trichodesmium erythraeum. Journal of Biological Chemistry, 278(29), 26315-26318.
Perler, F. B. et al. (1994). Protein splicing elements: inteins and exteins—a definition of terms and recommended nomenclature. Nucleic acids research, 22(7), 1125.-1127.
Perler, F. B. (2002). InBase: the intein database. Nucleic acids research, 30(1), 383-384.
Ramirez, M., Valdes, N., Guan, D., & Chen, Z. (2013). Engineering split intein DnaE from Nostoc punctiforme for rapid protein purification. Protein Engineering Design and Selection, 26(3), 215-223.
Saleh, L., & Perler, F. B. (2006). Protein splicing in cis and in trans. The Chemical Record, 6(4), 183-193.
Scott, C. P., Abel-Santos, E., Wall, M., Wahnon, D. C., & Benkovic, S. J. (1999). Production of cyclic peptides and proteins in vivo. Proceedings of the National Academy of Sciences, 96(24), 13638-13643.
Shi, C., Tarimala, A., Meng, Q., & Wood, D. W. (2014). A general purification platform for toxic proteins based on intein trans-splicing. Applied microbiology and biotechnology, 98(22), 9425-9435.
Telenti, A., Southworth, M., Alcaide, F., Daugelat, S., Jacobs, W. R., & Perler, F. B. (1997). The *Mycobacterium xenopi* GyrA protein splicing element: characterization of a minimal intein. Journal of bacteriology, 179(20), 6378-6382.

(Continued)

*Primary Examiner* — Anand U Desai
(74) *Attorney, Agent, or Firm* — Meunier Carlin & Curfman LLC

(57) ABSTRACT

Disclosed herein is a protein purification system and methods of using the system. In particular, disclosed is a split intein comprising an N-terminal intein segment, which can be immobilized, and a C-terminal intein segment, which has the property of being self-cleaving, and which can be attached to a protein of interest. Through the self-cleaving mechanism of the intein, the protein of interest can be purified.

19 Claims, 26 Drawing Sheets

Specification includes a Sequence Listing.

(56) References Cited

OTHER PUBLICATIONS

Vila-Perelló, M., Liu, Z., Shah, N. H., Willis, J. A., Idoyaga, J., & Muir, T. W. (2012). Streamlined expressed protein ligation using split inteins. Journal of the American Chemical Society, 135(1), 286-292.

Wood, D. W., Wu, W., Belfort, G., Derbyshire, V., & Belfort, M. (1999). A genetic system yields self-cleaving inteins for bioseparations. Nature biotechnology, 17(9), 889-892.

Wu, H., Xu, M. Q., & Liu, X. Q. (1998). Protein trans-splicing and functional mini-inteins of a cyanobacterial dnaB intein. Biochimica et Biophysica Acta (BBA)—Protein Structure and Molecular Enzymology, 1387(1), 422-432.

Xu, M. Q., & Perler, F. B. (1996). The mechanism of protein splicing and its modulation by mutation. The EMBO journal, 15(19), 5146-5153.

Xu, M. Q., & Evans, T. C. (2001). Intein-mediated ligation and cyclization of expressed proteins. Methods, 24(3), 257-277.

Yang, J., Meng, Q., & Liu, X. Q. (2004). Intein harbouring large tandem repeats in replicative DNA helicase of Trichodesmium erythraeum. Molecular microbiology, 51(4), 1185-1192.

\* cited by examiner

CL: clarified expressed lysate;
F.T: flow through column; E: elution

Immobilization mechanism

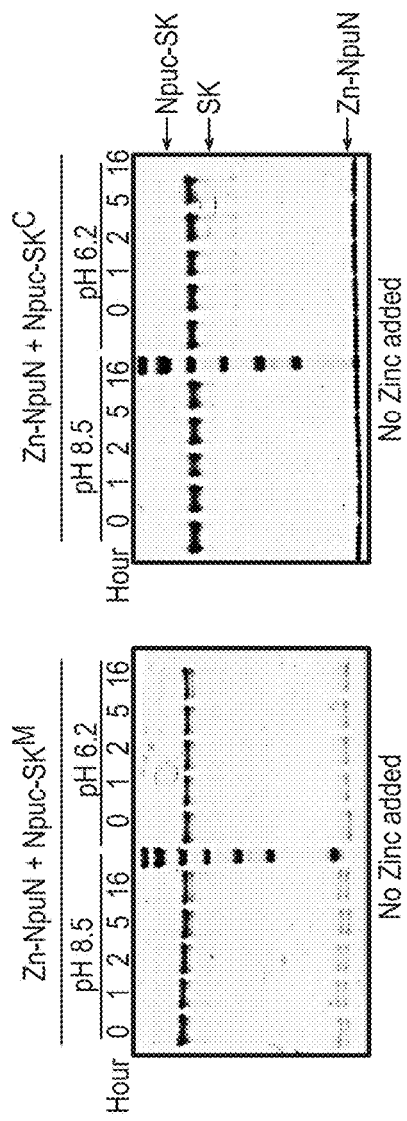
FIG. 19A
FIG. 19B
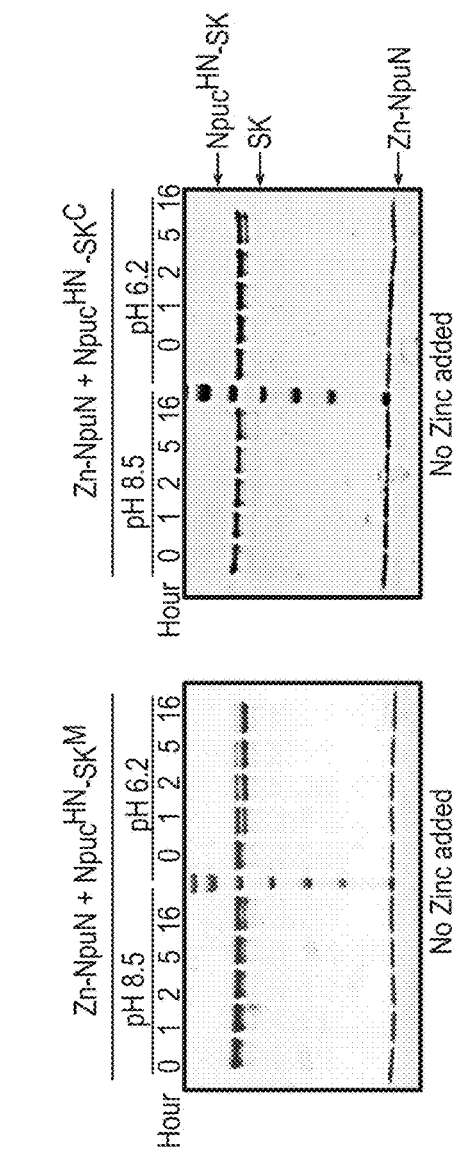
FIG. 20A
FIG. 20B

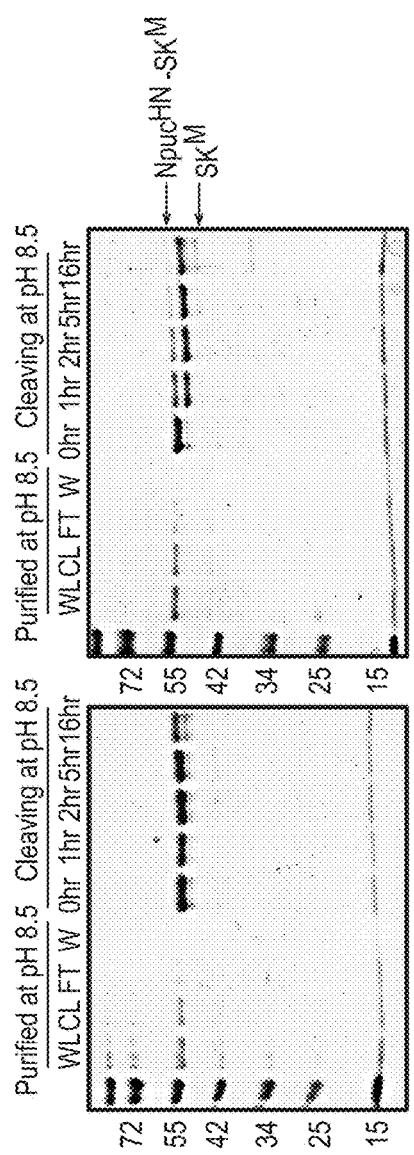
FIG. 21A
FIG. 21B
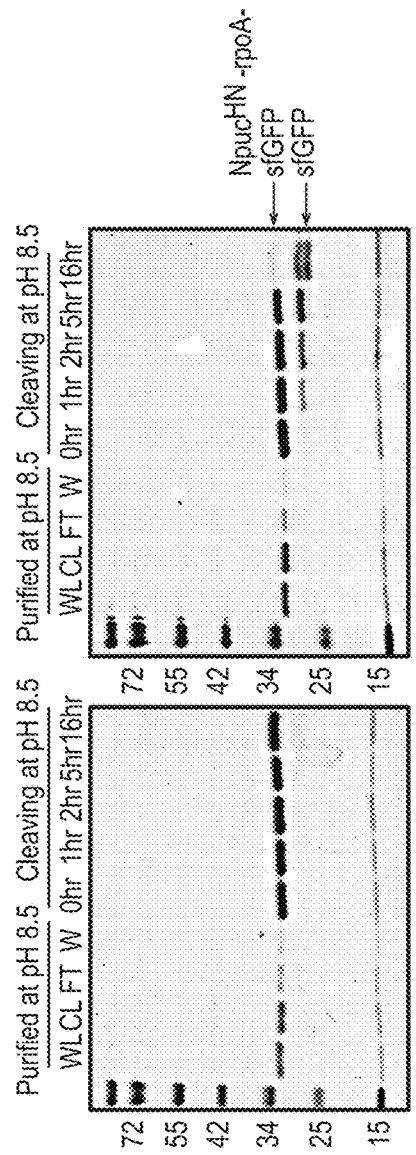
FIG. 22A
FIG. 22B

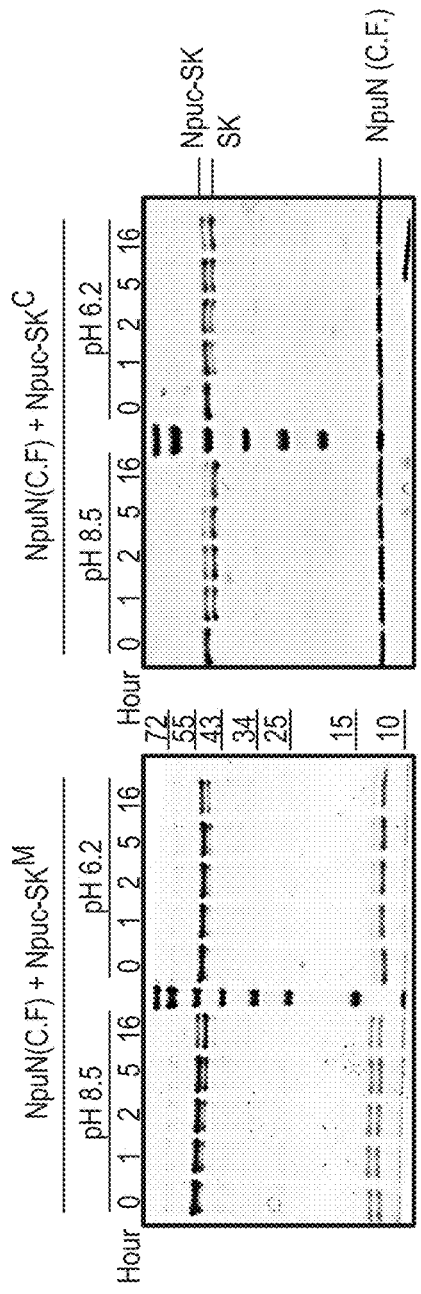
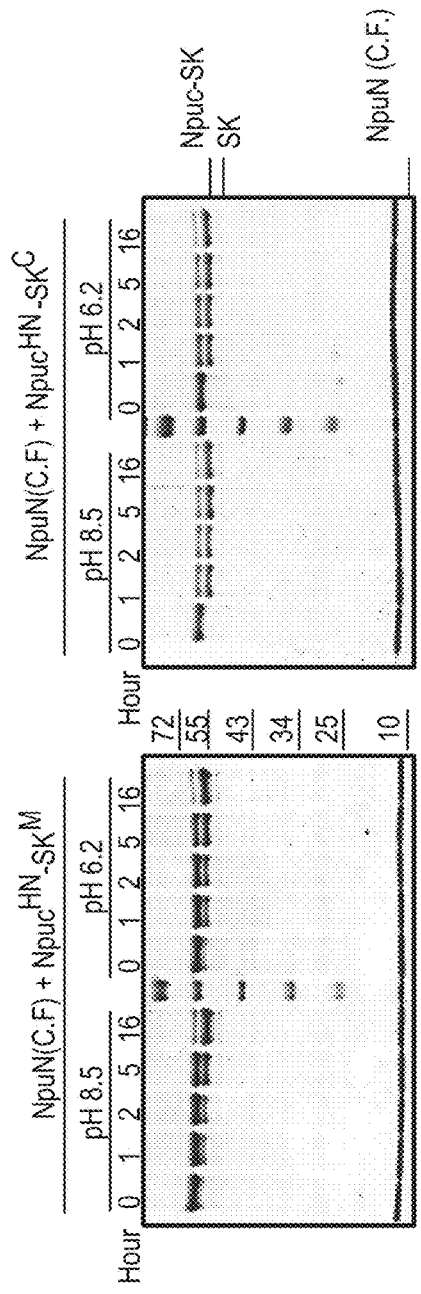
FIG. 23A  FIG. 23B  FIG. 23C  FIG. 23D

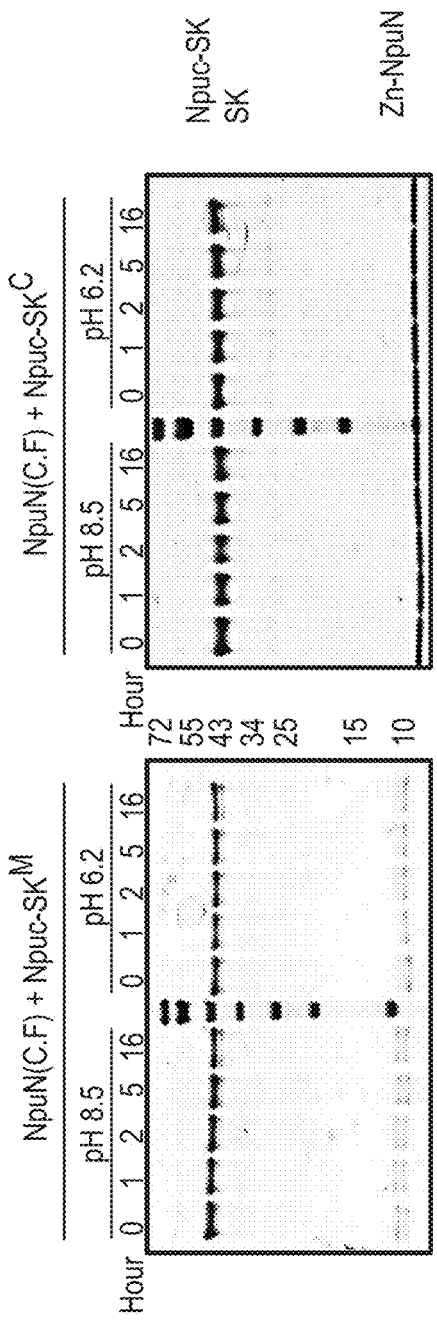
FIG. 25A
FIG. 25B
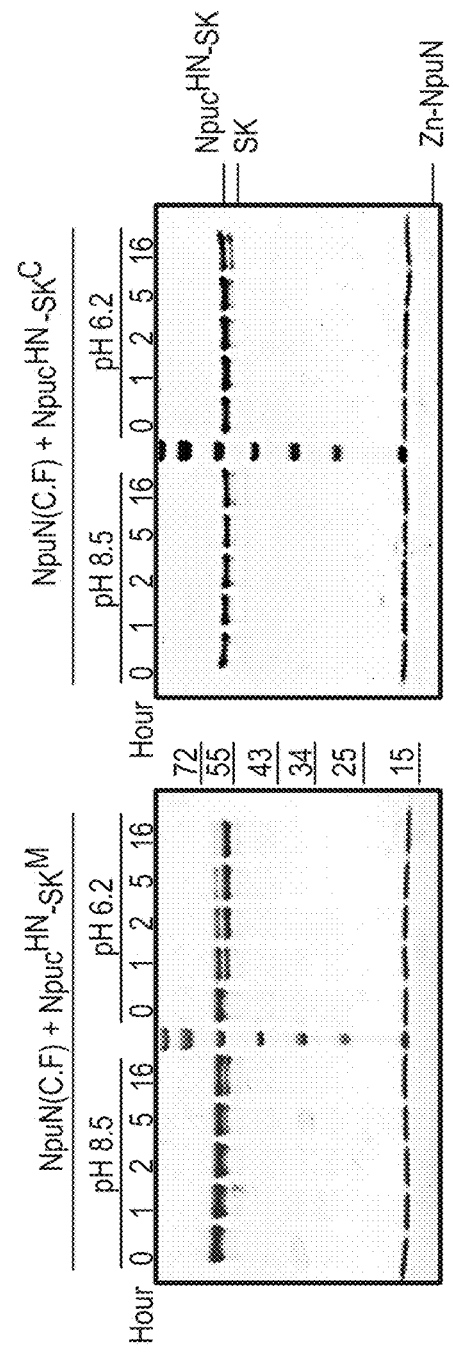
FIG. 25C
FIG. 25D

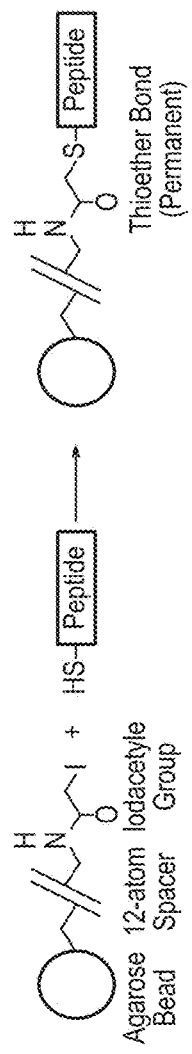
FIG. 26
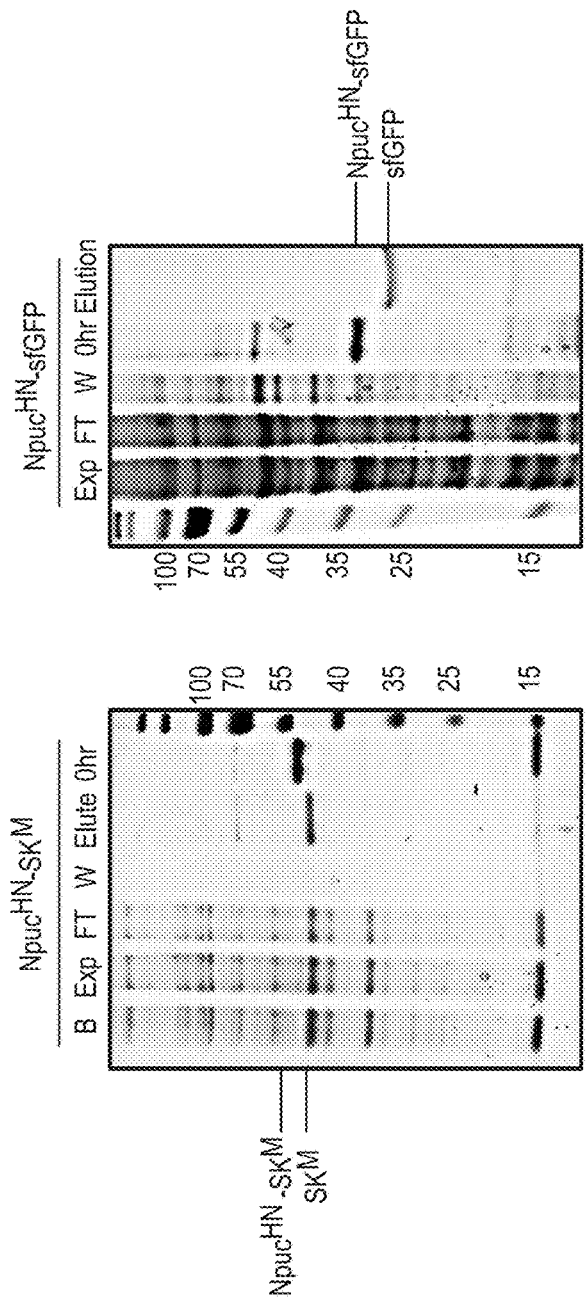
FIG. 27A
FIG. 27B

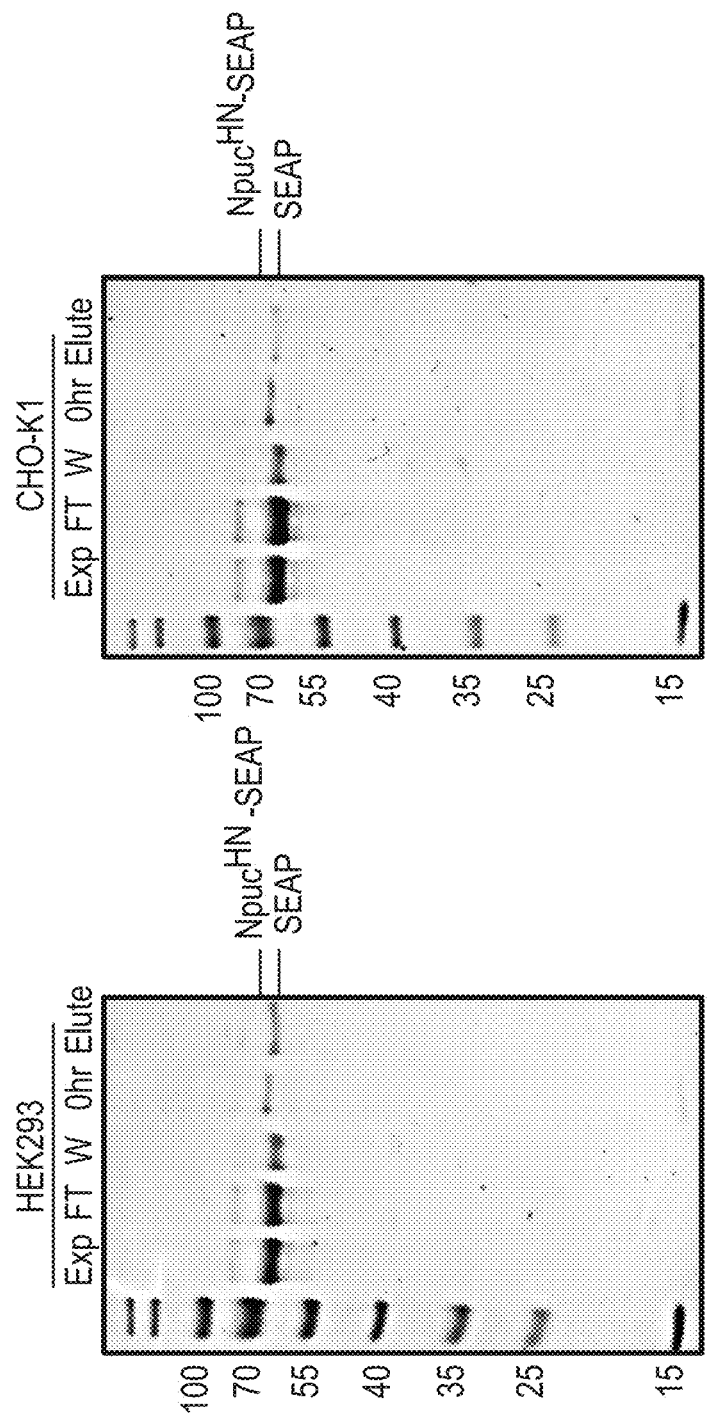

SEQUENCE LISTING

<160> NUMBER OF SEQ ID NOS: 34

<210> SEQ ID NO 1
<211> LENGTH: 102
<212> TYPE: PRT
<213> ORGANISM: Artificial Sequence
<220> FEATURE:
<223> OTHER INFORMATION: Synthetic

<400> SEQUENCE: 1

```
Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
                20                  25                  30

Val Asp Asn Asn Gly Asn Ile Tyr Thr Gln Pro Val Ala Gln Trp His
            35                  40                  45

Asp Arg Gly Glu Gln Glu Val Phe Glu Tyr Cys Leu Glu Asp Gly Ser
        50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
```

100

<210> SEQ ID NO 2
<211> LENGTH: 102
<212> TYPE: PRT
<213> ORGANISM: Artificial Sequence
<220> FEATURE:
<223> OTHER INFORMATION: Synthesized
<220> FEATURE:
<221> NAME/KEY: X
<222> LOCATION: (1)..(1)
<223> OTHER INFORMATION: X is alanine or glycine

<400> SEQUENCE: 2

```
Xaa Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Ser Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Ser Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn
            100
```

<210> SEQ ID NO 3
<211> LENGTH: 116
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (1)..(1)
<223> OTHER INFORMATION: X is alanine or glycine

<400> SEQUENCE: 3

```
Xaa Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Ser Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Ser Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn Gly Gly Gly Ser His His His His
            100                 105                 110

His Cys Cys Cys
        115
```

<210> SEQ ID NO 4
<211> LENGTH: 108
<212> TYPE: PRT

<213> ORGANISM: Artificial Sequence
<220> FEATURE:
<223> OTHER INFORMATION: Synthetic
<220> FEATURE:
<221> NAME/KEY: X
<222> LOCATION: (7)..(7)
<223> OTHER INFORMATION: X is alanine or glycine

<400> SEQUENCE: 4

```
Met Gly Asp Gly His Gly Xaa Leu Ser Tyr Glu Thr Glu Ile Leu Thr
1               5                   10                  15

Val Glu Tyr Gly Leu Leu Pro Ile Gly Lys Ile Val Glu Lys Arg Ile
            20                  25                  30

Glu Ser Thr Val Tyr Ser Val Asp Asn Asn Gly Asn Ile Tyr Thr Gln
        35                  40                  45

Pro Val Ala Gln Trp His Asp Arg Gly Glu Gln Glu Val Phe Glu Tyr
    50                  55                  60

Ser Leu Glu Asp Gly Ser Leu Ile Arg Ala Thr Lys Asp His Lys Phe
65                  70                  75                  80

Met Thr Val Asp Gly Gln Met Leu Pro Ile Asp Glu Ile Phe Glu Arg
                85                  90                  95

Glu Leu Asp Leu Met Arg Val Asp Asn Leu Pro Asn
            100                 105
```

<210> SEQ ID NO 5
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (7)..(7)
<223> OTHER INFORMATION: X is alanine or glycine

<400> SEQUENCE: 5

```
Met Gly Asp Gly His Gly Xaa Leu Ser Tyr Glu Thr Glu Ile Leu Thr
1               5                   10                  15

Val Glu Tyr Gly Leu Leu Pro Ile Gly Lys Ile Val Glu Lys Arg Ile
            20                  25                  30

Glu Ser Thr Val Tyr Ser Val Asp Asn Asn Gly Asn Ile Tyr Thr Gln
        35                  40                  45

Pro Val Ala Gln Trp His Asp Arg Gly Glu Gln Glu Val Phe Glu Tyr
    50                  55                  60

Ser Leu Glu Asp Gly Ser Leu Ile Arg Ala Thr Lys Asp His Lys Phe
65                  70                  75                  80

Met Thr Val Asp Gly Gln Met Leu Pro Ile Asp Glu Ile Phe Glu Arg
                85                  90                  95

Glu Leu Asp Leu Met Arg Val Asp Asn Leu Pro Asn Gly Gly Gly
            100                 105                 110

Ser His His His His His Cys Cys Cys
        115                 120
```

<210> SEQ ID NO 6
<211> LENGTH: 171
<212> TYPE: PRT
<213> ORGANISM: Artificial Sequence
<220> FEATURE:
<223> OTHER INFORMATION: Synthetic

<400> SEQUENCE: 6

Met Gly Asp Gly His Gly Ala Leu Ser Tyr Glu Thr Glu Ile Leu Thr
1               5                   10                  15

Val Glu Tyr Gly Leu Leu Pro Ile Gly Lys Ile Val Glu Lys Arg Ile
            20                  25                  30

Glu Ser Thr Val Tyr Ser Val Asp Asn Asn Gly Asn Ile Tyr Thr Gln
        35                  40                  45

Pro Val Ala Gln Trp His Asp Arg Gly Glu Gln Glu Val Phe Glu Tyr
    50                  55                  60

Ser Leu Glu Asp Gly Ser Leu Ile Arg Ala Thr Lys Asp His Lys Phe
65                  70                  75                  80

Met Thr Val Asp Gly Gln Met Leu Pro Ile Asp Glu Ile Phe Glu Arg
                85                  90                  95

Glu Leu Asp Leu Met Arg Val Asp Asn Leu Pro Asn Gly Gly Gly Gly
            100                 105                 110

Ser Gly Gly Gly Gly Ser Met Thr Thr Asn Pro Gly Val Ser Ala Trp
        115                 120                 125

Gln Val Asn Thr Ala Tyr Thr Ala Gly Gln Leu Val Thr Tyr Asn Gly
    130                 135                 140

Lys Thr Tyr Lys Cys Leu Gln Pro His Thr Ser Leu Ala Gly Trp Glu
145                 150                 155                 160

Pro Ser Asn Val Pro Ala Leu Trp Gln Leu Gln
                165                 170

<210> SEQ ID NO 7
<211> LENGTH: 686
<212> TYPE: PRT
<213> ORGANISM: Artificial Sequence
<220> FEATURE:
<223> OTHER INFORMATION: Synthetic

<400> SEQUENCE: 7

Met Gly His Gly Val Gly Val Pro Gly Val Gly Val Pro Gly Gly Gly
1               5                   10                  15

Val Pro Gly Ala Gly Val Pro Gly Val Gly Val Pro Gly Val Gly Val
            20                  25                  30

Pro Gly Val Gly Val Pro Gly Gly Val Pro Gly Val Gly Val Pro Gly
        35                  40                  45

Gly Gly Val Pro Gly Val Gly Val Pro Gly Val Gly Val Pro Gly Gly
    50                  55                  60

Gly Val Pro Gly Ala Gly Val Pro Gly Gly Val Pro Gly Val Gly Val
65                  70                  75                  80

Gly Val Pro Gly Val Gly Val Pro Gly Gly Val Pro Gly Val Gly Val
                85                  90                  95

Val Pro Gly Gly Gly Val Pro Gly Val Gly Val Pro Gly Val Gly Val
            100                 105                 110

Pro Gly Gly Gly Val Pro Gly Ala Gly Val Pro Gly Val Gly Val Pro
        115                 120                 125

Gly Val Gly Val Pro Gly Val Gly Val Pro Gly Gly Gly Val Pro Gly
    130                 135                 140

Ala Gly Val Pro Gly Gly Val Pro Gly Val Gly Val Pro Gly Val Gly
145                 150                 155                 160

Gly Val Pro Gly Gly Gly Val Pro Gly Ala Gly Val Pro Gly Val Gly
                165                 170                 175

Val Pro Gly Val Gly Val Pro Gly Val Gly Val Pro Gly Gly Gly Val
            180                 185                 190

-continued

Pro Gly Ala Gly Val Pro Gly Gly Gly Val Pro Gly Val Pro
            195                 200                 205

Gly Val Gly Val Pro Gly Gly Gly Val Pro Gly Ala Gly Val Pro Gly
210                 215                 220

Val Gly Val Pro Gly Val Gly Val Pro Gly Val Gly Val Pro Gly Gly
225                 230                 235                 240

Gly Val Pro Gly Ala Gly Val Pro Gly Gly Gly Val Pro Gly Val Gly
                245                 250                 255

Val Pro Gly Val Gly Val Pro Gly Gly Gly Val Pro Gly Ala Gly Val
            260                 265                 270

Pro Gly Val Gly Val Pro Gly Val Gly Val Pro Gly Val Gly Val Pro
            275                 280                 285

Gly Gly Gly Val Pro Gly Ala Gly Val Pro Gly Gly Gly Val Pro Gly
            290                 295                 300

Val Gly Val Pro Gly Val Gly Val Pro Gly Gly Gly Val Pro Gly Ala
305                 310                 315                 320

Gly Val Pro Gly Val Gly Val Pro Gly Val Gly Val Pro Gly Val Gly
                325                 330                 335

Val Pro Gly Gly Gly Val Pro Gly Ala Gly Val Pro Gly Gly Gly Val
            340                 345                 350

Pro Gly Val Gly Val Pro Gly Val Gly Val Pro Gly Gly Gly Val Pro
            355                 360                 365

Gly Ala Gly Val Pro Gly Val Gly Val Pro Gly Val Gly Val Pro Gly
            370                 375                 380

Val Gly Val Pro Gly Gly Gly Val Pro Gly Ala Gly Val Pro Gly Gly
385                 390                 395                 400

Gly Val Pro Gly Val Gly Val Pro Gly Val Gly Val Pro Gly Gly Gly
                405                 410                 415

Val Pro Gly Ala Gly Val Pro Gly Val Gly Val Pro Gly Val Gly Val
            420                 425                 430

Pro Gly Val Gly Val Pro Gly Gly Gly Val Pro Gly Ala Gly Val Pro
            435                 440                 445

Gly Gly Gly Val Pro Gly Val Gly Val Pro Gly Val Gly Val Pro Gly
            450                 455                 460

Gly Gly Val Pro Gly Ala Gly Val Pro Gly Val Gly Val Pro Gly Val
465                 470                 475                 480

Gly Val Pro Gly Val Gly Val Pro Gly Gly Gly Val Pro Gly Ala Gly
                485                 490                 495

Val Pro Gly Gly Gly Val Pro Gly Val Gly Val Pro Gly Val Gly Val
            500                 505                 510

Pro Gly Gly Gly Val Pro Gly Ala Gly Val Pro Gly Val Gly Val Pro
            515                 520                 525

Gly Val Gly Val Pro Gly Val Gly Val Pro Gly Gly Gly Val Pro Gly
            530                 535                 540

Ala Gly Val Pro Gly Gly Gly Val Pro Gly Gly Leu Val Ser Ser Asn
545                 550                 555                 560

Asn Asn Asn Asn Asn Asn Asn Asn Leu Gly Ile Glu Gly Arg Ile
                565                 570                 575

Ser Glu Phe Gly Asp Gly His Gly Ala Leu Ser Tyr Glu Thr Glu Ile
            580                 585                 590

Leu Thr Val Glu Tyr Gly Leu Leu Pro Ile Gly Lys Ile Val Glu Lys
            595                 600                 605

Arg Ile Glu Ser Thr Val Tyr Ser Val Asp Asn Asn Gly Asn Ile Tyr

```
            610                 615                 620
Thr Gln Pro Val Ala Gln Trp His Asp Arg Gly Glu Gln Glu Val Phe
625                 630                 635                 640

Glu Tyr Ser Leu Glu Asp Gly Ser Leu Ile Arg Ala Thr Lys Asp His
                645                 650                 655

Lys Phe Met Thr Val Asp Gly Gln Met Leu Pro Ile Asp Glu Ile Phe
            660                 665                 670

Glu Arg Glu Leu Asp Leu Met Arg Val Asp Asn Leu Pro Asn
        675                 680                 685

<210> SEQ ID NO 8
<211> LENGTH: 35
<212> TYPE: PRT
<213> ORGANISM: Artificial Sequence
<220> FEATURE:
<223> OTHER INFORMATION: Synthetic

<400> SEQUENCE: 8

Ile Lys Ile Ala Thr Arg Lys Tyr Leu Gly Lys Gln Asn Val Tyr Asp
1               5                   10                  15

Ile Gly Val Glu Arg Asp His Asn Phe Ala Leu Lys Asn Gly Phe Ile
            20                  25                  30

Ala Ser Asn
        35

<210> SEQ ID NO 9
<211> LENGTH: 35
<212> TYPE: PRT
<213> ORGANISM: Artificial Sequence
<220> FEATURE:
<223> OTHER INFORMATION: Synthetic

<400> SEQUENCE: 9

Ile Lys Ile Ala Thr Arg Lys Tyr Leu Gly Lys Gln Asn Val Tyr Gly
1               5                   10                  15

Ile Gly Val Glu Arg Asp His Asn Phe Ala Leu Lys Asn Gly Phe Ile
            20                  25                  30

Ala His Asn
        35

<210> SEQ ID NO 10
<211> LENGTH: 415
<212> TYPE: PRT
<213> ORGANISM: Artificial Sequence
<220> FEATURE:
<223> OTHER INFORMATION: Synthetic

<400> SEQUENCE: 10

Cys Ile Ala Gly Pro Glu Trp Leu Leu Asp Arg Pro Ser Val Asn Asn
1               5                   10                  15

Ser Gln Leu Val Val Ser Val Ala Gly Thr Val Glu Gly Thr Asn Gln
            20                  25                  30

Asp Ile Ser Leu Lys Phe Phe Glu Ile Asp Leu Thr Ser Arg Pro Ala
        35                  40                  45

His Gly Gly Lys Thr Glu Gln Gly Leu Ser Pro Lys Ser Lys Pro Phe
    50                  55                  60

Ala Thr Asp Ser Gly Ala Met Ser His Lys Leu Glu Lys Ala Asp Leu
65                  70                  75                  80

Leu Lys Ala Ile Gln Glu Gln Leu Ile Ala Asn Val His Ser Asn Asp
                85                  90                  95
```

Asp Tyr Phe Glu Val Ile Asp Phe Ala Ser Asp Ala Thr Ile Thr Asp
            100                 105                 110

Arg Asn Gly Lys Val Tyr Phe Ala Asp Lys Asp Gly Ser Val Thr Leu
            115                 120                 125

Pro Thr Gln Pro Val Gln Glu Phe Leu Leu Ser Gly His Val Arg Val
            130                 135                 140

Arg Pro Tyr Lys Glu Lys Pro Ile Gln Asn Gln Ala Lys Ser Val Asp
145                 150                 155                 160

Val Glu Tyr Thr Val Gln Phe Thr Pro Leu Asn Pro Asp Asp Asp Phe
            165                 170                 175

Arg Pro Gly Leu Lys Asp Thr Lys Leu Leu Lys Thr Leu Ala Ile Gly
            180                 185                 190

Asp Thr Ile Thr Ser Gln Glu Leu Leu Ala Gln Ala Gln Ser Ile Leu
            195                 200                 205

Asn Lys Asn His Pro Gly Tyr Thr Ile Tyr Glu Arg Asp Ser Ser Ile
            210                 215                 220

Val Thr His Asp Asn Asp Ile Phe Arg Thr Ile Leu Pro Met Asp Gln
225                 230                 235                 240

Glu Phe Thr Tyr Arg Val Lys Asn Arg Glu Gln Ala Tyr Arg Ile Asn
            245                 250                 255

Lys Lys Ser Gly Leu Asn Glu Glu Ile Asn Asn Thr Asp Leu Ile Ser
            260                 265                 270

Glu Lys Tyr Tyr Val Leu Lys Lys Gly Glu Lys Pro Tyr Asp Pro Phe
            275                 280                 285

Asp Arg Ser His Leu Lys Leu Phe Thr Ile Lys Tyr Val Asp Val Asp
            290                 295                 300

Thr Asn Glu Leu Leu Lys Ser Glu Gln Leu Leu Thr Ala Ser Glu Arg
305                 310                 315                 320

Asn Leu Asp Phe Arg Asp Leu Tyr Asp Pro Arg Asp Lys Ala Lys Leu
            325                 330                 335

Leu Tyr Asn Asn Leu Asp Ala Phe Gly Ile Met Asp Tyr Thr Leu Thr
            340                 345                 350

Gly Lys Val Glu Asp Asn His Asp Asp Thr Asn Arg Ile Ile Thr Val
            355                 360                 365

Tyr Met Gly Lys Arg Pro Glu Gly Glu Asn Ala Ser Tyr His Leu Ala
            370                 375                 380

Tyr Asp Lys Asp Arg Tyr Thr Glu Glu Arg Glu Val Tyr Ser Tyr
385                 390                 395                 400

Leu Arg Tyr Thr Gly Thr Pro Ile Pro Asp Asn Pro Asn Asp Lys
            405                 410                 415

<210> SEQ ID NO 11
<211> LENGTH: 264
<212> TYPE: PRT
<213> ORGANISM: Artificial Sequence
<220> FEATURE:
<223> OTHER INFORMATION: Synthetic

<400> SEQUENCE: 11

Met His Pro Glu Thr Leu Val Lys Val Lys Asp Ala Glu Asp Gln Leu
1               5                   10                  15

Gly Ala Arg Val Gly Tyr Ile Glu Leu Asp Leu Asn Ser Gly Lys Ile
            20                  25                  30

Leu Glu Ser Phe Arg Pro Glu Glu Arg Phe Pro Met Met Ser Thr Phe
            35                  40                  45

Lys Val Leu Leu Cys Gly Ala Val Leu Ser Arg Ile Asp Ala Gly Gln
            50                  55                  60

Glu Gln Leu Gly Arg Arg Ile His Tyr Ser Gln Asn Asp Leu Val Glu
 65                  70                  75                  80

Tyr Ser Pro Val Thr Glu Lys His Leu Thr Asp Gly Met Thr Val Arg
                85                  90                  95

Glu Leu Cys Ser Ala Ala Ile Thr Met Ser Asp Asn Thr Ala Ala Asn
            100                 105                 110

Leu Leu Leu Thr Thr Ile Gly Gly Pro Lys Glu Leu Thr Ala Phe Leu
            115                 120                 125

His Asn Met Gly Asp His Val Thr Arg Leu Asp Arg Trp Glu Pro Glu
            130                 135                 140

Leu Asn Glu Ala Ile Pro Asn Asp Glu Arg Asp Thr Thr Met Pro Val
145                 150                 155                 160

Ala Met Ala Thr Thr Leu Arg Lys Leu Leu Thr Gly Glu Leu Leu Thr
                165                 170                 175

Leu Ala Ser Arg Gln Gln Leu Ile Asp Trp Met Glu Ala Asp Lys Val
            180                 185                 190

Ala Gly Pro Leu Leu Arg Ser Ala Leu Pro Ala Gly Trp Phe Ile Ala
            195                 200                 205

Asp Lys Ser Gly Ala Gly Glu Arg Gly Ser Arg Gly Ile Ile Ala Ala
            210                 215                 220

Leu Gly Pro Asp Gly Lys Pro Ser Arg Ile Val Val Ile Tyr Thr Thr
225                 230                 235                 240

Gly Ser Gln Ala Thr Met Asp Glu Arg Asn Arg Gln Ile Ala Glu Ile
                245                 250                 255

Gly Ala Ser Leu Ile Lys His Trp
            260

<210> SEQ ID NO 12
<211> LENGTH: 241
<212> TYPE: PRT
<213> ORGANISM: Artificial Sequence
<220> FEATURE:
<223> OTHER INFORMATION: Synthetic

<400> SEQUENCE: 12

Cys Phe Asn Val Ser Lys Gly Glu Glu Leu Phe Thr Gly Val Val Pro
 1               5                  10                  15

Ile Leu Val Glu Leu Asp Gly Asp Val Asn Gly His Lys Phe Ser Val
                20                  25                  30

Ser Gly Glu Gly Glu Gly Asp Ala Thr Tyr Gly Lys Leu Thr Leu Lys
            35                  40                  45

Phe Ile Cys Thr Thr Gly Lys Leu Pro Val Pro Trp Pro Thr Leu Val
            50                  55                  60

Thr Thr Leu Thr Tyr Gly Val Gln Cys Phe Ser Arg Tyr Pro Asp His
 65                  70                  75                  80

Met Lys Gln His Asp Phe Phe Lys Ser Ala Met Pro Glu Gly Tyr Val
                85                  90                  95

Gln Glu Arg Thr Ile Phe Phe Lys Asp Asp Gly Asn Tyr Lys Thr Arg
            100                 105                 110

Ala Glu Val Lys Phe Glu Gly Asp Thr Leu Val Asn Arg Ile Glu Leu
            115                 120                 125

Lys Gly Ile Asp Phe Lys Glu Asp Gly Asn Ile Leu Gly His Lys Leu
            130                 135                 140

Glu Tyr Asn Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr Leu Gly Met Asp Glu Leu Tyr
225                 230                 235                 240

Lys

<210> SEQ ID NO 13
<211> LENGTH: 371
<212> TYPE: PRT
<213> ORGANISM: Artificial Sequence
<220> FEATURE:
<223> OTHER INFORMATION: Synthetic

<400> SEQUENCE: 13

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

```
Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser
    370
```

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

```
Gly Glu Gly His His
1               5
```

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

```
Gly Glu Gly His Gly
1               5
```

<210> SEQ ID NO 16
<211> LENGTH: 5
<212> TYPE: PRT
<213> ORGANISM: Artificial Sequence
<220> FEATURE:
<223> OTHER INFORMATION: Synthetic

<400> SEQUENCE: 16

```
Gly Asp Gly His His
1               5
```

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

```
Gly Asp Gly His Gly
1               5
```

<210> SEQ ID NO 18
<211> LENGTH: 35

```
<212> TYPE: DNA
<213> ORGANISM: Artificial Sequence
<220> FEATURE:
<223> OTHER INFORMATION: Synthetic

<400> SEQUENCE: 18
ggagagggac atcacctcgc agagggcact cggat                        35

<210> SEQ ID NO 19
<211> LENGTH: 35
<212> TYPE: DNA
<213> ORGANISM: Artificial Sequence
<220> FEATURE:
<223> OTHER INFORMATION: Synthetic

<400> SEQUENCE: 19
ggagagggac attgcctcgc agagggcact cggat                        35

<210> SEQ ID NO 20
<211> LENGTH: 35
<212> TYPE: DNA
<213> ORGANISM: Artificial Sequence
<220> FEATURE:
<223> OTHER INFORMATION: Synthetic

<400> SEQUENCE: 20
ggagagggac atcatgccct cgcagagggc actcg                        35

<210> SEQ ID NO 21
<211> LENGTH: 36
<212> TYPE: DNA
<213> ORGANISM: Artificial Sequence
<220> FEATURE:
<223> OTHER INFORMATION: Synthetic

<400> SEQUENCE: 21
ggagagggac atggatgcct cgcagagggc actcgg                       36

<210> SEQ ID NO 22
<211> LENGTH: 37
<212> TYPE: DNA
<213> ORGANISM: Artificial Sequence
<220> FEATURE:
<223> OTHER INFORMATION: Synthetic

<400> SEQUENCE: 22
ggagatggac atcatgccct cgcagagggc actcgga                      37

<210> SEQ ID NO 23
<211> LENGTH: 37
<212> TYPE: DNA
<213> ORGANISM: Artificial Sequence
<220> FEATURE:
<223> OTHER INFORMATION: Synthetic

<400> SEQUENCE: 23
ggagatggac atggatgcct cgcagagggc actcgga                      37

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24
```

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

His Leu Ala Glu Gly Thr Arg Ile
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Cys Leu Ala Glu Gly Thr Arg Ile
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Ala Leu Ala Glu Gly Thr Arg Ile
1               5

<210> SEQ ID NO 28
<211> LENGTH: 21
<212> TYPE: PRT
<213> ORGANISM: Artificial Sequence
<220> FEATURE:
<223> OTHER INFORMATION: Synthetic

<400> SEQUENCE: 28

Met Glu Thr Asp Thr Leu Leu Leu Trp Val Leu Leu Leu Trp Val Pro
1               5                   10                  15

Gly Ser Thr Gly Asp
            20

<210> SEQ ID NO 29
<211> LENGTH: 35
<212> TYPE: DNA
<213> ORGANISM: Artificial Sequence
<220> FEATURE:
<223> OTHER INFORMATION: Synthetic

<400> SEQUENCE: 29
ggccatatga tggccttaag ctatgaaacg gaaat                              35

<210> SEQ ID NO 30
<211> LENGTH: 68
<212> TYPE: DNA
<213> ORGANISM: Artificial Sequence
<220> FEATURE:
<223> OTHER INFORMATION: Synthetic

<400> SEQUENCE: 30

```
gataatttgc cgaatggtgg aggaggatct gggggtggtg gttctatgac gacaaatcct    60
ggtgtatc                                                             68

<210> SEQ ID NO 31
<211> LENGTH: 69
<212> TYPE: DNA
<213> ORGANISM: Artificial Sequence
<220> FEATURE:
<223> OTHER INFORMATION: Synthetic

<400> SEQUENCE: 31
aggatttgtc gtcatagaac caccaccccc agatcctcct ccaccattcg gcaaattatc    60
aacccgcat                                                            69

<210> SEQ ID NO 32
<211> LENGTH: 27
<212> TYPE: DNA
<213> ORGANISM: Artificial Sequence
<220> FEATURE:
<223> OTHER INFORMATION: Synthetic

<400> SEQUENCE: 32
ggcctcgagt gcggccgcaa gctttta                                        27

<210> SEQ ID NO 33
<211> LENGTH: 50
<212> TYPE: DNA
<213> ORGANISM: Artificial Sequence
<220> FEATURE:
<223> OTHER INFORMATION: Synthetic

<400> SEQUENCE: 33
ggccatatgc atcatcatca tcatcacatc aaaatagcca cacgtaaata                50

<210> SEQ ID NO 34
<211> LENGTH: 42
<212> TYPE: DNA
<213> ORGANISM: Artificial Sequence
<220> FEATURE:
<223> OTHER INFORMATION: Synthetic

<400> SEQUENCE: 34
gtggtggtgc tcgagtcatt atttgtcatt gggattgtcg gg                       42
```

PROTEIN PRODUCTION SYSTEMS AND METHODS THEREOF

CROSS-REFERENCE TO RELATED APPLICATIONS

This application claims the benefit of U.S. Application No. 62/101,518, filed on Jan. 9, 2015, which is hereby incorporated by reference in its entirety.

STATEMENT REGARDING FEDERALLY SPONSORED RESEARCH

This invention was made with government support under grant 0000012879 awarded by Defense Advanced Research Projects Agency (DARPA). The United States government has certain rights in the invention.

BACKGROUND

Inteins are naturally occurring, self-splicing protein subdomains that are capable of excising out their own protein subdomain from a larger protein structure while simultaneously joining the two formerly flanking peptide regions ("exteins") together to form a mature host protein.

The ability of inteins to rearrange flanking peptide bonds, and retain activity when in fusion to proteins other than their native exteins, has led to a number of intein-based biotechnologies. These include various types of protein ligaton and activation applications, as well as protein labeling and tracing applications. An important application of inteins is in the production of purified recombinant proteins. In particular, inteins have the ability to impart self-cleaving activity to a number of conventional affinity and purification tags, and thus provide a major advance in the production of recombinant protein products for research, medical and other commercial applications.

Conventional purification tags provide a simple and robust means for purifying any tagged target protein, and are commonly added to desired target proteins through simple genetic fusions. These tags are now ubiquitous in research, and have formed a major platform for research and manufacturing of these important products. Once the tagged target protein is expressed in an appropriate host cell and purified via the tag, however, the presence of the tag on the purified target can lead to compromised activity, and potentially unwanted immunogenicity in the case of therapeutic protens. For these reasons, the ability to remove the affinity tag after purification is of critical importance in many applications, which is conventionally done through the addition of highly specific endopeptidase enzymes. Although these enzymes are generally effective, they are too expensive to scale up for manufacturing, and their use requires an additional step for their removal.

Thus, the ability of inteins to impart self-cleaving activity to conventional tags is a significant advance, and early implementations of intein-based self-cleaving affinity tag systems have been published in several patents and hundreds of journal papers in the biological sciences. Despite their strength, however, several substantial weaknesses remain that inhibit the full implementation of intein methods. In particular, the ability to tightly control the cleaving reaction in a variety of highly relevant contexts has been elusive. In order to be useful, the intein self-cleaving reaction must be tightly suppressed during protein expression and purification, but very rapid once the tagged target protein is pure. Of the two available classes of conventional inteins, one is highly controllable and is triggered to cleave by addition of thiol compounds, while the other is more loosely controlled and is triggered by small changes in pH and temperature.

Therefore, what is needed is a method for selective protein purification using a stable, transformative intein system. This system has significant utility in accelerated protein production and purification, with numerous applications in biological research, medicine and biopharmacueitical manufacturing. In particular, this intein system must be compatible with eukaryotic expression host systems, to be used for the expression and purification of complex glycoproteins. Some included areas of impact would be rapid anti-infectious disease vaccine manufacture, bioterrorism defense, and personalized anti-cancer antigen generation, as well as contributions to pure research and the acceleration of new drug evaluation and optimization.

SUMMARY

In accordance with the purpose(s) of the invention, as embodied and broadly described herein, the invention, in one aspect, relates to a protein purification system, wherein the system comprises a split intein consisting of two separate peptides: an N-terminal intein segment and a C-terminal intein segment, wherein the N-terminal intein segment can be linked to a solid support, and wherein cleaving of the C-terminal intein segment is suppressed in the absence of the N-terminal intein segment, and wherein the assembled N-terminal and C-terminal intein segment complex is highly sensitive to extrinsic conditions when compared to a native intein complex.

Disclosed is a method of purifying a protein of interest, the method comprising: utilizing a split intein comprising two separate peptides: an N-terminal intein segment and a C-terminal intein segment; immobilizing the N-terminal intein segment to a solid support; genetically fusing (or "tagging") a protein of interest to the C-terminal intein segment, wherein cleaving of the C-terminal intein segment is highly suppressed in the absence of the N-terminal intein segment; exposing the N-terminal intein segment and the C-terminal intein segment to each other so that they associate on the solid support; washing the solid support to remove non-bound contaminating material; placing the associated the N-terminal intein segment and the C-terminal intein segment under conditions that allow for the intein to self-cleave; and isolating the protein of interest.

Also disclosed is a protein purification system, wherein the system comprises a split intein comprising two separate peptides: an N-terminal intein segment and a C-terminal intein segment, wherein the N-terminal intein segment does not comprise any internal cysteine residues.

Also disclosed is protein purification system, wherein the system comprises a split intein comprising two separate peptides: N-terminal intein segment and a C-terminal intein segment, wherein the N-terminal intein segment comprises a His-tag and/or one or more cysteine residues at its C-terminus.

Also disclosed is protein purification system, wherein the system comprises a split intein comprising two separate peptides: N-terminal intein segment and a C-terminal intein segment, wherein the C-terminal intein segment comprises a serine to histidine mutation at the penultimate residue of the C-terminal intein segment.

Also disclosed is protein purification system, wherein the system comprises a split intein comprising two separate peptides: N-terminal intein segment and a C-terminal intein segment, wherein the N-terminal intein segment comprises a sensitivity-enhancing motif for controlled cleavage of the C-terminal segment in the assembled intein complex.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 2A shows SEQ ID NO: 4. The native sequence of the N-terminal intein segment starts with "$C_1$LSYET . . . ", and is shown along with the locations of the three cysteine residues that have been mutated to either alanine (C1A), glycine (C1G) or serine (C29S, C60S) for cleaving analysis. The sequence GDGHGC of SEQ ID NO: 4 preceding the intein is the sensitivity-enhancing motif described later in this patent. FIG. 2B shows an SDS-PAGE analysis of cysteine mutation effects on C-cleaving under various test conditions, as well as the effect of the C1G (initial Cysteine of the intein mutated to Glycine) on the CF N-terminal segment. For each mutant, cleavage was evaluated for three hours at room temperature (RT) in the buffer indicated at the bottom of the gel. Cleavage conditions were tested as indicated in the figure (addition of 1 mM $ZnCl_2$, nothing (buffer only), or 50 mM Dithiothreitol (DTT)). Lanes labeled 0h are the initial $Npu^{D-G}_C$-SKhis test protein before cleaving has taken place. "WT" indicates the wild type N-terminal intein segment. In all cases, the mutations of Cysteine to Serine within the intein were observed to have minimal affects on cleaving rates of the assembled intein complex under the conditions shown.

FIG. 3A shows the purified N-terminal intein segment ($Npu_N^{CF}$(C1A)—in lanes L (Load) and FT (Flow Through) under 'N' at the far left of the gel) that was covalently immobilized onto the resin. Covalent immobilization was accomplished in this example using a spontaneous chemical coupling between three added N-terminal cysteine residues of the intein N-terminal segment and the active iodoacetyle group of the commercially available resin to form a covalent bond. The method used followed instructions in the manufacturer's handbook for the resin. The purified intein C-terminal segment fused to the SK test target protein ($Npu^{D-G}_C$-$SK^C$—in the lanes L and FT under 'C' at the left of the gel) is then incubated with the prepared resin on ice for 5 minutes, or flowed through at a rate of 0.5 ml/min to bind with the intein N-segment immobilized on the column. In this case, the notation $SK^C$ refers to the streptokinase target protein where the initial amino acid of the SK test protein has been mutated to Cysteine. The intein segments associate on the column to form an active cleaving complex, where the C-terminal segment is then induced to cleave off the target protein ($SK^C$) with 50 mM DTT. Different cleavage incubation time samples (0-3h) were analyzed (lanes 1, 2 and 3), showing the cleavage of the C-terminal intein segment and $SK^C$ target protein over time. The cleaved protein can then be directly collected from the column (elution fractions are shown in lanes E1, E2 and E3). After elution, the resin can be regenerated by a regeneration buffer (0.1 M NaOH, 0.5% Triton X100, 2 mM $ZnCl_2$) with incubation at 40° C. for half an hour. KEY: $R^{CL}$, resin after cleaving, showing uncleaved $Npu^{D-G}_C$-$SK^C$ fusion and cleaved $Npu^{D-G}_C$ still bound to the column; $E^R$, elution of cleaved proteins during regeneration; $R^R$, resin sample after regeneration showing loss of $Npu^{D-G}_C$-$SK^C$ fusion and cleaved $Npu^{D-G}_C$ as expected during regeneration. FIG. 3B shows the binding efficiencies and binding capacities between different purification methods (static or flow binding) after sequential rounds of regeneration (Regeneration time). These results collectively show purification of each intein segment (purified by His tag), as well as on-column binding and cleaving of the two purified segments. These results demonstrate the on-column association and cleaving ability of the intein segments, as well as the regeneration capability for the covalent $Npu_N^{CF}$ resin.

FIG. 13A shows results at 0 hours, FIG. 13B shows results at 1 hour, FIG. 13C shows results at 2 hours, and FIG. 13D shows results at 5 hours. FIG. 13E shows results at 16 hours. These data show that this intein combination shows little cleaving activity under any conditions of pH and temperature.

FIG. 14A shows results at 0 hours, FIG. 14B shows results at 1 hour, FIG. 14C shows results at 2 hours, and FIG. 14D shows results at 5 hours. FIG. 14E shows results at 16 hours. These data show that this intein combination shows little cleaving activity under any conditions of pH and temperature.

FIG. 15A shows results at 0 hours, FIG. 15B shows results at 1 hour, FIG. 15C shows results at 2 hours, and FIG. 15D shows results at 5 hours. FIG. 15E shows results at 16 hours. These data show a greatly enhanced cleavage rate and pH sensitivity of the intein cleaving reaction relative to the similar fusions shown above in the absence of the serine to histidine mutation.

FIG. 16A shows results at 0 hours, FIG. 16B shows results at 1 hour, FIG. 16C shows results at 2 hours, and FIG. 16D shows results at 5 hours. FIG. 16E shows results at 16 hours. These data also show enhanced pH sensitivity and cleavage rate for this intein combination relative to the segments lacking the serine to histidine mutation as shown above.

FIG. 17A shows the cleaving kinetics of C-terminal intein segment (Npu$_C$) and the target protein streptokinase (SK$^M$), using an N-terminal intein segment (Npu$_N$) for purification. FIG. 17B shows the cleaving kinetics of C-terminal intein segment (Npu$_C$) and the target protein streptokinase (SK$^C$). Proteins were expressed in *E. coli* (BLR culture), and then purified using Ni-NTA. The Npu$_N$ and Npu$_C$-SK$^C$ and SK$^M$ intein segments were mixed in solution at a molar ratio of 2:1. Cleaving occurred at room temperature for the indicated number of hours at the indicated pH in the absence of zinc. The buffer used was 20 mM AMPD/PIPES, and 500 mM NaCl. These data show that these intein segments exhibit some cleaving activity over this pH range, and that the cleaving activity is somewhat pH sensitive.

FIG. 18A shows the cleaving kinetics of C-terminal intein segment with a serine to histidine mutation (Npu$_C^{HN}$) and the target protein streptokinase (SK$^M$), using an N-terminal intein segment (Npu$_N$) for purification. FIG. 18B shows the cleaving kinetics of C-terminal intein segment (Npu$_C^{HN}$) streptokinase (SK$^C$) and N-terminal intein segment (Npu$_N$) for purification. Proteins were expressed in *E. coli* (BLR culture), and then purified using Ni-NTA. The Npu$_N$ and Npu$_C^{HN}$-SK$^C$ and SK$^M$ intein segments were mixed in solution at a molar ratio of 2:1. Cleaving occurred at room temperature for the indicated number of hours at the indicated pH in the absence of zinc. The buffer used was 20 mM AMPD/PIPES, and 500 mM NaCl. The data show that the cleaving is somewhat accelerated by the serine to histidine mutation, especially at pH 6.2, but that the pH sensitivity for cleaving is diminished.

FIGS. 19A-B show cleaving kinetics of the intein segments where the Npu$_C$ intein segment lacks the serine to histidine mutation, but there is the sensitivity-enhancing motif on the Zn-Npu$_N$ intein segment. Specifically, FIG. 19A shows the cleaving kinetics of C-terminal intein segment (Npu$_C$) and the target protein streptokinase (SK$^M$), using an N-terminal intein segment with a sensitivity-enhancing motif (Zn-Npu$_N$) for purification. FIG. 19B shows the cleaving kinetics of C-terminal intein segment (Npu$_C$) streptokinase (SK$^C$) and N-terminal intein segment with a sensitivity-enhancing motif (Zn-Npu$_N$) for purification. Proteins were expressed in *E. coli* (BLR culture), and then purified using Ni-NTA. The Zn-Npu$_N$ and Npu$_C$-SK$^C$ and SK$^M$ intein segments were mixed in solution at a molar ratio of 2:1. Cleaving occurred at room temperature for the indicated number of hours at the indicated pH in the absence of zinc. The buffer used was 20 mM AMPD/PIPES, and 500 mM NaCl. The data indicate that these intein segments exhibit almost no cleaving under all of the conditions shown.

FIGS. 20A and B shows cleaving kinetics of the intein segments where the Npu$_C$ intein segment has the serine to histidine mutation, and there is a sensitivity-enhancing motif on the Zn-Npu$_N$ intein segment. Specifically, FIG. 20A shows the cleaving kinetics of C-terminal intein segment with a serine to histidine mutation (Npu$_C^{HN}$) and the target protein streptokinase (SK$^M$), using an N-terminal intein segment with a sensitivity-enhancing motif (Zn-Npu$_N$) for purification. FIG. 20B shows the cleaving kinetics of C-terminal intein segment (Npu$_C^{HN}$) streptokinase (SK$^C$) and N-terminal intein segment with a sensitivity-enhancing motif (Zn-Npu$_N$) for purification. Proteins were expressed in *E. coli* (BLR culture), and then purified using Ni-NTA. The Zn-Npu$_N$ and Npu$_C^{HN}$-SK$^C$ and SK$^M$ intein segments were mixed in solution at a molar ratio of 2:1. Cleaving occurred at room temperature for the indicated number of hours at the indicated pH in the absence of zinc. The buffer used was 20 mM AMPD/PIPES, and 500 mM NaCl. These data show profoundly increased cleavage rate and pH sensitivity, especially for the native SK$^M$ target protein, relative to the initial inteins (FIG. 22A-B) or the inteins with only one of the two modifications (serine to histidine mutation or sensitivity-enhancing motif).

FIGS. 21A-B show cleaving kinetics on column for the C-terminal intein segment with a serine to histidine mutation ($Npu_c^{HN}$) and the target protein streptokinase ($SK^M$), and N-terminal intein segment with a sensitivity-enhancing motif ($Zn\text{-}Npu_N$). In this case, 400 µL of $Zn\text{-}Npu_N$ bound to the SulfoLink™ resin was used to purify $Npu_c^{HN}\text{-}SK^M$. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2 or 8.5. The intein cleaving reaction occurred at room temperature. Both 21A and 21B show purification by His tag at pH 8.5 (the leftmost lanes on each gel). The right lanes on each gel show the cleaving of the $Npu_N$ segment over time at either pH 8.5 (left gel) or pH 6.2 (right gel). These figures demonstrate that the cleavage of the purified protein is highly pH sensitive, with little or no cleavage observed at pH 8.5 and 5 hours incubation, while almost complete cleaveage is observed at pH 6.2 and 5 hours incubation.

FIGS. 22A-B show cleaving kinetics on column for of C-terminal intein segment with a serine to histidine mutation ($Npu_c^{HN}$) and the target protein rpoA-sfGFP, and N-terminal intein segment with a sensitivity-enhancing motif ($Zn\text{-}Npu_N$). In this case, 400 µL of $Zn\text{-}Npu_N$ bound to the SulfoLink™ resin was used to purify $Npu_c^{HN}$-rpoA-sfGFP. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2 or 8.5 (FIGS. 22A and 22B, respectively). The intein cleaving reaction occurred at room temperature. As with the purification shown in FIG. 21, the intein cleaving reaction is highly pH sensitive, with little or no cleaving taking place at pH 8.5 over the course of the experiment, while complete cleavage is observed at pH 6.2 and 16 hours incubation.

FIGS. 23A-D shows the cleaving kinetic studies of $Npu_N$ (C.F.) and Npuc-SKM (A), Npuc-SKC (B), NpucHN-$SK^M$ (C) and NpucHN-SKC (D). The $Npu_N$ and Npuc were pre-purified using Ni-NTA and then mixed in a 2:1 molar ratio. The cleaving reaction was carried out at room temperature over 16 hours under pH 8.5 or pH 6.2.

FIGS. 25A-D show the cleaving kinetic study of $Zn\text{-}Npu_N$ and $Npu_C$ mutants at different pH conditions. (A) The mixture of $Zn\text{-}Npu_N$ and $Npu_C$-SKM; (B) $Zn\text{-}Npu_N$ and $Npu_C$-SKC; (C) $Zn\text{-}Npu_N$ and $Npu_C^{HN}$-SKM; (D) $Zn\text{-}Npu_N$ and $Npu_C^{HN}$-SKC. The cleaving reaction was carried out at room temperature over 16 hours in solution. No $ZnCl_2$ was added to the system.

FIG. 26 shows the general structure and reaction scheme of using the SulfoLink Coupling Resin.

FIGS. 27A-B show CHO-IVT expressed recombinant protein purification using $Zn\text{-}Npu_N$ resin. (A) $Npu_c^{HN}$-SKM; (B) $Npu_c^{HN}$-sfGFP purification were controlled by pH. All cleaving reactions were carried out at room temperature for 5 hours. The samples were analyzed by silver staining gel.

FIGS. 30A-B show the mammalian cell expressed recombinant protein purification using $Zn\text{-}Npu_N$ under the control of pH. (A) expression in HEK293 and (B) in CHO-K1. Lane Exp: the expression sample collected from cell culture media; lane FT: column flow-through; lane W: the sample collected during wash step; lane 0 hr: The resin sample prior to intein cleavage; lane E: protein elution; The samples were analyzed using silver staining.

FIG. 31A shows the Western Blot result showing the purification process of NpucHN-SEAP using Zn-NpuN and 31B shows the digestion of the final purified SEAP with PNGaseF for examining the glycosylation. The Western Blot was detecting the target proteins using anti-His tag antibody, which targets a His tag engineered onto the C-terminus of the SEAP target for detection, conjugated with HRP reporter.

DESCRIPTION

Figure 1:
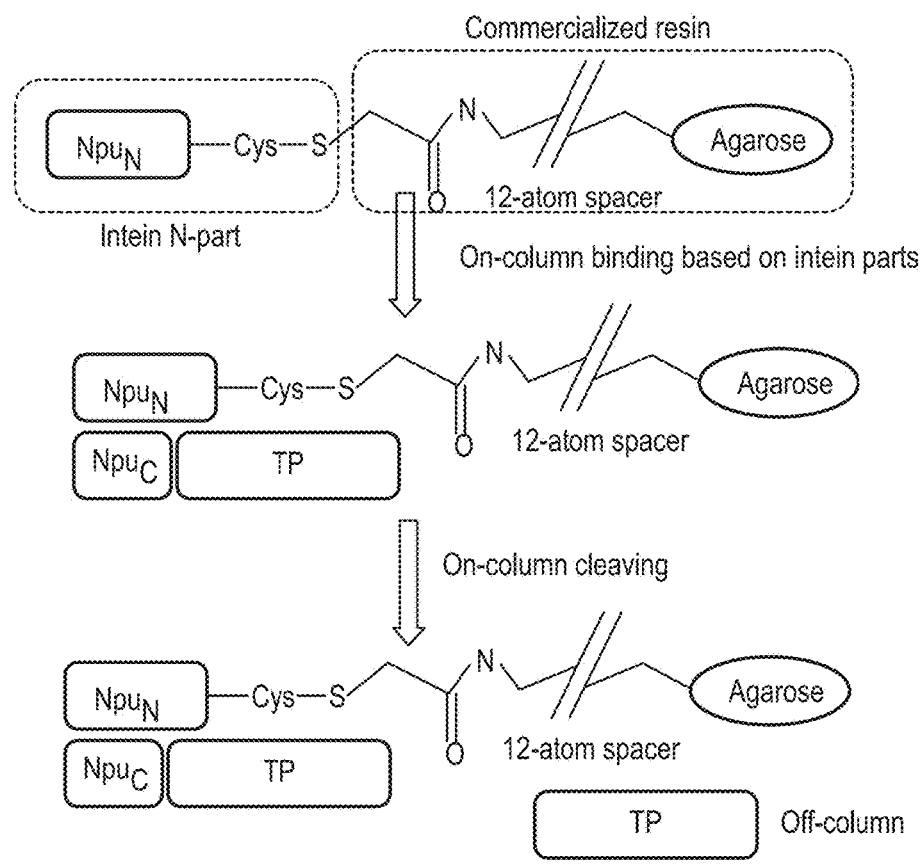
FIG. 1 shows a scheme of immobilization and purification. The N-terminal intein segment ($Npu_N$) is expressed and purified from a recombinant protein expression host (in this case bacteria), and then immobilized onto a commercially available immobilization resin (Commercialized resin) by following the manufacturer's protocol. In the examples shown throughout, the commercially available SulfoLink™ resin has been used, available from Thermo Fisher, although this example is not intended to be limiting to this specific chemistry. One skilled in the art could use a number of coupling chemistries to accomplish a similar $Npu_N$ immobilization using methods described in the literature. The charged resin can be directly used to capture the intein C-terminal intein segment ($Npu_C$), which has been fused to a Target Protein (TP), by the association between the N-terminal and C-terminal intein segments (On-column binding based on intein parts). After the contaminants have been washed away, the intein can be induced to release the target protein (TP) from the column matrix by a thio-reagent or a pH or temperature shift (On-column cleaving). The cleaved tag-free target can be directly collected from the column, and the column can be regenerated to remove the cleaved intein C segment from the column, allowing for multiple rounds of purification.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

The term "contacting" as used herein refers to bringing two biological entities together in such a manner that the compound can affect the activity of the target, either directly; i.e., by interacting with the target itself, or indirectly; i.e., by interacting with another molecule, co-factor, factor, or protein on which the activity of the target is dependent. "Contacting" can also mean facilitating the interaction of two biological entities, such as peptides, to bond covalently or otherwise.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "target protein", "protein of interest" and "therapeutic agent" include any synthetic or naturally occurring protein or peptide. The term therefore encompasses those compounds traditionally regarded as drugs, vaccines, and biopharmaceuticals including molecules such as proteins, peptides, and the like. Examples of therapeutic agents are described in well-known literature references such as the Merck Index (14th edition), the Physicians' Desk Reference (64th edition), and The Pharmacological Basis of Therapeutics (1st edition), and they include, without limitation, medicaments; substances used for the treatment, prevention, diagnosis, cure or mitigation of a disease or illness; substances that affect the structure or function of the body, or pro-drugs, which become biologically active or more active after they have been placed in a physiological environment.

As used herein, "variant" refers to a molecule that retains a biological activity that is the same or substantially similar to that of the original sequence. The variant may be from the same or different species or be a synthetic sequence based on a natural or prior molecule. Moreover, as used herein, "variant" refers to a molecule having a structure attained from the structure of a parent molecule (e.g., a protein or peptide disclosed herein) and whose structure or sequence is sufficiently similar to those disclosed herein that based upon that similarity, would be expected by one skilled in the art to exhibit the same or similar activities and utilities compared to the parent molecule. For example, substituting specific amino acids in a given peptide can yield a variant peptide with similar activity to the parent.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

In addition, as used herein, the term "peptide" refers to amino acids joined to each other by peptide bonds or modified peptide bonds, e.g., peptide isosteres, etc. and may contain modified amino acids other than the 20 gene-encoded amino acids. The peptides can be modified by either natural processes, such as post-translational processing, or by chemical modification techniques which are well known in the art. Modifications can occur anywhere in the peptide, including the peptide backbone, the amino acid side-chains and the amino or carboxyl termini. The same type of modification can be present in the same or varying degrees at several sites in a given polypeptide. Also, a given peptide can have many types of modifications. Modifications include, without limitation, linkage of distinct domains or motifs, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, "isolated peptide" or "purified peptide" is meant to mean a peptide (or a fragment thereof) that is substantially free from the materials with which the peptide is normally associated in nature, or from the materials with which the peptide is associated in an artificial expression or production system, including but not limited to an expression host cell lysate, growth medium components, buffer components, cell culture supernatant, or components of a synthetic in vitro translation system. The peptides disclosed herein, or fragments thereof, can be obtained, for example, by extraction from a natural source (for example, a mammalian cell), by expression of a recombinant nucleic acid encoding the peptide (for example, in a cell or in a cell-free translation system), or by chemically synthesizing the peptide. In addition, peptide fragments may be obtained by any of these methods, or by cleaving full length proteins and/or peptides.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequences. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or peptide molecules.

As used herein, "extein" refers to the portion of an intein-modified protein that is not part of the intein and which can be spliced or cleaved upon excision of the intein.

"Intein" refers to an in-frame intervening sequence in a protein. An intein can catalyze its own excision from the protein through a post-translational protein splicing process to yield the free intein and a mature protein. An intein can also catalyze the cleavage of the intein-extein bond at either the intein N-terminus, or the intein C-terminus, or both of the intein-extein termini. As used herein, "intein" encompasses mini-inteins, modified or mutated inteins, and split inteins.

A "split intein" is an intein that is comprised of two or more separate components not fused to one another. Split inteins can occur naturally, or can be engineered by splitting contiguous inteins.

As used herein, the term "splice" or "splices" means to excise a central portion of a polypeptide to form two or more smaller polypeptide molecules. In some cases, splicing also includes the step of fusing together two or more of the smaller polypeptides to form a new polypeptide. Splicing can also refer to the joining of two polypeptides encoded on two separate gene products through the action of a split intein.

As used herein, the term "cleave" or "cleaves" means to divide a single polypeptide to form two or more smaller polypeptide molecules. In some cases, cleavage is mediated by the addition of an extrinsic endopeptidase, which is often referred to as "proteolytic cleavage". In other cases, cleaving can be mediated by the intrinsic activity of one or both of the cleaved peptide sequences, which is often referred to as "self-cleavage". Cleavage can also refer to the self-cleavage of two polypeptides that is induced by the addition of a non-proteolytic third peptide, as in the action of split intein system described herein.

By the term "fused" is meant covalently bonded to. For example, a first peptide is fused to a second peptide when the two peptides are covalently bonded to each other (e.g., via a peptide bond).

As used herein an "isolated" or "substantially pure" substance is one that has been separated from components which naturally accompany it. Typically, a polypeptide is substantially pure when it is at least 50% (e.g., 60%, 70%, 80%, 90%, 95%, and 99%) by weight free from the other proteins and naturally-occurring organic molecules with which it is naturally associated.

Herein, "bind" or "binds" means that one molecule recognizes and adheres to another molecule in a sample, but does not substantially recognize or adhere to other molecules in the sample. One molecule "specifically binds" another molecule if it has a binding affinity greater than about $10^5$ to $10^6$ liters/mole for the other molecule.

Nucleic acids, nucleotide sequences, proteins or amino acid sequences referred to herein can be isolated, purified, synthesized chemically, or produced through recombinant DNA technology. All of these methods are well known in the art.

As used herein, the terms "modified" or "mutated," as in "modified intein" or "mutated intein," refer to one or more modifications in either the nucleic acid or amino acid sequence being referred to, such as an intein, when compared to the native, or naturally occurring structure. Such modification can be a substitution, addition, or deletion. The modification can occur in one or more amino acid residues or one or more nucleotides of the structure being referred to, such as an intein.

As used herein, the term "modified peptide", "modified protein" or "modified protein of interest" or "modified target protein" refers to a protein which has been modified.

As used herein, "operably linked" refers to the association of two or more biomolecules in a configuration relative to one another such that the normal function of the biomolecules can be performed. In relation to nucleotide sequences, "operably linked" refers to the association of two or more nucleic acid sequences, by means of enzymatic ligation or otherwise, in a configuration relative to one another such that the normal function of the sequences can be performed. For example, the nucleotide sequence encoding a pre-sequence or secretory leader is operably linked to a nucleotide sequence for a polypeptide if it is expressed as a pre-protein that participates in the secretion of the polypeptide; a promoter or enhancer is operably linked to a coding sequence if it affects the transcription of the coding sequence; and a ribosome binding site is operably linked to a coding sequence if it is positioned so as to facilitate translation of the sequence.

"Sequence homology" can refer to the situation where nucleic acid or protein sequences are similar because they have a common evolutionary origin. "Sequence homology" can indicate that sequences are very similar. Sequence similarity is observable; homology can be based on the observation. "Very similar" can mean at least 70% identity, homology or similarity; at least 75% identity, homology or similarity; at least 80% identity, homology or similarity; at least 85% identity, homology or similarity; at least 90% identity, homology or similarity; such as at least 93% or at least 95% or even at least 97% identity, homology or similarity. The nucleotide sequence similarity or homology or identity can be determined using the "Align" program of Myers et al. (1988) CABIOS 4:11-17 and available at NCBI. Additionally or alternatively, amino acid sequence similarity or identity or homology can be determined using the BlastP program (Altschul et al. Nucl. Acids Res. 25:3389-3402), and available at NCBI. Alternatively or additionally, the terms "similarity" or "identity" or "homology," for instance, with respect to a nucleotide sequence, are intended to indicate a quantitative measure of homology between two sequences.

Figure 2A:
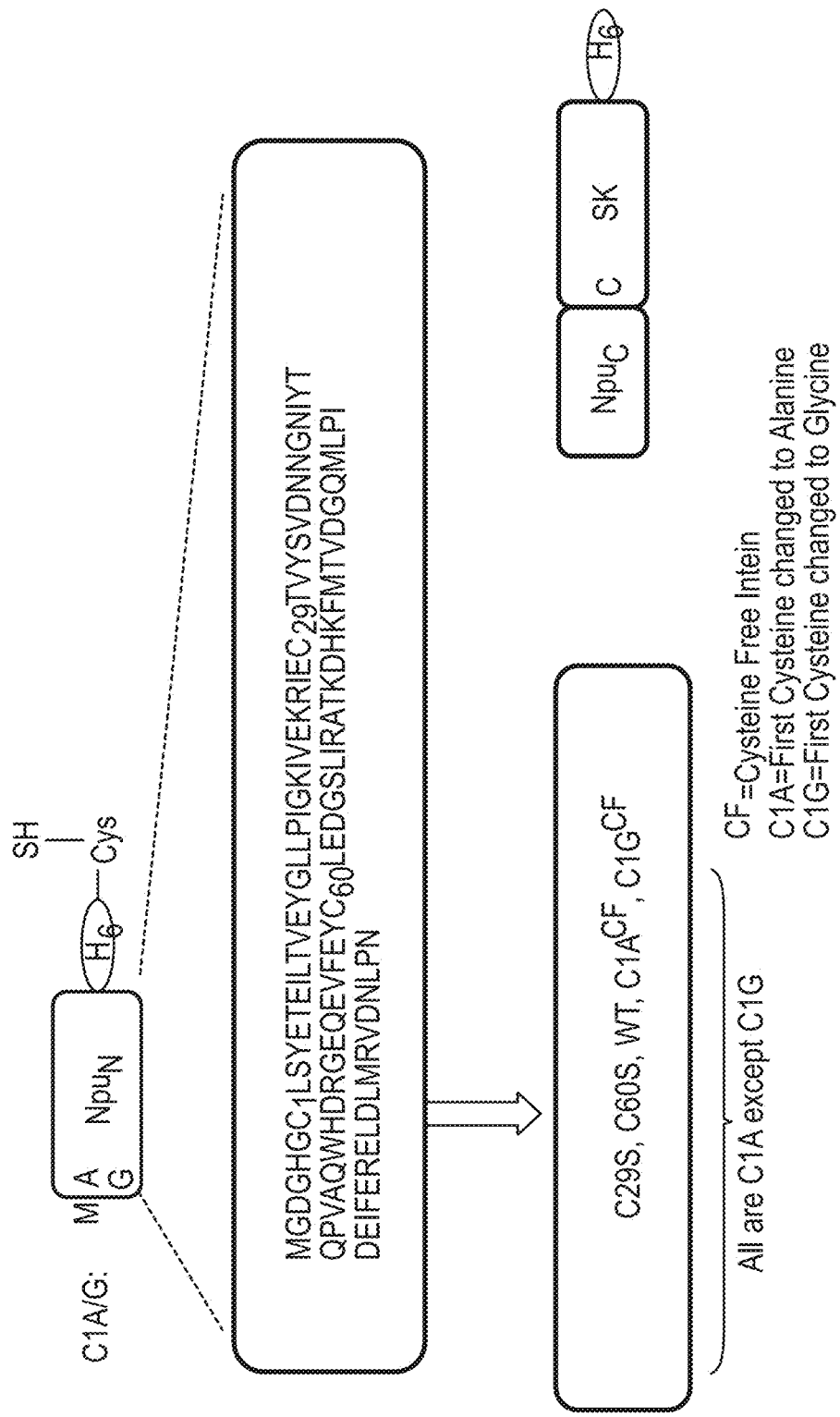
FIGS. 2A and 2B show the effects of cysteine mutations to serine in the intein N-terminal segment on its C-cleaving behavior. Two cysteines located on the intein N-part were separately mutated into serine (C29S, C60S) or both were mutated into serines (CF="Cysteine Free"). The CF intein was then combined with either a C1A mutation (initial Cysteine of the intein mutated to Alanine), or a C1G mutation (initial cysteine of the intein mutated to glycine), which is conventionally used to suppress intein splicing and deliver isolated cleaving as required for the purification method. These intein mutant proteins were then mixed with an intein C-terminal segment fusion protein ($Npu^{D-G}_C$-SKhis) to evaluate the C-terminal intein segment cleaving efficiency in the assembled intein. In this case, the C-terminal intein segment is fused to and cleaves to release the SKhis example target protein (streptokinase enzyme with a His tag label) from the C-terminal intein segment, which can be easily observed through the appearance of the cleaved SKhis band on an SDS-PAGE gel.

Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm. (1983) Proc. Natl. Acad. Sci. USA 80:726. For example, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence. The following references also provide algorithms for comparing the relative identity or homology or similarity of amino acid residues of two proteins, and additionally or alternatively with respect to the foregoing, the references can be used for determining percent homology or identity or similarity. Needleman et al. (1970) J. Mol. Biol. 48:444-453; Smith et al. (1983) Advances App. Math. 2:482-489; Smith et al. (1981) Nuc. Acids Res. 11:2205-2220; Feng et al. (1987) J. Molec. Evol. 25:351-360; Higgins et al. (1989) CABIOS 5:151-153; Thompson et al. (1994) Nuc. Acids Res. 22:4673-480; and Devereux et al. (1984) 12:387-395. "Stringent hybridization conditions" is a term which is well known in the art; see, for example, Sambrook, "Molecular Cloning, A Laboratory Manual" second ed., CSH Press, Cold Spring Harbor, 1989; "Nucleic Acid Hybridization, A Practical Approach", Hames and Higgins eds., IRL Press, Oxford, 1985; see also FIG. 2 and description thereof herein wherein there is a sequence comparison.

The terms "plasmid" and "vector" and "cassette" refer to an extrachromosomal element often carrying genes which are not part of the central metabolism of the cell and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Typically, a "vector" is a modified plasmid that contains additional multiple insertion sites for cloning and an "expression cassette" that contains a DNA sequence for a selected gene product (i.e., a transgene) for expression in the host cell. This "expression cassette" typically includes a 5' promoter region, the transgene ORF, and a 3' terminator region, with all necessary regulatory sequences required for transcription and translation of the ORF. Thus, integration of the expression cassette into the host permits expression of the transgene ORF in the cassette.

The term "buffer" or "buffered solution" refers to solutions which resist changes in pH by the action of its conjugate acid-base range.

The term "loading buffer" or "equilibrium buffer" refers to the buffer containing the salt or salts which is mixed with the protein preparation for loading the protein preparation onto a column. This buffer is also used to equilibrate the column before loading, and to wash to column after loading the protein.

The term "wash buffer" is used herein to refer to the buffer that is passed over a column (for example) following loading of a protein of interest (such as one coupled to a C-terminal intein fragment, for example) and prior to elution of the protein of interest. The wash buffer may serve to remove one or more contaminants without substantial elution of the desired protein.

The term "elution buffer" refers to the buffer used to elute the desired protein from the column. As used herein, the term "solution" refers to either a buffered or a non-buffered solution, including water.

The term "washing" means passing an appropriate buffer through or over a solid support, such as a chromatographic resin.

The term "eluting" a molecule (e.g. a desired protein or contaminant) from a solid support means removing the molecule from such material.

The term "contaminant" or "impurity" refers to any foreign or objectionable molecule, particularly a biological macromolecule such as a DNA, an RNA, or a protein, other than the protein being purified, that is present in a sample of a protein being purified. Contaminants include, for example, other proteins from cells that express and/or secrete the protein being purified.

The term "separate" or "isolate" as used in connection with protein purification refers to the separation of a desired protein from a second protein or other contaminant or mixture of impurities in a mixture comprising both the desired protein and a second protein or other contaminant or impurity mixture, such that at least the majority of the molecules of the desired protein are removed from that portion of the mixture that comprises at least the majority of the molecules of the second protein or other contaminant or mixture of impurities.

The term "purify" or "purifying" a desired protein from a composition or solution comprising the desired protein and one or more contaminants means increasing the degree of purity of the desired protein in the composition or solution by removing (completely or partially) at least one contaminant from the composition or solution.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result. For example, compounds used to control pH in the examples shown can be substituted with other buffering compounds to control pH, since pH is the critical variable to be controlled and the specific buffering compounds can vary.

B. Protein Purification Systems

Disclosed herein is a protein purification system, wherein the system comprises a split intein comprising two separate peptides: an N-terminal intein segment and a C-terminal intein segment, wherein the N-terminal intein segment can be linked to a solid support, and wherein the C-terminal intein segment DNA is genetically fused to a desired target protein DNA such that the expressed target protein is tagged with the C-terminal intein segment, and wherein cleaving of the C-terminal intein segment is suppressed in the absence of the N-terminal intein segment, and wherein the N-terminal intein segment and C-terminal intein segment associate strongly to form an immobilized complex when contacted to each other on the solid support, and wherein the C-terminal cleaving activity of the C-terminal intein segment in the assembled N-terminal and C-terminal intein segment complex is highly sensitive to extrinsic conditions when compared to a native intein complex, and wherein the immobilized intein complex with the fused target protein can be purified through washing away of unimmobilized contaminants, and wherein the C-terminal intein segment can be induced to cleave and thereby release the untagged and substantially purified target protein from the immobilized intein complex through a controlled change in extrinsic conditions. FIG. 1 shows an example of the split intein scheme.

Intein-based methods of protein modification and ligation have been developed. An intein is an internal protein sequence capable of catalyzing a protein splicing reaction that excises the intein sequence from a precursor protein and joins the flanking sequences (N- and C-exteins) with a peptide bond (Perler et al. (1994)). Hundreds of intein and intein-like sequences have been found in a wide variety of organisms and proteins (Perler et al. (2002); Liu et al. (2003)), they are typically 350-550 amino acids in size and also contain a homing endonuclease domain, but natural and engineered mini-inteins having only the ~140-aa splicing domain are sufficient for protein splicing (Liu et al. (2003); Yang et al. (2004); Telenti et al. (1997); Wu et al. (1998); Derbyshire et al. (1997)). The conserved crystal structure of mini-inteins (or the protein splicing domain) consists of ~12 beta-strands that form a disk-like structure with the two splicing junctions located in a central cleft (Duan et al. (1997); Ichiyanagi et al. (2000); Klabunde et al. (1998); Ding et al. (2003); Xu et al. (1996)).

As used herein, the term "split intein" refers to any intein in which one or more peptide bond breaks exists between the N-terminal intein segment and the C-terminal intein segment such that the N-terminal and C-terminal intein segments become separate molecules that can non-covalently reassociate, or reconstitute, into an intein that is functional for splicing or cleaving reactions. Any catalytically active intein, or fragment thereof, may be used to derive a split intein for use in the systems and methods disclosed herein. For example, in one aspect the split intein may be derived from a eukaryotic intein. In another aspect, the split intein may be derived from a bacterial intein. In another aspect, the split intein may be derived from an archaeal intein. Preferably, the split intein so-derived will possess only the amino acid sequences essential for catalyzing splicing reactions. Examples of inteins which can be used with the methods and systems disclosed herein can be found in Table 2.

As used herein, the "N-terminal intein segment" refers to any intein sequence that comprises an N-terminal amino acid sequence that is functional for splicing and/or cleaving reactions when combined with a corresponding C-terminal intein segment. An N-terminal intein segment thus also comprises a sequence that is spliced out when splicing occurs. An N-terminal intein segment can comprise a sequence that is a modification of the N-terminal portion of a naturally occurring (native) intein sequence. For example, an N-terminal intein segment can comprise additional amino acid residues and/or mutated residues so long as the inclusion of such additional and/or mutated residues does not render the intein non-functional for splicing or cleaving. Such modifications are discussed in more detail below. Preferably, the inclusion of the additional and/or mutated residues improves or enhances the splicing activity and/or controllability of the intein. Non-intein residues can also be genetically fused to intein segments to provide additional functionality, such as the ability to be affinity purified or to be covalently immobilized.

As used herein, the "C-terminal intein segment" refers to any intein sequence that comprises a C-terminal amino acid sequence that is functional for splicing or cleaving reactions when combined with a corresponding N-terminal intein segment. In one aspect, the C-terminal intein segment comprises a sequence that is spliced out when splicing occurs. In another aspect, the C-terminal intein segment is cleaved from a peptide sequence fused to its C-terminus. The sequence which is cleaved from the C-terminal intein's C-terminus is referred to herein as a "protein of interest" or "target protein" and is discussed in more detail below. A C-terminal intein segment can comprise a sequence that is a modification of the C-terminal portion of a naturally occurring (native) intein sequence. For example, a C terminal intein segment can comprise additional amino acid residues and/or mutated residues so long as the inclusion of such additional and/or mutated residues does not render the C-terminal intein segment non-functional for splicing or cleaving. Preferably, the inclusion of the additional and/or mutated residues improves or enhances the splicing and/or cleaving activity of the intein.

Split inteins have many practical uses including the production of recombinant proteins from fragments, the circularization of recombinant proteins, and the fixation of proteins on protein chips (Scott et al., (1999); Xu et al. (2001); Evans et al. (2000); Kwon et al., (2006)). Advantages of intein-based protein cleavage methods, compared to others such as protease-based methods, have been noted previously (Xu et al. (2001)). The intein-based N- and C-cleavage methods can also be used together on a single target protein to produce precise and tag-free ends at both the N- and the C-termini, or to achieve cyclization of the target protein (ligation of the N- and C-termini) using the expressed protein ligation approach.

The intein can be derived, for example, from an Npu DnaE intein, as shown in FIG. 1. $Npu_N$ refers to the N-terminal intein segment, while $Npu_C$ refers to the C-terminal intein segment. "TP" refers to the target protein (also referred to herein as the protein of interest), which can be coupled to $Npu_C$. In FIG. 1, a scheme is shown in which $Npu_N$ is coupled to a solid support, such as a commercialized resin. $Npu_C$, while attached to a target protein, is exposed to immobilized $Npu_N$. The $Npu_N$ and $Npu_C$ then associate, allowing purification of the fused target protein. When the proper conditions are present, a cleaving reaction can occur, which allows for cleaving (and subsequent elution) of the target protein from the immobilized intein segments.

Figure 7:
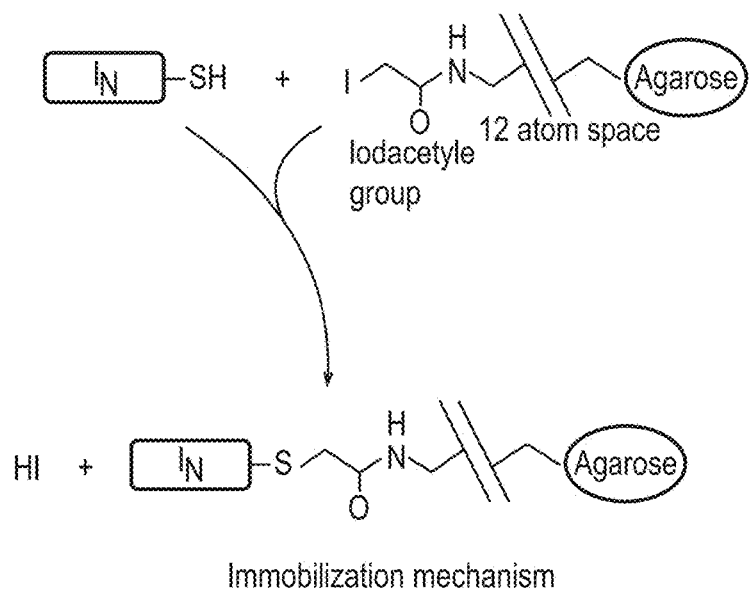
FIG. 7 shows an example covalent immobilization scheme for the N-terminal intein segment using the added cysteine residues at its N-terminus. This figure was taken from the manufacturer's instructions for the commercially available SulfoLink resin.

The N-terminal intein segment can be been modified from a native intein (such as Npu DnaE, for example) so that the N-terminal intein segment does not comprise any internal cysteine residues. This is desirous so as to eliminate side reactions associated with immobilization of the $Npu_N$ intein segment onto a solid support using the scheme shown in FIG. 7. Disclosed herein is an N-terminal intein segment in which one or more of the native cysteine residues have been mutated. For example, the residues can be mutated to serine. An example of $Npu_N$ in which the cysteine residues have been mutated can be found in SEQ ID NO: 2. It is noted that the first cysteine residue which is replaced (the first amino acid on the intein N-terminus) can be replaced with either alanine or glycine so as to eliminate intein splicing in the assembled intein complex. The $Npu_N$ intein can also be modified by the addition of an internal affinity tag to facilitate its purification, and addition of specific paptides to its C-terminus to facilitate covalent immobilization onto a solid support. For example, an included His tag was used to purify the $Npu_N$-segment described herein, while three Cys residues were appended to the C-terminus of $Npu_N$ to facilitate chemical immobilization of the $Npu_N$-segment. The modified $Npu_N$ segment that incorporates both the His tag and Cys residues is shown by way of example in SEQ ID NO: 3. Importantly, any tag can be used to purify the N-segment (not just His), and several different immobilization chemistries can be used to immobilize the N-segment. "Tags" are more generally referred to herein as purification tags. In one example, the N-segment could be purified without a tag, using conventional chromatography. Furthermore, it is also possible to add a His mutation in the C-terminal intein segment, and a "sensitivity enhancing domain" to the N-terminal intein segment.

The N-terminal intein segment can also comprise a purification, or affinity tag, attached to its C-terminus. This can include an affinity resin reagent. The purification tag can comprise, for example, one or more histidine residues. The purification tag can comprise, for example, a chitin binding domain protein with highly specific affinity for chitin. The purification tag can further comprise, for example, a reversibly precipitating elastin-like peptide tag, which can be induced to selectively precipitate under known conditions of buffer composition and temperature. Affinity tags are discussed in more detail below. The N-terminal intein segment can also comprise amino acids at its C-terminus which allow for covalent immobilization. For example, one or more amino acids at the C-terminus can be cysteine residues.

The N-terminal intein segment can be immobilized onto a solid support. A variety of supports can be used. For example, the solid support can a polymer or substance that allows for immobilization of the N-terminal intein fragment, which can occur covalently or via an affinity tag with or without an appropriate linker. When a linker is used, the linker can be additional amino acid residues engineered to the C-terminus of the N-terminal intein segment, or can be other known linkers for attachment of a peptide to a support.

The N-terminal intein segment disclosed herein can be attached to an affinity tag through a linker sequence. The linker sequence can be designed to create distance between the intein and affinity tag, while providing minimal steric interference to the intein cleaving active site. It is generally accepted that linkers involve a relatively unstructured amino acid sequence, and the design and use of linkers are common in the art of designing fusion peptides. There is a variety of protein linker databases which one of skill in the art will recognize. This includes those found in Argos et al. J Mol Biol 1990 Feb. 20; 211(4) 943-58; Crasto et al. Protein Eng 2000 May; 13(5) 309-12; George et al. Protein Eng 2002 November; 15(11) 871-9; Arai et al. Protein Eng 2001 August; 14(8) 529-32; and Robinson et al. PNAS May 26, 1998 vol. 95 no. 11 5929-5934, hereby incorporated by reference in their entirety for their teaching of examples of linkers.

Table 1 shows exemplary sequences of the N-terminal intein segment and the C-terminal intein segment:

| SEQ ID NO: 1 | NATIVE DNAE NPU N-TERMINAL INTEIN SEGMENT | CLSYETEILTVEYGLLPIGKIVEKRIECT VYSVDNNGNIYTQPVAQWHDRGEQEV FEYCLEDGSLIRATKDHKFMTVDGQML PIDEIFERELDLMRVDNLPN |
|---|---|---|
| SEQ ID NO: 2 | DNAE NPU N-TERMINAL INTEIN SEGMENT WITH CYSTEINES REPLACED ("X" REPRESENTS A OR G REPLACEMENT) | XLSYETEILTVEYGLLPIGKIVEKRIESTV YSVDNNGNIYTQPVAQWHDRGEQEVF EYSLEDGSLIRATKDHKFMTVDGQMLP IDEIFERELDLMRVDNLPN |
| SEQ ID NO: 3 | N-TERMINAL INTEIN SEGMENT WITH INTERNAL HIS TAG AND CYSTEINE RESIDUES AT THE C-TERMINUS | XLSYETEILTVEYGLLPIGKIVEKRIESTV YSVDNNGNIYTQPVAQWHDRGEQEVF EYSLEDGSLIRATKDHKFMTVDGQMLP IDEIFERELDLMRVDNLPNGGGGSHHH HHHCCC |
| SEQ ID NO: 4 | N-TERMINAL INTEIN SEGMENT WITH SENSITIVITY ENHANCING MOTIF ON THE N-TERMINUS | MGDGHGXLSYETEILTVEYGLLPIGKIV EKRIESTVYSVDNNGNIYTQPVAQWHD RGEQEVFEYSLEDGSLIRATKDHKFMT VDGQMLPIDEIFERELDLMRVDNLPN |
| SEQ ID NO: 5 | N-TERMINAL INTEIN SEGMENT WITH CYS REPLACEMENTS, SENSITIVITY ENHANCING MOTIF ON C-TERMINUS, AND HIS TAG AND CYSTEINE RESIDUES N-TERMINUS | MGDGHGXLSYETEILTVEYGLLPIGKIV EKRIESTVYSVDNNGNIYTQPVAQWHD RGEQEVFEYSLEDGSLIRATKDHKFMT VDGQMLPIDEIFERELDLMRVDNLPNG GGGSHHHHHHCCC |
| SEQ ID NO: 6 | N-TERMINAL INTEIN SEGMENT WITH A LINKER AND A CHITIN BINDING DOMAIN (CBD) AFFINITY TAG AT C-TERMINUS | MGDGHGALSYETEILTVEYGLLPIGKIV EKRIESTVYSVDNNGNIYTQPVAQWHD RGEQEVFEYSLEDGSLIRATKDHKFMT VDGQMLPIDEIFERELDLMRVDNLPNG GGGSGGGGSMTTNPGVSAWQVNTAYT AGQLVTYNGKTYKCLQPHTSLAGWEPS NVPALWQLQ |
| SEQ ID NO: 7 | N-TERMINAL INTEIN SEGMENT WITH AN ELASTIN-LIKE PROTEIN (ELP) TAG, A LINKER AND A SENSITIVITY ENHANCING MOTIF AT N-TERMINUS | MGHGVGVPGVGVPGGGVPGAGVPGV GVPGVGVPGVGVPGGGVPGAGVPGGG VPGVGVPGVGVPGGGVPGAGVPGVGV PGVGVPGVGVPGGGVPGAGVPGGGVP GVGVPGVGVPGGGVPGAGVPGVGVPG VGVPGVGVPGGGVPGAGVPGGGVPGV GVPGVGVPGGGVPGAGVPGVGVPGVG VPGVGVPGGGVPGAGVPGGGVPGVGV PGVGVPGGGVPGAGVPGVGVPGVGVP GVGVPGGGVPGAGVPGGGVPGVGVPG VGVPGGGVPGAGVPGVGVPGVGVPGV GVPGGGVPGAGVPGGGVPGVGVPGVG VPGGGVPGAGVPGVGVPGVGVPGVGV PGGGVPGAGVPGGGVPGVGVPGVGVP GGGVPGAGVPGVGVPGVGVPGVGVPG GGVPGAGVPGGGVPGVGVPGVGVPGG GVPGAGVPGVGVPGVGVPGVGVPGGG VPGAGVPGGGVPGVGVPGVGVPGGGV PGAGVPGVGVPGVGVPGVGVPGGGVP GAGVPGGGVPGVGVPGVGVPGGGVPG AGVPGVGVPGVGVPGVGVPGGGVPGA GVPGGGVPGGLVSSGI EGRISEFGDGHGALSYETEILTVEYGLLP IGKIVEKRIESTVYSVDNNGNIYTQPVA QWHDRGEQEVFEYSLEDGSLIRATKDH KFMTVDGQMLPIDEIFERELDLMRVDN LPN |
| SEQ ID NO: 8 | NATIVE DNAE NPU C-TERMINAL INTEIN SEGMENT (BUT WITH D TO G MUTATION INCLUDED IN ALL EXAMPLES HEREIN) | IKTATRKYLGKQNVYDIGVERDITNFAL KNGFIASN |
| SEQ ID NO: 9 | C-TERMINAL INTEIN SEGMENT WITH SERINE TO HISTIDINE REPLACEMENT AT POSITION 34 | IKIATRKYLGKQNVYGIGVERDHNFAL KNGFIAHN |
| SEQ ID NO: 10 | THE SEQUENCE OF SKC (+1C) | CIAGPEWLLDRPSVNNSQLVVSVAGTV EGTNQDISLKFFEIDLTSRPAHGGKTEQ GLSPKSKPFATDSGAMSHKLEKADLLK AIQEQLIANVHSNDDYFEVIDFASDATIT DRNGKVYFADKDGSVTLPTQPVQEFLL SGHVRVRPYKEKPIQNQAKSVDVEYTV QFTPLNPDDDFRPGLKDTKLLKTLAIGD TITSQELLAQAQSILNKNHPGYTIYERDS |

-continued

| | | |
|---|---|---|
| | | SIVTHDNDIFRTILPMDQEFTYRVKNRE<br>QAYRINKKSGLNEEINNTDLISEKYYVL<br>KKGEKPYDPFDRSHLKLFTIKYVDVDT<br>NELLKSEQLLTASERNLDFRDLYDPRD<br>KAKLLYNNLDAFGIMDYTLTGKVEDN<br>HDDTNRIITVYMGKRPEGENASYHLAY<br>DKDRYTEEEREVYSYLRYTGTPIPDNPN<br>DK |
| SEQ ID NO:<br>11 | THE SEQUENCE OF B-LAC (+1M) | MHPETLVKVKDAEDQLGARVGYIELDL<br>NSGKILESFRPEERFPMMSTFKVLLCGA<br>VLSRIDAGQEQLGRRIHYSQNDLVEYSP<br>VTEKHLTDGMTVRELCSAAITMSDNTA<br>ANLLLTTIGGPKELTAFLHNMGDHVTR<br>LDRWEPELNEAIPNDERDTTMPVAMAT<br>TLRKLLTGELLTLASRQQLIDWMEADK<br>VAGPLLRSALPAGWFIADKSGAGERGS<br>RGIIAALGPDGKPSRIVVIYTTGSQATM<br>DERNRQIAEIGASLIKHW |
| SEQ ID NO:<br>12 | THE SEQUENCE OF eGFP (+1C) | CFNVSKGEELFTGVVPILVELDGDVNG<br>HKFSVSGEGEGDATYGKLTLKFICTTGK<br>LPVPWPTLVTTLTYGVQCFSRYPDHMK<br>QHDFFKSAMPEGYVQERTIFFKDDGNY<br>KTRAEVKFEGDTLVNRIELKGIDFKEDG<br>NILGHKLEYNYNSHNVYIIVIADKQKNGI<br>KVNFKIRHNIEDGSVQLADHYQQNTPIG<br>DGPVLLPDNHYLSTQSALSKDPNEKRD<br>HMVLLEFVTAAGITLGMDELYK |
| SEQ ID NO:<br>13 | THE SEQUENCE OF MBP (+1M) | MKIEEGKLVIWINGDKGYNGLAEVGKK<br>FEKDTGIKVTVEHPDKLEEKFPQVAAT<br>GDGPDIIFWAHDRFGGYAQSGLLAEITP<br>DKAFQDKLYPFTWDAVRYNGKLIAYPI<br>AVEALSLIYNKDLLPNPPKTWEEIPALD<br>KELKAKGKSALMFNLQEPYFTWPLIAA<br>DGGYAFKYENGKYDIKDVGVDNAGAK<br>AGLTFLVDLIKNKHMNADTDYSIAEAA<br>FNKGETAMTINGPWAWSNIDTSKVNYG<br>VTVLPTFKGQPSKPFVGVLSAGINAASP<br>NKELAKEFLENYLLTDEGLEAVNKDKP<br>LGAVALKSYEEELAKDPRIAATMENAQ<br>KGEIMPNIPQMSAFWYAVRTAVINAAS<br>GRQTVDEALKDAQTNSSS |

Examples of linkers include, but are not limited to: (1) poly-asparagine linker consisting of 4 to 15 asparagine residues, and (2) glycine-serine linker, consisting of various combinations and lengths of polypeptides consisting of glycine and serine. One of skill in the art can easily identify and use any linker that will successfully link the CIPS with an affinity tag.

In one example, the solid support can be a solid chromatographic resin backbone, such as a crosslinked agarose. The term "solid support matrix" or "solid matrix" refers to the solid backbone material of the resin which material contains reactive functionality permitting the covalent attachment of ligand (such as N-terminal intein segments) thereto. The backbone material can be inorganic (e.g., silica) or organic. When the backbone material is organic, it is preferably a solid polymer and suitable organic polymers are well known in the art. Solid support matrices suitable for use in the resins described herein include, by way of example, cellulose, regenerated cellulose, agarose, silica, coated silica, dextran, polymers (such as polyacrylates, polystyrene, polyacrylamide, polymethacrylamide including commercially available polymers such as Fractogel, Enzacryl, and Azlactone), copolymers (such as copolymers of styrene and divinyl-benzene), mixtures thereof and the like. Also, co-, ter- and higher polymers can be used provided that at least one of the monomers contains or can be derivatized to contain a reactive functionality in the resulting polymer. In an additional embodiment, the solid support matrix can contain ionizable functionality incorporated into the backbone thereof.

Reactive functionalities of the solid support matrix permitting covalent attachment of the N-terminal intein segments are well known in the art. Such groups include hydroxyl (e.g., Si—OH), carboxyl, thiol, amino, and the like. Conventional chemistry permits use of these functional groups to covalently attach ligands, such as N-terminal intein segments, thereto. Additionally, conventional chemistry permits the inclusion of such groups on the solid support matrix. For example, carboxy groups can be incorporated directly by employing acrylic acid or an ester thereof in the polymerization process. Upon polymerization, carboxyl groups are present if acrylic acid is employed or the polymer can be derivatized to contain carboxyl groups if an acrylate ester is employed.

Affinity tags can be peptide or protein sequences cloned in frame with protein coding sequences that change the protein's behavior. Affinity tags can be appended to the N- or C-terminus of proteins which can be used in methods of purifying a protein from cells. Cells expressing a peptide comprising an affinity tag can be pelleted, lysed, and the cell lysate applied to a column, resin or other solid support that displays a ligand to the affinity tags. The affinity tag and any fused peptides are bound to the solid support, which can also be washed several times with buffer to eliminate unbound (contaminant) proteins. A protein of interest, if attached to an affinity tag, can be eluted from the solid support via a buffer that causes the affinity tag to dissociate from the ligand resulting in a purified protein, or can be cleaved from the bound affinity tag using a soluble protease. As disclosed herein, the affinity tag is cleaved through the self-cleaving action of the Npuc intein segment in the active intein complex.

Examples of affinity tags can be found in Kimple et al. Curr Protoc Protein Sci 2004 September; Arnau et al. Protein Expr Purif 2006 July; 48(1) 1-13; Azarkan et al. J Chromatogr B Analyt Technol Biomed Life Sci 2007 Apr. 15; 849(1-2) 81-90; and Waugh et al. Trends Biotechnol 2005 June; 23(6) 316-20, all hereby incorporated by reference in their entirety for their teaching of examples of affinity tags.

Examples of affinity include, but are not limited to, maltose binding protein, which can bind to immobilized maltose to facilitate purification of the fused target protein; Chitin binding protein, which can bind to immobilized chitin; Glutathione S transferase, which can bind to immobilized chitin; Poly-histidine, which can bind to immobilized chelated metals; FLAG octapeptide, which can bind to immobilized anti-FLAG antibodies.

Affinity tags can also be used to facilitate the purification of a protein of interest using the disclosed modified peptides through a variety of methods, including, but not limited to, selective precipitation, ion exchange chromatography, binding to precipitation-capable ligands, dialysis (by changing the size and/or charge of the target protein) and other highly selective separation methods.

In some aspects, affinity tags can be used that do not actually bind to a ligand, but instead either selectively precipitate or act as ligands for immobilized corresponding binding domains. In these instances, the tags are more generally referred to as purification tags. For example, the ELP tag selectively precipitates under specific salt and temperature conditions, allowing fused peptides to be purified by centrifugation. Another example is the antibody Fc domain, which serves as a ligand for immobilized protein A or Protein G-binding domains.

As disclosed herein, a protein of interest (POI), or target protein can attached to the C-terminal intein segment at its C-terminus. The C-terminal segment can be genetically fused to the protein of interest, for example. Methods of recombinant protein production are known to those of skill in the art. The C-terminal intein segment can comprise modifications when compared to a native Npu DnaE C-terminal intein segment. An example of such a modification includes, but is not limited to, a mutation of a highly conserved serine residue to a histidine residue. An example of such a mutation can be found in SEQ ID NO: 9, which also includes a mutation of a highly conserved aspartic acid to glycine. By "highly conserved" is meant identical amino acids or sequences that occur within aligned protein sequences across species.

The N-terminal intein segment can further comprise a sensitivity-enhancing motif (SEM), which renders the splicing or cleaving activity of the assembled intein complex highly sensitive to extrinsic conditions. This sensitivity-enhancing motif can render the split intein, when assembled (meaning the C-terminal intein segment comprising the protein of interest and the N-terminal intein segment are non-covalently associated, or covalently linked), more likely to cleave under certain conditions. Therefore, the sensitivity-enhancing motif can render the split intein more sensitive to extrinsic conditions when compared to a native, or naturally occurring, intein. For example, the split intein disclosed herein can be 5, 10, 15, 20, 25, 30, 35, 40, 45, 50, 55, 60, 65, 70, 75, 80, 85, 90, 95, or 100% or more sensitive to extrinsic conditions when compared to a native intein, where the sensitivity is defined as the percent cleavage under non-permissive conditions subtracted from the percent cleavage under permissive conditions. For example, if an intein shows no cleavage at pH 8.5 and 5 hours incubation, but 100% cleavage at pH 6.2 and 5 hours incubation, then the intein would show 100% sensitivity to this pH change under these conditions. Specifically, the Npu DnaE mutated intein disclosed herein (in SEQ ID NOS: 5, for example) can be more sensitive, and thus more likely to cleave the protein of interest, when certain conditions are present. These extrinsic conditions can be, for example, pH, temperature, or exposure to a certain compound or element, such as a chelating agent. Cleaving can occur at a greater rate, for example, at a pH of 6.2, when the sensitivity enhancing motif is present on the N-terminal intein segment, as compared to either an N-terminal intein segment which doesn't comprise the sensitivity enhancing motif, or a native or naturally occurring N-terminal intein segment. In another example, sensitivity can occur at a temperature of 0° C. to 45° C., when the sensitivity enhancing motif is present on the N-terminal intein segment, as compared to either an N-terminal intein segment which doesn't comprise the sensitivity enhancing motif, or a native or naturally occurring N-terminal intein segment.

The sensitivity enhancing motif (SEM) can be on the N-terminus of the N-terminal intein segment, for example. The SEM can be reversible. By "reversible" it is meant that the cleaving behavior of the split intein can be altered under a given extrinsic condition. This behavior of the intein, however, is reversible when the extrinsic condition is removed. For example, an intein may cleave or splice when at a pH of 6.2, but may not cleave or splice at a pH of 8.5. The SEMs disclosed herein can be designed such that when appended to, for example, the N-terminus of the N-terminal intein segment, they introduce a sensitivity enhancing element that allows for more precise control of cleavage of the protein of interest. This sensitivity has enabled the successful use of the inteins under conditions that are compatible with commercially relevant cell culture expression platforms.

In one example, a SEM can comprise the structure: aa1-aa2-aa3-aa4, wherein aa1 is a non-polar amino acid, aa2 is a negatively-charged amino acid, aa3 is a non-polar amino acid and aa4 is a positively charged amino acid. For example, aa1 can be glycine, alanine, isoleucine, leucine, methionine, phenylalanine, proline, tryptophan, or valine; aa2 can be aspartic acid or glutamic acid; aa3 can be glycine, alanine, isoleucine, leucine, methionine, phenylalanine, proline, tryptophan, or valine; and aa4 can be arginine or lysine.

Also disclosed herein is a SEM, wherein the SEM comprises the structure:aa1-aa2-aa3-aa4-aa5, wherein aa1 is a non-polar amino acid, aa2 is a negatively-charged amino acid, aa3 is a non-polar amino acid, aa4 is a positively charged amino acid and aa5 is a non-polar amino acid. For example, aa1 can be glycine, alanine, isoleucine, leucine, methionine, phenylalanine, proline, tryptophan, or valine; aa2 can be aspartic acid or glutamic acid or cysteine; aa3 can be glycine, alanine, isoleucine, leucine, methionine, phenylalanine, proline, tryptophan, or valine; aa4 can be arginine or lysine; and aa5 can be glycine, alanine, isoleucine, leucine, methionine, phenylalanine, proline, tryptophan, or valine.

Disclosed herein are SEMS, wherein the reversible SEM comprises the sequence G-E-G-H-H (SEQ ID NO: 14), G-E-G-H-G (SEQ ID NO: 15), G-D-G-H-H (SEQ ID NO:

16), or G-D-G-H-G (SEQ ID NO: 17). Also disclosed are SEQ ID NOS: 4-5, which is an N-terminal fusion segment comprising the above SEMs.

Disclosed herein is a method of purifying a protein of interest, the method comprising: utilizing a split intein comprising two separate peptides: an N-terminal intein segment and a C-terminal intein segment; immobilizing the N-terminal intein segment to a solid support; attaching a protein of interest to the C-terminal intein segment, wherein cleaving of the C-terminal intein segment is highly sensitive to extrinsic conditions when compared to a native intein; exposing the N-terminal intein segment and the C-terminal intein segment to each other so that they associate; washing the solid support to remove non-bound material; placing the associated the N-terminal intein segment and the C-terminal intein segment under conditions that allow for the intein to self-cleave; and isolating the protein of interest.

A database of inteins can be found at http://www.inteins.com. This database also includes split inteins. A list of inteins is found below in Table 2. All inteins have the potential to be made into split inteins, while some inteins naturally exist in a split form. All of the inteins found in Table 2 either exist as split inteins, or have the potential to be made into split inteins.

TABLE 2

| Naturally Occurring Inteins | | |
|---|---|---|
| Intein Name | Organism Name | Organism Description |
| Eucarya | | |
| APMV Pol | *Acanthomoeba polyphaga* Mimivirus | isolate = "Rowbotham-Bradford", Virus, infects Amoebae, taxon: 212035 |
| Abr PRP8 | *Aspergillus brevipes* FRR2439 | Fungi, ATCC 16899, taxon: 75551 |
| Aca-G186AR PRP8 | *Ajellomyces capsulatus* G186AR | Taxon: 447093, strain G186AR |
| Aca-H143 PRP8 | *Ajellomyces capsulatus* H143 | Taxon: 544712 |
| Aca-JER2004 PRP8 | *Ajellomyces capsulatus* (anamorph: *Histoplasma capsulatum*) | strain = JER2004, taxon: 5037, Fungi |
| Aca-NAm1 PRP8 | *Ajellomyces capsulatus* NAm1 | strain = "NAm1", taxon: 339724 |
| Ade-ER3 PRP8 | *Ajellomyces dermatitidis* ER-3 | Human fungal pathogen. taxon: 559297 |
| Ade-SLH14081 PRP8 | *Ajellomyces dermatitidis* SLH14081, | Human fungal pathogen |
| Afu-Af293 PRP8 | *Aspergillus fumigatus* var. *ellipticus*, strain Af293 | Human pathogenic fungus, taxon: 330879 |
| Afu-FRR0163 PRP8 | *Aspergillus fumigatus* strain FRR0163 | Human pathogenic fungus, taxon: 5085 |
| Afu-NRRL5109 PRP8 | *Aspergillus fumigatus* var. *ellipticus*, strain NRRL 5109 | Human pathogenic fungus, taxon: 41121 |
| Agi-NRRL6136 PRP8 | *Aspergillus giganteus* Strain NRRL 6136 | Fungus, taxon: 5060 |
| Ani-FGSCA4 PRP8 | *Aspergillus nidulans* FGSC A | Filamentous fungus, taxon: 227321 |
| Avi PRP8 | *Aspergillus viridinutans* strain FRR0577 | Fungi, ATCC 16902, taxon: 75553 |
| Bci PRP8 | *Botrytis cinerea* (teleomorph of *Botryotinia fuckeliana* B05.10) | Plant fungal pathogen |
| Bde-JEL197 RPB2 | *Batrachochytrium dendrobatidis* JEL197 | Chytrid fungus, isolate = "AFTOL-ID 21", taxon: 109871 |
| Bde-JEL423 PRP8-1 | *Batrachochytrium dendrobatidis* JEL423 | Chytrid fungus, isolate JEL423, taxon 403673 |
| Bde-JEL423 PRP8-2 | *Batrachochytrium dendrobatidis* JEL423 | Chytrid fungus, isolate JEL423, taxon 403673 |
| Bde-JEL423 RPC2 | *Batrachochytrium dendrobatidis* JEL423 | Chytrid fungus, isolate JEL423, taxon 403673 |
| Bde-JEL423 eIF-5B | *Batrachochytrium dendrobatidis* JEL423 | Chytrid fungus, isolate JEL423, taxon 403673 |
| Bfu-B05 PRP8 | *Botryotinia fuckeliana* B05.10 | Taxon: 332648 |
| CIV RIR1 | Chilo iridescent virus | dsDNA eucaryotic virus, taxon: 10488 |
| CV-NY2A ORF212392 | *Chlorella* virus NY2A infects *Chlorella* NC64A, which infects *Paramecium bursaria* | dsDNA eucaryotic virus, taxon: 46021, Family Phycodnaviridae |
| CV-NY2A RIR1 | *Chlorella* virus NY2A infects *Chlorella* NC64A, which infects *Paramecium bursaria* | dsDNA eucaryotic virus, taxon: 46021, Family Phycodnaviridae |
| CZIV RIR1 | *Costelytra zealandica* iridescent virus | dsDNA eucaryotic virus, Taxon: 68348 |
| Cba-WM02.98 PRP8 | *Cryptococcus bacillisporus* strain WM02.98 (aka *Cryptococcus neoformans gattii*) | Yeast, human pathogen, taxon: 37769 |
| Cba-WM728 PRP8 | *Cryptococcus bacillisporus* strain WM728 | Yeast, human pathogen, taxon: 37769 |
| Ceu ClpP | *Chlamydomonas eugametos* (chloroplast) | Green alga, taxon: 3053 |

TABLE 2-continued

Naturally Occurring Inteins

| Intein Name | Organism Name | Organism Description |
|---|---|---|
| Cga PRP8 | *Cryptococcus gattii* (aka *Cryptococcus bacillisporus*) | Yeast, human pathogen |
| Cgl VMA | *Candida glabrata* | Yeast, taxon: 5478 |
| Cla PRP8 | *Cryptococcus laurentii* strain CBS139 | Fungi, Basidiomycete yeast, taxon: 5418 |
| Cmo ClpP | *Chlamydomonas moewusii*, strain UTEX 97 | Green alga, chloroplast gene, taxon: 3054 |
| Cmo RPB2 (RpoBb) | *Chlamydomonas moewusii*, strain UTEX 97 | Green alga, chloroplast gene, taxon: 3054 |
| Cne-A PRP8 (Fne-A PRP8) | *Filobasidiella neoformans* (*Cryptococcus neoformans*) Serotype A, PHLS_8104 | Yeast, human pathogen |
| Cne-AD PRP8 (Fne-AD PRP8) | *Cryptococcus neoformans* (*Filobasidiella neoformans*), Serotype AD, CBS132). | Yeast, human pathogen, ATCC32045, taxon: 5207 |
| Cne-JEC21 PRP8 | *Cryptococcus neoformans* var. *neoformans* JEC21 | Yeast, human pathogen, serotype = "D" taxon: 214684 |
| Cpa ThrRS | *Candida parapsilosis*, strain CLIB214 | Yeast, Fungus, taxon: 5480 |
| Cre RPB2 | *Chlamydomonas reinhardtii* (nucleus) | Green algae, taxon: 3055 |
| CroV Pol | *Cafeteria roenbergensis* virus BV-PW1 | taxon: 693272, Giant virus infecting marine heterotrophic nanoflagellate |
| CroV RIR1 | *Cafeteria roenbergensis* virus BV-PW1 | taxon: 693272, Giant virus infecting marine heterotrophic nanoflagellate |
| CroV RPB2 | *Cafeteria roenbergensis* virus BV-PW1 | taxon: 693272, Giant virus infecting marine heterotrophic nanoflagellate |
| CroV Top2 | *Cafeteria roenbergensis* virus BV-PW1 | taxon: 693272, Giant virus infecting marine heterotrophic nanoflagellate |
| Cst RPB2 | *Coelomomyces stegomyiae* | Chytrid fungus, isolate = "AFTOL-ID 18", taxon: 143960 |
| Ctr ThrRS | *Candida tropicalis* ATCC750 | Yeast |
| Ctr VMA | *Candida tropicalis* (nucleus) | Yeast |
| Ctr-MYA3404 VMA | *Candida tropicalis* MYA-3404 | Taxon: 294747 |
| Ddi RPC2 | *Dictyostelium discoideum* strain AX4 (nucleus) | Mycetozoa (a social amoeba) |
| Dhan GLT1 | *Debaryomyces hansenii* CBS767 | Fungi, Anamorph: *Candida famata*, taxon: 4959 |
| Dhan VMA | *Debaryomyces hansenii* CBS767 | Fungi, taxon: 284592 |
| Eni PRP8 | *Emericella nidulans* R20 (anamorph: *Aspergillus nidulans*) | taxon: 162425 |
| Eni-FGSCA4 PRP8 | *Emericella nidulans* (anamorph: *Aspergillus nidulans*) FGSC A4 | Filamentous fungus, taxon: 162425 |
| Fte RPB2 (RpoB) | *Floydiella terrestris*, strain UTEX 1709 | Green alga, chloroplast gene, taxon: 51328 |
| Gth DnaB | *Guillardia theta* (plastid) | Cryptophyte Algae |
| HaV01 Pol | *Heterosigma akashiwo* virus 01 | Algal virus, taxon: 97195, strain HaV01 |
| Hca PRP8 | *Histoplasma capsulatum* (anamorph: *Ajellomyces capsulatus*) | Fungi, human pathogen |
| IIV6 RIR1 | Invertebrate iridescent virus 6 | dsDNA eucaryotic virus, taxon: 176652 |
| Kex-CBS379 VMA | *Kazachstania exigua*, formerly *Saccharomyces exiguus*, strain CBS379 | Yeast, taxon: 34358 |
| Kla-CBS683 VMA | *Kluyveromyces lactis*, strain CBS683 | Yeast, taxon: 28985 |
| Kla-IFO1267 VMA | *Kluyveromyces lactis* IFO1267 | Fungi, taxon: 28985 |
| Kla-NRRLY1140 VMA | *Kluyveromyces lactis* NRRL Y-1140 | Fungi, taxon: 284590 |
| Lel VMA | *Lodderomyces elongisporus* | Yeast |
| Mca-CBS113480 PRP8 | *Microsporum canis* CBS 113480 | Taxon: 554155 |
| Nau PRP8 | *Neosartorya aurata* NRRL 4378 | Fungus, taxon: 41051 |
| Nfe-NRRL5534 PRP8 | *Neosartorya fennelliae* NRRL 5534 | Fungus, taxon: 41048 |
| Nfi PRP8 | *Neosartorya fischeri* | Fungi |
| Ngl-FR2163 PRP8 | *Neosartorya glabra* FRR2163 | Fungi, ATCC 16909, taxon: 41049 |
| Ngl-FRR1833 PRP8 | *Neosartorya glabra* FRR1833 | Fungi, taxon: 41049, (preliminary identification) |
| Nqu PRP8 | *Neosartorya quadricincta*, strain NRRL 4175 | taxon: 41053 |
| Nspi PRP8 | *Neosartorya spinosa* FRR4595 | Fungi, taxon: 36631 |
| Pabr-Pb01 PRP8 | *Paracoccidioides brasiliensis* Pb01 | Taxon: 502779 |

TABLE 2-continued

Naturally Occurring Inteins

| Intein Name | Organism Name | Organism Description |
|---|---|---|
| Pabr-Pb03 PRP8 | *Paracoccidioides brasiliensis* Pb03 | Taxon: 482561 |
| Pan CHS2 | *Podospora anserina* | Fungi, Taxon 5145 |
| Pan GLT1 | *Podospora anserina* | Fungi, Taxon 5145 |
| Pbl PRP8-a | *Phycomyces blakesleeanus* | Zygomycete fungus, strain NRRL155 |
| Pbl PRP8-b | *Phycomyces blakesleeanus* | Zygomycete fungus, strain NRRL155 |
| Pbr-Pb18 PRP8 | *Paracoccidioides brasiliensis* Pb18 | Fungi, taxon: 121759 |
| Pch PRP8 | *Penicillium chrysogenum* | Fungus, taxon: 5076 |
| Pex PRP8 | *Penicillium expansum* | Fungus, taxon27334 |
| Pgu GLT1 | *Pichia (Candida) guilliermondii* | Fungi, Taxon 294746 |
| Pgu-alt GLT1 | *Pichia (Candida) guilliermondii* | Fungi |
| Pno GLT1 | *Phaeosphaeria nodorum* SN15 | Fungi, taxon: 321614 |
| Pno RPA2 | *Phaeosphaeria nodorum* SN15 | Fungi, taxon: 321614 |
| Ppu DnaB | *Porphyra purpurea* (chloroplast) | Red Alga |
| Pst VMA | *Pichia stipitis* CBS 6054, taxon: 322104 | Yeast |
| Ptr PRP8 | *Pyrenophora tritici-repentis* Pt-1C-BF | Ascomycete fungus, taxon: 426418 |
| Pvu PRP8 | *Penicillium vulpinum* (formerly *P. claviforme*) | Fungus |
| Pye DnaB | *Porphyra yezoensis* chloroplast, cultivar U-51 | Red alga, organelle = "plastid: chloroplast", "taxon: 2788 |
| Sas RPB2 | *Spiromyces aspiralis* NRRL 22631 | Zygomycete fungus, isolate = "AFTOL-ID 185", taxon: 68401 |
| Sca-CBS4309 VMA | *Saccharomyces castellii*, strain CBS4309 | Yeast, taxon: 27288 |
| Sca-IFO1992 VMA | *Saccharomyces castellii*, strain IFO1992 | Yeast, taxon: 27288 |
| Scar VMA | *Saccharomyces cariocanus*, strain = "UFRJ 50791 | Yeast, taxon: 114526 |
| Sce VMA | *Saccharomyces cerevisiae* (nucleus) | Yeast, also in Sce strains OUT7163, OUT7045, OUT7163, IFO1992 |
| Sce-DH1-1A VMA | *Saccharomyces cerevisiae* strain DH1-1A | Yeast, taxon: 173900, also in Sce strains OUT7900, OUT7903, OUT7112 |
| Sce-JAY291 VMA | *Saccharomyces cerevisiae* JAY291 | Taxon: 574961 |
| Sce-OUT7091 VMA | *Saccharomyces cerevisiae* OUT7091 | Yeast, taxon: 4932, also in Sce strains OUT7043, OUT7064 |
| Sce-OUT7112 VMA | *Saccharomyces cerevisiae* OUT7112 | Yeast, taxon: 4932, also in Sce strains OUT7900, OUT7903 |
| Sce-YJM789 VMA | *Saccharomyces cerevisiae* strain YJM789 | Yeast, taxon: 307796 |
| Sda VMA | *Saccharomyces dairenensis*, strain CBS 421 | Yeast, taxon: 27289, Also in Sda strain IFO0211 |
| Sex-IFO1128 VMA | *Saccharomyces exiguus*, strain = "IFO1128" | Yeast, taxon: 34358 |
| She RPB2 (RpoB) | *Stigeoclonium helveticum*, strain UTEX 441 | Green alga, chloroplast gene, taxon: 55999 |
| Sja VMA | *Schizosaccharomyces japonicus* yFS275 | Ascomycete fungus, taxon: 402676 |
| Spa VMA | *Saccharomyces pastorianus* IFO11023 | Yeast, taxon: 27292 |
| Spu PRP8 | *Spizellomyces punctatus* | Chytrid fungus, |
| Sun VMA | *Saccharomyces unisporus*, strain CBS 398 | Yeast, taxon: 27294 |
| Tgl VMA | *Torulaspora globosa*, strain CBS 764 | Yeast, taxon: 48254 |
| Tpr VMA | *Torulaspora pretoriensis*, strain CBS 5080 | Yeast, taxon: 35629 |
| Ure-1704 PRP8 | *Uncinocarpus reesii* | Filamentous fungus |
| Vpo VMA | *Vanderwaltozyma polyspora*, formerly *Kluyveromyces polysporus*, strain CBS 2163 | Yeast, taxon: 36033 |
| WIV RIR1 | *Wiseana* iridescent virus | dsDNA eucaryotic virus, taxon: 68347 |
| Zba VMA | *Zygosaccharomyces bailii*, strain CBS 685 | Yeast, taxon: 4954 |
| Zbi VMA | *Zygosaccharomyces bisporus*, strain CBS 702 | Yeast, taxon: 4957 |
| Zro VMA | *Zygosaccharomyces rouxii*, strain CBS 688 | Yeast, taxon: 4956 |

TABLE 2-continued

Naturally Occurring Inteins

| Intein Name | Organism Name | Organism Description |
|---|---|---|
| | Eubacteria | |
| AP-APSE1 dpol | *Acyrthosiphon pisum* secondary endosymbiot phage 1 | Bacteriophage, taxon: 67571 |
| AP-APSE2 dpol | Bacteriophage APSE-2, isolate = T5A | Bacteriophage of *Candidatus Hamiltonella defensa*, endosymbiot of *Acyrthosiphon pisum*, taxon: 340054 |
| AP-APSE4 dpol | Bacteriophage of *Candidatus Hamiltonella defensa* strain 5ATac, endosymbiot of *Acyrthosiphon pisum* | Bacteriophage, taxon: 568990 |
| AP-APSE5 dpol | Bacteriophage APSE-5 | Bacteriophage of *Candidatus Hamiltonella defensa*, endosymbiot of *Uroleucon rudbeckiae*, taxon: 568991 |
| AP-Aaphi23 MupF | Bacteriophage Aaphi23, *Haemophilus* phage Aaphi23 | *Actinobacillus actinomycetemcomitans* Bacteriophage, taxon: 230158 |
| Aae RIR2 | *Aquifex aeolicus* strain VF5 | Thermophilic chemolithoautotroph, taxon: 63363 |
| Aave-AAC001 Aave1721 | *Acidovorax avenae* subsp. *citrulli* AAC00-1 | taxon: 397945 |
| Aave-AAC001 RIR1 | *Acidovorax avenae* subsp. *citrulli* AAC00-1 | taxon: 397945 |
| Aave-ATCC19860 RIR1 | *Acidovorax avenae* subsp. *avenae* ATCC 19860 | Taxon: 643561 |
| Aba Hyp-02185 | *Acinetobacter baumannii* ACICU | taxon: 405416 |
| Ace RIR1 | *Acidothermus cellulolyticus* 11B | taxon: 351607 |
| Aeh DnaB-1 | *Alkalilimnicola ehrlichei* MLHE-1 | taxon: 187272 |
| Aeh DnaB-2 | *Alkalilimnicola ehrlichei* MLHE-1 | taxon: 187272 |
| Aeh RIR1 | *Alkalilimnicola ehrlichei* MLHE-1 | taxon: 187272 |
| AgP-S1249 MupF | *Aggregatibacter* phage S1249 | Taxon: 683735 |
| Aha DnaE-c | *Aphanothece halophytica* | Cyanobacterium, taxon: 72020 |
| Aha DnaE-n | *Aphanothece halophytica* | Cyanobacterium, taxon: 72020 |
| Alvi-DSM180 GyrA | *Allochromatium vinosum* DSM 180 | Taxon: 572477 |
| Ama MADE823 | phage uncharacterized protein [*Alteromonas macleodii* 'Deep ecotype'] | Probably prophage gene, taxon: 314275 |
| Amax-CS328 DnaX | *Arthrospira maxima* CS-328 | Taxon: 513049 |
| Aov DnaE-c | *Aphanizomenon ovalisporum* | Cyanobacterium, taxon: 75695 |
| Aov DnaE-n | *Aphanizomenon ovalisporum* | Cyanobacterium, taxon: 75695 |
| Apl-C1 DnaX | *Arthrospira platensis* | Taxon: 118562, strain C1 |
| Arsp-FB24 DnaB | *Arthrobacter* species FB24 | taxon: 290399 |
| Asp DnaE-c | *Anabaena* species PCC7120, (*Nostoc* sp. PCC7120) | Cyanobacterium, Nitrogen-fixing, taxon: 103690 |
| Asp DnaE-n | *Anabaena* species PCC7120, (*Nostoc* sp. PCC7120) | Cyanobacterium, Nitrogen-fixing, taxon: 103690 |
| Ava DnaE-c | *Anabaena variabilis* ATCC29413 | Cyanobacterium, taxon: 240292 |
| Ava DnaE-n | *Anabaena variabilis* ATCC29413 | Cyanobacterium, taxon: 240292 |
| Avin RIR1 BIL | *Azotobacter vinelandii* | taxon: 354 |
| Bce-MCO3 DnaB | *Burkholderia cenocepacia* MC0-3 | taxon: 406425 |
| Bce-PC184 DnaB | *Burkholderia cenocepacia* PC184 | taxon: 350702 |
| Bse-MLS10 TerA | *Bacillus selenitireducens* MLS10 | Probably prophage gene, Taxon: 439292 |
| BsuP-M1918 RIR1 | *B. subtilis* M1918 (prophage) | Prophage in *B. subtilis* M1918. taxon: 157928 |
| BsuP-SPBc2 RIR1 | *B. subtilis* strain 168 Sp beta c2 prophage | *B. subtilis* taxon 1423. SPbeta c2 phage, taxon: 66797 |
| Bvi IcmO | *Burkholderia vietnamiensis* G4 | plasmid = "pBVIE03". taxon: 269482 |
| CP-P1201 Thy1 | *Corynebacterium* phage P1201 | lytic bacteriophage P1201 from *Corynebacterium glutamicum* NCHU 87078.Viruses; dsDNA viruses, taxon: 384848 |
| Cag RIR1 | *Chlorochromatium aggregatum* | Motile, phototrophic consortia |
| Cau SpoVR | *Chloroflexus aurantiacus* J-10-fl | Anoxygenic phototroph, taxon: 324602 |
| CbP-C-St RNR | *Clostridium botulinum* phage C-St | Phage, specific_host = "*Clostridium botulinum* type C strain C-Stockholm, taxon: 12336 |

TABLE 2-continued

| Naturally Occurring Inteins | | |
|---|---|---|
| Intein Name | Organism Name | Organism Description |
| CbP-D1873 RNR | *Clostridium botulinum* phage D | Ssp. phage from *Clostridium botulinum* type D strain, 1873, taxon: 29342 |
| Cbu-Dugway DnaB | *Coxiella burnetii* Dugway 5J108-111 | Proteobacteria; Legionellales; taxon: 434922 |
| Cbu-Goat DnaB | *Coxiella burnetii* 'MSU Goat Q177' | Proteobacteria; Legionellales; taxon: 360116 |
| Cbu-RSA334 DnaB | *Coxiella burnetii* RSA 334 | Proteobacteria; Legionellales; taxon: 360117 |
| Cbu-RSA493 DnaB | *Coxiella burnetii* RSA 493 | Proteobacteria; Legionellales; taxon: 227377 |
| Cce Hyp1-Csp-2 | *Cyanothece* sp. ATCC 51142 | Marine unicellular diazotrophic *cyanobacterium*, taxon: 43989 |
| Cch RIR1 | *Chlorobium chlorochromatii* CaD3 | taxon: 340177 |
| Ccy Hyp1-Csp-1 | *Cyanothece* sp. CCY0110 | *Cyanobacterium*, taxon: 391612 |
| Ccy Hyp1-Csp-2 | *Cyanothece* sp. CCY0110 | *Cyanobacterium*, taxon: 391612 |
| Cfl-DSM20109 DnaB | *Cellulomonas flavigena* DSM 20109 | Taxon: 446466 |
| Chy RIR1 | *Carboxydothermus hydrogenoformans* Z-2901 | Thermophile, taxon = 246194 |
| Ckl PTerm | *Clostridium kluyveri* DSM 555 | plasmid = "pCKL555A", taxon: 431943 |
| Cra-CS505 DnaE-c | *Cylindrospermopsis raciborskii* CS-505 | Taxon: 533240 |
| Cra-CS505 DnaE-n | *Cylindrospermopsis raciborskii* CS-505 | Taxon: 533240 |
| Cra-CS505 GyrB | *Cylindrospermopsis raciborskii* CS-505 | Taxon: 533240 |
| Csp-CCY0110 DnaE-c | *Cyanothece* sp. CCY0110 | Taxon: 391612 |
| Csp-CCY0110 DnaE-n | *Cyanothece* sp. CCY0110 | Taxon: 391612 |
| Csp-PCC7424 DnaE-c | *Cyanothece* sp. PCC 7424 | *Cyanobacterium*, taxon: 65393 |
| Csp-PCC7424 DnaE-n | *Cyanothece* sp. PCC7424 | *Cyanobacterium*, taxon: 65393 |
| Csp-PCC7425 DnaB | *Cyanothece* sp. PCC 7425 | Taxon: 395961 |
| Csp-PCC7822 DnaE-n | *Cyanothece* sp. PCC 7822 | Taxon: 497965 |
| Csp-PCC8801 DnaE-c | *Cyanothece* sp. PCC 8801 | Taxon: 41431 |
| Csp-PCC8801 DnaE-n | *Cyanothece* sp. PCC 8801 | Taxon: 41431 |
| Cth ATPase BIL | *Clostridium thermocellum* | ATCC27405, taxon: 203119 |
| Cth-ATCC27405 TerA | *Clostridium thermocellum* ATCC27405 | Probable prophage, ATCC27405, taxon: 203119 |
| Cth-DSM2360 TerA | *Clostridium thermocellum* DSM 2360 | Probably prophage gene, Taxon: 572545 |
| Cwa DnaB | *Crocosphaera watsonii* WH 8501 (*Synechocystis* sp. WH 8501) | taxon: 165597 |
| Cwa DnaE-c | *Crocosphaera watsonii* WH 8501 (*Synechocystis* sp. WH 8501) | *Cyanobacterium*, taxon: 165597 |
| Cwa DnaE-n | *Crocosphaera watsonii* WH 8501 (*Synechocystis* sp. WH 8501) | *Cyanobacterium*, taxon: 165597 |
| Cwa PEP | *Crocosphaera watsonii* WH 8501 (*Synechocystis* sp. WH 8501) | taxon: 165597 |
| Cwa RIR1 | *Crocosphaera watsonii* WH 8501 (*Synechocystis* sp. WH 8501) | taxon: 165597 |
| Daud RIR1 | *Candidatus Desulforudis audaxviator* MP104C | taxon: 477974 |
| Dge DnaB | *Deinococcus geothermalis* DSM11300 | Thermophilic, radiation resistant |
| Dha-DCB2 RIR1 | *Desulfitobacterium hafniense* DCB-2 | Anaerobic dehalogenating bacteria, taxon: 49338 |
| Dha-Y51 RIR1 | *Desulfitobacterium hafniense* Y51 | Anaerobic dehalogenating bacteria, taxon: 138119 |
| Dpr-MLMSl RIR1 | delta proteobacterium MLMS-1 | Taxon: 262489 |
| Dra RIR1 | *Deinococcus radiodurans* R1, TIGR strain | Radiation resistant, taxon: 1299 |
| Dra Snf2-c | *Deinococcus radiodurans* R1, TIGR strain | Radiation and DNA damage resistent, taxon: 1299 |
| Dra Snf2-n | *Deinococcus radiodurans* R1, TIGR strain | Radiation and DNA damage resistent, taxon: 1299 |
| Dra-ATCC13939 Snf2 | *Deinococcus radiodurans* R1, ATCC13939/Brooks & Murray strain | Radiation and DNA damage resistent, taxon: 1299 |
| Dth UDP GD | *Dictyoglomus thermophilum* H-6-12 | strain = "H-6-12; ATCC 35947, taxon: 309799 |
| Dvul ParB | *Desulfovibrio vulgaris* subsp. *vulgaris* DP4 | taxon: 391774 |
| EP-Min27 Primase | *Enterobacteria* phage Min27 | bacteriphage of host = "*Escherichia coli* O157: H7 str. Min27" |
| Fal DnaB | *Frankia alni* ACN14a | Plant symbiot, taxon: 326424 |
| Fsp-CcI3 RIR1 | *Frankia* species CcI3 | taxon: 106370 |

TABLE 2-continued

Naturally Occurring Inteins

| Intein Name | Organism Name | Organism Description |
|---|---|---|
| Gob DnaE | *Gemmata obscuriglobus* UQM2246 | Taxon 114, TIGR genome strain, budding bacteria |
| Gob Hyp | *Gemmata obscuriglobus* UQM2246 | Taxon 114, TIGR genome strain, budding bacteria |
| Gvi DnaB | *Gloeobacter violaceus*, PCC 7421 | taxon: 33072 |
| Gvi RIR1-1 | *Gloeobacter violaceus*, PCC 7421 | taxon: 33072 |
| Gvi RIR1-2 | *Gloeobacter violaceus*, PCC 7421 | taxon: 33072 |
| Hhal DnaB | *Halorhodospira halophila* SL1 | taxon: 349124 |
| Kfl-DSM17836 DnaB | *Kribbella flavida* DSM 17836 | Taxon: 479435 |
| Kra DnaB | *Kineococcus radiotolerans* SRS30216 | Radiation resistant |
| LLP-KSY1 PolA | *Lactococcus* phage KSY1 | Bacteriophage, taxon: 388452 |
| LP-phiHSIC Helicase | *Listonella pelagia* phage phiHSIC | taxon: 310539, a pseudotemperate marine phage of *Listonella pelagia* |
| Lsp-PCC8106 GyrB | *Lyngbya* sp. PCC 8106 | Taxon: 313612 |
| MP-Be DnaB | Mycobacteriophage Bethlehem | Bacteriophage, taxon: 260121 |
| MP-Be gp51 | Mycobacteriophage Bethlehem | Bacteriophage, taxon: 260121 |
| MP-Catera gp206 | Mycobacteriophage Catera | Mycobacteriophage, taxon: 373404 |
| MP-KBG gp53 | *Mycobacterium* phage KBG | Taxon: 540066 |
| MP-Mcjw1 DnaB | Mycobacteriophage CJW1 | Bacteriophage, taxon: 205869 |
| MP-Omega DnaB | Mycobacteriophage Omega | Bacteriophage, taxon: 205879 |
| MP-U2 gp50 | Mycobacteriophage U2 | Bacteriophage, taxon: 260120 |
| Maer-NIES843 DnaB | *Microcystis aeruginosa* NIES-843 | Bloom-forming toxic cyanobacterium, taxon: 449447 |
| Maer-NIES843 DnaE-c | *Microcystis aeruginosa* NIES-843 | Bloom-forming toxic cyanobacterium, taxon: 449447 |
| Maer-NIES843 DnaE-n | *Microcystis aeruginosa* NIES-843 | Bloom-forming toxic cyanobacterium, taxon: 449447 |
| Mau-ATCC27029 GyrA | *Micromonospora aurantiaca* ATCC 27029 | Taxon: 644283 |
| Mav-104 DnaB | *Mycobacterium avium* 104 | taxon: 243243 |
| Mav-ATCC25291 DnaB | *Mycobacterium avium* subsp. *avium* ATCC 25291 | Taxon: 553481 |
| Mav-ATCC35712 DnaB | *Mycobacterium avium* | ATCC35712, taxon 1764 |
| Mav-PT DnaB | *Mycobacterium avium* subsp. *paratuberculosis* str. k10 | taxon: 262316 |
| Mbo Pps1 | *Mycobacterium bovis* subsp. *bovis* AF2122/97 | strain = "AF2122/97", taxon: 233413 |
| Mbo RecA | *Mycobacterium bovis* subsp. bovis AF2122/97 | taxon: 233413 |
| Mbo SufB (Mbo Pps1) | *Mycobacterium bovis* subsp. *bovis* AF2122/97 | taxon: 233413 |
| Mbo-1173P DnaB | *Mycobacterium bovis* BCG Pasteur 1173P | strain = BCG Pasteur 1173P2,, taxon: 410289 |
| Mbo-AF2122 DnaB | *Mycobacterium bovis* subsp. *bovis* AF2122/97 | strain = "AF2122/97", taxon: 233413 |
| Mca MupF | *Methylococcus capsulatus* Bath, prophage MuMc02 | prophage MuMc02, taxon: 243233 |
| Mca RIR1 | *Methylococcus capsulatus* Bath | taxon: 243233 |
| Mch RecA | *Mycobacterium chitae* | IP14116003, taxon: 1792 |
| Mcht-PCC7420 DnaE-1 | *Microcoleus chthonoplastes* PCC7420 | *Cyanobacterium*, taxon: 118168 |
| Mcht-PCC7420 DnaE-2c | *Microcoleus chthonoplastes* PCC7420 | *Cyanobacterium*, taxon: 118168 |
| Mcht-PCC7420 DnaE-2n | *Microcoleus chthonoplastes* PCC7420 | *Cyanobacterium*, taxon: 118168 |
| Mcht-PCC7420 GyrB | *Microcoleus chthonoplastes* PCC 7420 | Taxon: 118168 |
| Mcht-PCC7420 RIR1-1 | *Microcoleus chthonoplastes* PCC 7420 | Taxon: 118168 |
| Mcht-PCC7420 RIR1-2 | *Microcoleus chthonoplastes* PCC 7420 | Taxon: 118168 |
| Mex Helicase | *Methylobacterium extorquens* AMI | Alphaproteobacteria |
| Mex TrbC | *Methylobacterium extorquens* AMI | Alphaproteobacteria |
| Mfa RecA | *Mycobacterium fallax* | CITP8139, taxon: 1793 |
| Mfl GyrA | *Mycobacterium flavescens* Fla0 | taxon: 1776, reference #930991 |
| Mfl RecA | *Mycobacterium flavescens* Fla0 | strain = Fla0, taxon: 1776, ref. #930991 |
| Mfl-ATCC14474 RecA | *Mycobacterium flavescens*, ATCC14474 | strain = ATCC14474, taxon: 1776, ref #930991 |
| Mfl-PYR-GCK DnaB | *Mycobacterium flavescens* PYR-GCK | taxon: 350054 |

TABLE 2-continued

Naturally Occurring Inteins

| Intein Name | Organism Name | Organism Description |
|---|---|---|
| Mga GyrA | *Mycobacterium gastri* | HP4389, taxon: 1777 |
| Mga RecA | *Mycobacterium gastri* | HP4389, taxon: 1777 |
| Mga SufB (Mga Pps1) | *Mycobacterium gastri* | HP4389, taxon: 1777 |
| Mgi-PYR-GCK DnaB | *Mycobacterium gilvum* PYR-GCK | taxon: 350054 |
| Mgi-PYR-GCK GyrA | *Mycobacterium gilvum* PYR-GCK | taxon: 350054 |
| Mgo GyrA | *Mycobacterium gordonae* | taxon: 1778, reference number 930835 |
| Min-1442 DnaB | *Mycobacterium intracellulare* | strain 1442, taxon: 1767 |
| Min-ATCC13950 GyrA | *Mycobacterium intracellulare* ATCC 13950 | Taxon: 487521 |
| Mkas GyrA | *Mycobacterium kansasii* | taxon: 1768 |
| Mkas-ATCC12478 GyrA | *Mycobacterium kansasii* ATCC 12478 | Taxon: 557599 |
| Mle-Br4923 GyrA | *Mycobacterium leprae* Br4923 | Taxon: 561304 |
| Mle-TN DnaB | *Mycobacterium leprae*, strain TN | Human pathogen, taxon: 1769 |
| Mle-TN GyrA | *Mycobacterium leprae* TN | Human pathogen, STRAIN = TN, taxon: 1769 |
| Mle-TN RecA | *Mycobacterium leprae*, strain TN | Human pathogen, taxon: 1769 |
| Mle-TN SufB (Mle Pps1) | *Mycobacterium leprae* | Human pathogen, taxon: 1769 |
| Mma GyrA | *Mycobacterium malmoense* | taxon: 1780 |
| Mmag Magn8951 BIL | *Magnetospirillum magnetotacticum* MS-1 | Gram negative, taxon: 272627 |
| Msh RecA | *Mycobacterium shimodei* | ATCC27962, taxon: 29313 |
| Msm DnaB-1 | *Mycobacterium smegmatis* MC2 155 | MC2 155, taxon: 246196 |
| Msm DnaB-2 | *Mycobacterium smegmatis* MC2 155 | MC2 155, taxon: 246196 |
| Msp-KMS DnaB | *Mycobacterium* species KMS | taxon: 189918 |
| Msp-KMS GyrA | *Mycobacterium* species KMS | taxon: 189918 |
| Msp-MCS DnaB | *Mycobacterium* species MCS | taxon: 164756 |
| Msp-MCS GyrA | *Mycobacterium* species MCS | taxon: 164756 |
| Mthe RecA | *Mycobacterium thermoresistibile* | ATCC19527, taxon: 1797 |
| Mtu SufB (Mtu Pps1) | *Mycobacterium tuberculosis* strains H37Rv & CDC1551 | Human pathogen, taxon: 83332 |
| Mtu-C RecA | *Mycobacterium tuberculosis* C | Taxon: 348776 |
| Mtu-CDC1551 DnaB | *Mycobacterium tuberculosis*, CDC1551 | Human pathogen, taxon: 83332 |
| Mtu-CPHL RecA | *Mycobacterium tuberculosis* CPHL_A | Taxon: 611303 |
| Mtu-Canetti RecA | *Mycobacterium tuberculosis*/ strain = "Canetti" | Taxon: 1773 |
| Mtu-EAS054 RecA | *Mycobacterium tuberculosis* EAS054 | Taxon: 520140 |
| Mtu-F11 DnaB | *Mycobacterium tuberculosis*, strain F11 | taxon: 336982 |
| Mtu-H37Ra DnaB | *Mycobacterium tuberculosis* H37Ra | ATCC 25177, taxon: 419947 |
| Mtu-H37Rv DnaB | *Mycobacterium tuberculosis* H37Rv | Human pathogen, taxon: 83332 |
| Mtu-H37Rv RecA | *Mycobacterium tuberculosis* H37Rv, Also CDC1551 | Human pathogen, taxon: 83332 |
| Mtu-Haarlem DnaB | *Mycobacterium tuberculosis* str. Haarlem | Taxon: 395095 |
| Mtu-K85 RecA | *Mycobacterium tuberculosis* K85 | Taxon: 611304 |
| Mtu-R604 RecA-n | *Mycobacterium tuberculosis* '98-R604 INH-RIF-EM' | Taxon: 555461 |
| Mtu-So93 RecA | *Mycobacterium tuberculosis* So93/sub_species = "Canetti" | Human pathogen, taxon: 1773 |
| Mtu-T17 RecA-c | *Mycobacterium tuberculosis* T17 | Taxon: 537210 |
| Mtu-T17 RecA-n | *Mycobacterium tuberculosis* T17 | Taxon: 537210 |
| Mtu-T46 RecA | *Mycobacterium tuberculosis* T46 | Taxon: 611302 |
| Mtu-T85 RecA | *Mycobacterium tuberculosis* T85 | Taxon: 520141 |
| Mtu-T92 RecA | *Mycobacterium tuberculosis* T92 | Taxon: 515617 |
| Mvan DnaB | *Mycobacterium vanbaalenii* PYR-1 | taxon: 350058 |
| Mvan GyrA | *Mycobacterium vanbaalenii* PYR-1 | taxon: 350058 |
| Mxa RAD25 | *Myxococcus xanthus* DK1622 | Deltaproteobacteria |
| Mxe GyrA | *Mycobacterium xenopi* strain IMM5024 | taxon: 1789 |
| Naz-0708 RIR1-1 | *Nostoc azollae* 0708 | Taxon: 551115 |
| Naz-0708 RIR1-2 | *Nostoc azollae* 0708 | Taxon: 551115 |
| Nfa DnaB | *Nocardia farcinica* IFM 10152 | taxon: 247156 |
| Nfa Nfa15250 | *Nocardia farcinica* IFM 10152 | taxon: 247156 |
| Nfa RIR1 | *Nocardia farcinica* IFM 10152 | taxon: 247156 |
| Nosp-CCY9414 DnaE-n | *Nodularia spumigena* CCY9414 | Taxon: 313624 |
| Npu DnaB | *Nostoc punctiforme* | Cyanobacterium, taxon: 63737 |
| Npu GyrB | *Nostoc punctiforme* | Cyanobacterium, taxon: 63737 |
| Npu-PCC73102 DnaE-c | *Nostoc punctiforme* PCC73102 | Cyanobacterium, taxon: 63737, ATCC29133 |
| Npu-PCC73102 DnaE-n | *Nostoc punctiforme* PCC73102 | Cyanobacterium, taxon: 63737, ATCC29133 |

TABLE 2-continued

Naturally Occurring Inteins

| Intein Name | Organism Name | Organism Description |
| --- | --- | --- |
| Nsp-JS614 DnaB | *Nocardioides* species JS614 | taxon: 196162 |
| Nsp-JS614 TOPRIM | *Nocardioides* species JS614 | taxon: 196162 |
| Nsp-PCC7120 DnaB | *Nostoc* species PCC7120, (*Anabaena* sp. PCC7120) | *Cyanobacterium*, Nitrogen-fixing, taxon: 103690 |
| Nsp-PCC7120 DnaE-c | *Nostoc* species PCC7120, (*Anabaena* sp. PCC7120) | *Cyanobacterium*, Nitrogen-fixing, taxon: 103690 |
| Nsp-PCC7120 DnaE-n | *Nostoc* species PCC7120, (*Anabaena* sp. PCC7120) | *Cyanobacterium*, Nitrogen-fixing, taxon: 103690 |
| Nsp-PCC7120 RIR1 | *Nostoc* species PCC7120, (*Anabaena* sp. PCC7120) | *Cyanobacterium*, Nitrogen-fixing, taxon: 103690 |
| Oli DnaE-c | *Oscillatoria limnetica* str. 'Solar Lake' | *Cyanobacterium*, taxon: 262926 |
| Oli DnaE-n | *Oscillatoria limnetica* str. 'Solar Lake' | *Cyanobacterium*, taxon: 262926 |
| PP-PhiEL Helicase | *Pseudomonas aeruginosa* phage phiEL | Phage infects *Pseudomonas aeruginosa*, taxon: 273133 |
| PP-PhiEL ORF11 | *Pseudomonas aeruginosa* phage phiEL | phage infects *Pseudomonas aeruginosa*, taxon: 273133 |
| PP-PhiEL ORF39 | *Pseudomonas aeruginosa* phage phiEL | Phage infects *Pseudomonas aeruginosa*, taxon: 273133 |
| PP-PhiEL ORF40 | *Pseudomonas aeruginosa* phage phiEL | phage infects *Pseudomonas aeruginosa*, taxon: 273133 |
| Pfl Fha BIL | *Pseudomonas fluorescens* Pf-5 | Plant commensal organism, taxon: 220664 |
| Plut RIR1 | *Pelodictyon luteolum* DSM 273 | Green sulfur bacteria, Taxon 319225 |
| Pma-EXH1 GyrA | *Persephonella marina* EX-H1 | Taxon: 123214 |
| Pma-ExH1 DnaE | *Persephonella marina* EX-H1 | Taxon: 123214 |
| Pna RIR1 | *Polaromonas naphthalenivorans* CJ2 | taxon: 365044 |
| Pnuc DnaB | *Polynucleobacter* sp. QLW-P1DMWA-1 | taxon: 312153 |
| Posp-JS666 DnaB | *Polaromonas* species JS666 | taxon: 296591 |
| Posp-JS666 RIR1 | *Polaromonas* species JS666 | taxon: 296591 |
| Pssp-A1-1 Fha | *Pseudomonas* species A1-1 | |
| Psy Fha | *Pseudomonas syringae* pv. tomato str. DC3000 | Plant (tomato) pathogen, taxon: 223283 |
| Rbr-D9 GyrB | *Raphidiopsis brookii* D9 | Taxon: 533247 |
| Rce RIR1 | *Rhodospirillum centenum* SW | taxon: 414684, ATCC 51521 |
| Rer-SK121 DnaB | *Rhodococcus erythropolis* SK121 | Taxon: 596309 |
| Rma DnaB | *Rhodothermus marinus* | Thermophile, taxon: 29549 |
| Rma-DSM4252 DnaB | *Rhodothermus marinus* DSM 4252 | Taxon: 518766 |
| Rma-DSM4252 DnaE | *Rhodothermus marinus* DSM 4252 | Thermophile, taxon: 518766 |
| Rsp RIR1 | *Roseovarius* species 217 | taxon: 314264 |
| SaP-SETP12 dpol | *Salmonella* phage SETP12 | Phage, taxon: 424946 |
| SaP-SETP3 Helicase | *Salmonella* phage SETP3 | Phage, taxon: 424944 |
| SaP-SETP3 dpol | *Salmonella* phage SETP3 | Phage, taxon: 424944 |
| SaP-SETP5 dpol | *Salmonella* phage SETP5 | Phage, taxon: 424945 |
| Sare DnaB | *Salinispora arenicola* CNS-205 | taxon: 391037 |
| Sav RecG Helicase | *Streptomyces avermitilis* MA-4680 | taxon: 227882, ATCC 31267 |
| Sel-PC6301 RIR1 | *Synechococcus elongatus* PCC 6301 | taxon: 269084 Berkely strain 6301~equivalent name: Ssp PCC 6301~synonym: *Anacystis nudulans* |
| Sel-PC7942 DnaE-c | *Synechococcus elongatus* PC7942 | taxon: 1140 |
| Sel-PC7942 DnaE-n | *Synechococcus elongatus* PC7942 | taxon: 1140 |
| Sel-PC7942 RIR1 | *Synechococcus elongatus* PC7942 | taxon: 1140 |
| Sel-PCC6301 DnaE-c | *Synechococcus elongatus* PCC 6301 and PCC7942 | *Cyanobacterium*, taxon: 269084, "Berkely strain 6301~equivalent name: *Synechococcus* sp. PCC 6301~synonym: *Anacystis nudulans*" |
| Sel-PCC6301 DnaE-n | *Synechococcus elongatus* PCC 6301 | *Cyanobacterium*, taxon: 269084"Berkely strain 6301~equivalent name: *Synechococcus* sp. PCC 6301~synonym: *Anacystis nudulans*" |
| Sep RIR1 | *Staphylococcus epidermidis* RP62A | taxon: 176279 |
| ShP-Sfv-2a-2457T-n Primase | *Shigella flexneri* 2a str. 2457T | Putative bacteriphage |
| ShP-Sfv-2a-301-n Primase | *Shigella flexneri* 2a str. 301 | Putative bacteriphage |
| ShP-Sfv-5 Primase | *Shigella flexneri* 5 str. 8401 | Bacteriphage, isolation_source_epidemic, taxon: 373384 |

TABLE 2-continued

Naturally Occurring Inteins

| Intein Name | Organism Name | Organism Description |
| --- | --- | --- |
| SoP-SO1 dpol | *Sodalis* phage SO-1 | Phage/isolation_source = "*Sodalis glossinidius* strain GA-SG, secondary symbiont of *Glossina austeni* (Newstead)" |
| Spl DnaX | *Spirulina platensis*, strain C1 | Cyanobacterium, taxon: 1156 |
| Sru DnaB | *Salinibacter ruber* DSM 13855 | taxon: 309807, strain = "DSM 13855; M31" |
| Sru PolBc | *Salinibacter ruber* DSM 13855 | taxon: 309807, strain = "DSM 13855; M31" |
| Sru RIR1 | *Salinibacter ruber* DSM 13855 | taxon: 309807, strain = "DSM 13855; M31" |
| Ssp DnaB | *Synechocystis* species, strain PCC6803 | Cyanobacterium, taxon: 1148 |
| Ssp DnaE-c | *Synechocystis* species, strain PCC6803 | Cyanobacterium, taxon: 1148 |
| Ssp DnaE-n | *Synechocystis* species, strain PCC6803 | Cyanobacterium, taxon: 1148 |
| Ssp DnaX | *Synechocystis* species, strain PCC6803 | Cyanobacterium, taxon: 1148 |
| Ssp GyrB | *Synechocystis* species, strain PCC6803 | Cyanobacterium, taxon: 1148 |
| Ssp-JA2 DnaB | *Synechococcus* species JA-2-3B'a(2-13) | Cyanobacterium, Taxon: 321332 |
| Ssp-JA2 RIR1 | *Synechococcus* species JA-2-3B'a(2-13) | Cyanobacterium, Taxon: 321332 |
| Ssp-JA3 DnaB | *Synechococcus* species JA-3-3Ab | Cyanobacterium, Taxon: 321327 |
| Ssp-JA3 RIR1 | *Synechococcus* species JA-3-3Ab | Cyanobacterium, Taxon: 321327 |
| Ssp-PCC7002 DnaE-c | *Synechocystis* species, strain PCC 7002 | Cyanobacterium, taxon: 32049 |
| Ssp-PCC7002 DnaE-n | *Synechocystis* species, strain PCC 7002 | Cyanobacterium, taxon: 32049 |
| Ssp-PCC7335 RIR1 | *Synechococcus* sp. PCC 7335 | Taxon: 91464 |
| StP-Twort ORF6 | *Staphylococcus* phage Twort | Phage, taxon 55510 |
| Susp-NBC371 DnaB intein | *Sulfurovum* sp. NBC37-1 | taxon: 387093 |
| Taq-Y51MC23 DnaE | *Thermus aquaticus* Y51MC23 | Taxon: 498848 |
| Taq-Y51MC23 RIR1 | *Thermus aquaticus* Y51MC23 | Taxon: 498848 |
| Tcu-DSM43183 RecA | *Thermomonospora curvata* DSM 43183 | Taxon: 471852 |
| Tel DnaE-c | *Thermosynechococcus elongatus* BP-1 | Cyanobacterium, taxon: 197221 |
| Tel DnaE-n | *Thermosynechococcus elongatus* BP-1 | Cyanobacterium, |
| Ter DnaB-1 | *Trichodesmium erythraeum* IMS101 | Cyanobacterium, taxon: 203124 |
| Ter DnaB-2 | *Trichodesmium erythraeum* IMS101 | Cyanobacterium, taxon: 203124 |
| Ter DnaE-1 | *Trichodesmium erythraeum* IMS101 | Cyanobacterium, taxon: 203124 |
| Ter DnaE-2 | *Trichodesmium erythraeum* IMS101 | Cyanobacterium, taxon: 203124 |
| Ter DnaE-3c | *Trichodesmium erythraeum* IMS101 | Cyanobacterium, taxon: 203124 |
| Ter DnaE-3n | *Trichodesmium erythraeum* IMS101 | Cyanobacterium, taxon: 203124 |
| Ter GyrB | *Trichodesmium erythraeum* IMS101 | Cyanobacterium, taxon: 203124 |
| Ter Ndse-1 | *Trichodesmium erythraeum* IMS101 | Cyanobacterium, taxon: 203124 |
| Ter Ndse-2 | *Trichodesmium erythraeum* IMS101 | Cyanobacterium, taxon: 203124 |
| Ter RIR1-1 | *Trichodesmium erythraeum* IMS101 | Cyanobacterium, taxon: 203124 |
| Ter RIR1-2 | *Trichodesmium erythraeum* IMS101 | Cyanobacterium, taxon: 203124 |
| Ter RIR1-3 | *Trichodesmium erythraeum* IMS101 | Cyanobacterium, taxon: 203124 |
| Ter RIR1-4 | *Trichodesmium erythraeum* IMS101 | Cyanobacterium, taxon: 203124 |
| Ter Snf2 | *Trichodesmium erythraeum* IMS101 | Cyanobacterium, taxon: 203124 |
| Ter ThyX | *Trichodesmium erythraeum* IMS101 | Cyanobacterium, taxon: 203124 |
| Tfus RecA-1 | *Thermobifida fusca* YX | Thermophile, taxon: 269800 |
| Tfus RecA-2 | *Thermobifida fusca* YX | Thermophile, taxon: 269800 |
| Tfus Tfu2914 | *Thermobifida fusca* YX | Thermophile, taxon: 269800 |
| Thsp-K90 RIR1 | *Thioalkalivibrio* sp. K90mix | Taxon: 396595 |
| Tth-DSM571 RIR1 | *Thermoanaerobacterium thermosaccharolyticum* DSM 571 | Taxon: 580327 |
| Tth-HB27 DnaE-1 | *Thermus thermophilus* HB27 | thermophile, taxon: 262724 |
| Tth-HB27 DnaE-2 | *Thermus thermophilus* HB27 | thermophile, taxon: 262724 |
| Tth-HB27 RIR1-1 | *Thermus thermophilus* HB27 | thermophile, taxon: 262724 |
| Tth-HB27 RIR1-2 | *Thermus thermophilus* HB27 | thermophile, taxon: 262724 |
| Tth-HB8 DnaE-1 | *Thermus thermophilus* HB8 | thermophile, taxon: 300852 |
| Tth-HB8 DnaE-2 | *Thermus thermophilus* HB8 | thermophile, taxon: 300852 |
| Tth-HB8 RIR1-1 | *Thermus thermophilus* HB8 | thermophile, taxon: 300852 |
| Tth-HB8 RIR1-2 | *Thermus thermophilus* HB8 | thermophile, taxon: 300852 |
| Tvu DnaE-c | *Thermosynechococcus vulcanus* | Cyanobacterium, taxon: 32053 |
| Tvu DnaE-n | *Thermosynechococcus vulcanus* | Cyanobacterium, taxon: 32053 |
| Tye RNR-1 | *Thermodesulfovibrio yellowstonii* DSM 11347 | taxon: 289376 |
| Tye RNR-2 | *Thermodesulfovibrio yellowstonii* DSM 11347 | taxon: 289376 |

TABLE 2-continued

Naturally Occurring Inteins

| Intein Name | Organism Name | Organism Description |
|---|---|---|
| Archaea | | |
| Ape APE0745 | *Aeropyrum pernix* K1 | Thermophile, taxon: 56636 |
| Cme-boo Pol-II | *Candidatus Methanoregula boonei* 6A8 | taxon: 456442 |
| Fac-Fer1 RIR1 | *Ferroplasma acidarmanus*, taxon: 97393 and taxon 261390 | strain Fer1, eats iron |
| Fac-Fer1 SufB (Fac Pps1) | *Ferroplasma acidarmanus* | strain fer1, eats iron, taxon: 97393 |
| Fac-TypeI RIR1 | *Ferroplasma acidarmanus* type I, | Eats iron, taxon 261390 |
| Fac-typeI SufB (Fac Pps1) | *Ferroplasma acidarmanus* | Eats iron, taxon: 261390 |
| Hma CDC21 | *Haloarcula marismortui* ATCC 43049 | taxon: 272569, |
| Hma Pol-II | *Haloarcula marismortui* ATCC 43049 | taxon: 272569, |
| Hma PolB | *Haloarcula marismortui* ATCC 43049 | taxon: 272569, |
| Hma TopA | *Haloarcula marismortui* ATCC 43049 | taxon: 272569 |
| Hmu-DSM12286 MCM | *Halomicrobium mukohataei* DSM 12286 | taxon: 485914 (*Halobacteria*) |
| Hmu-DSM12286 PolB | *Halomicrobium mukohataei* DSM 12286 | Taxon: 485914 |
| Hsa-R1 MCM | *Halobacterium salinarum* R-1 | Halophile, taxon: 478009, strain = "R1; DSM 671" |
| Hsp-NRC1 CDC21 | *Halobacterium* species NRC-1 | Halophile, taxon: 64091 |
| Hsp-NRC1 Pol-II | *Halobacterium salinarum* NRC-1 | Halophile, taxon: 64091 |
| Hut MCM-2 | *Halorhabdus utahensis* DSM 12940 | taxon: 519442 |
| Hut-DSM12940 MCM-1 | *Halorhabdus utahensis* DSM 12940 | taxon: 519442 |
| Hvo PolB | *Haloferax volcanii* DS70 | taxon: 2246 |
| Hwa GyrB | *Haloquadratum walsbyi* DSM 16790 | Halophile, taxon: 362976, strain: DSM 16790 = HBSQ001 |
| Hwa MCM-1 | *Haloquadratum walsbyi* DSM 16790 | Halophile, taxon: 362976, strain: DSM 16790 = HBSQ001 |
| Hwa MCM-2 | *Haloquadratum walsbyi* DSM 16790 | Halophile, taxon: 362976, strain: DSM 16790 = HBSQ001 |
| Hwa MCM-3 | *Haloquadratum walsbyi* DSM 16790 | Halophile, taxon: 362976, strain: DSM 16790 = HBSQ001 |
| Hwa MCM-4 | *Haloquadratum walsbyi* DSM 16790 | Halophile, taxon: 362976, strain: DSM 16790 = HBSQ001 |
| Hwa Pol-II-1 | *Haloquadratum walsbyi* DSM 16790 | Halophile, taxon: 362976, strain: DSM 16790 = HBSQ001 |
| Hwa Pol-II-2 | *Haloquadratum walsbyi* DSM 16790 | Halophile, taxon: 362976, strain: DSM 16790 = HBSQ001 |
| Hwa PolB-1 | *Haloquadratum walsbyi* DSM 16790 | Halophile, taxon: 362976, strain: DSM 16790 = HBSQ001 |
| Hwa PolB-2 | *Haloquadratum walsbyi* DSM 16790 | Halophile, taxon: 362976, strain: DSM 16790 = HBSQ001 |
| Hwa PolB-3 | *Haloquadratum walsbyi* DSM 16790 | Halophile, taxon: 362976, strain: DSM 16790 = HBSQ001 |
| Hwa RCF | *Haloquadratum walsbyi* DSM 16790 | Halophile, taxon: 362976, strain: DSM 16790 = HBSQ001 |
| Hwa RIR1-1 | *Haloquadratum walsbyi* DSM 16790 | Halophile, taxon: 362976, strain: DSM 16790 = HBSQ001 |
| Hwa RIR1-2 | *Haloquadratum walsbyi* DSM 16790 | Halophile, taxon: 362976, strain: DSM 16790 = HBSQ001 |
| Hwa Top6B | *Haloquadratum walsbyi* DSM 16790 | Halophile, taxon: 362976, strain: DSM 16790 = HBSQ001 |

TABLE 2-continued

Naturally Occurring Inteins

| Intein Name | Organism Name | Organism Description |
| --- | --- | --- |
| Hwa rPol A" | *Haloquadratum walsbyi* DSM 16790 | Halophile, taxon: 362976, strain: DSM 16790 = HBSQ001 |
| Maeo Pol-II | *Methanococcus aeolicus* Nankai-3 | taxon: 419665 |
| Maeo RFC | *Methanococcus aeolicus* Nankai-3 | taxon: 419665 |
| Maeo RNR | *Methanococcus aeolicus* Nankai-3 | taxon: 419665 |
| Maeo-N3 Helicase | *Methanococcus aeolicus* Nankai-3 | taxon: 419665 |
| Maeo-N3 RtcB | *Methanococcus aeolicus* Nankai-3 | taxon: 419665 |
| Maeo-N3 UDP GD | *Methanococcus aeolicus* Nankai-3 | taxon: 419665 |
| Mein-ME PEP | *Methanocaldococcus infernus* ME | thermophile, Taxon: 573063 |
| Mein-ME RFC | *Methanocaldococcus infernus* ME | Taxon: 573063 |
| Memar MCM2 | *Methanoculleus marisnigri* JR1 | taxon: 368407 |
| Memar Pol-II | *Methanoculleus marisnigri* JR1 | taxon: 368407 |
| Mesp-FS406 PolB-1 | *Methanocaldococcus* sp. FS406-22 | Taxon: 644281 |
| Mesp-FS406 PolB-2 | *Methanocaldococcus* sp. FS406-22 | Taxon: 644281 |
| Mesp-FS406 PolB-3 | *Methanocaldococcus* sp. FS406-22 | Taxon: 644281 |
| Mesp-FS406-22 LHR | *Methanocaldococcus* sp. FS406-22 | Taxon: 644281 |
| Mfe-AG86 Pol-1 | *Methanocaldococcus fervens* AG86 | Taxon: 573064 |
| Mfe-AG86 Pol-2 | *Methanocaldococcus fervens* AG86 | Taxon: 573064 |
| Mhu Pol-II | *Methanospirillum hungateii* JF-1 | taxon 323259 |
| Mja GF-6P | *Methanococcus jannaschii* (*Methanocaldococcus jannaschii* DSM 2661) | Thermophile, DSM 2661, taxon: 2190 |
| Mja Helicase | *Methanococcus jannaschii* (*Methanocaldococcus jannaschii* DSM 2661) | Thermophile, DSM 2661, taxon: 2190 |
| Mja Hyp-1 | *Methanococcus jannaschii* (*Methanocaldococcus jannaschii* DSM 2661) | Thermophile, DSM 2661, taxon: 2190 |
| Mja IF2 | *Methanococcus jannaschii* (*Methanocaldococcus jannaschii* DSM 2661) | Thermophile, DSM 2661, taxon: 2190 |
| Mja KlbA | *Methanococcus jannaschii* (*Methanocaldococcus jannaschii* DSM 2661) | Thermophile, DSM 2661, taxon: 2190 |
| Mja PEP | *Methanococcus jannaschii* (*Methanocaldococcus jannaschii* DSM 2661) | Thermophile, DSM 2661, taxon: 2190 |
| Mja Pol-1 | *Methanococcus jannaschii* (*Methanocaldococcus jannaschii* DSM 2661) | Thermophile, DSM 2661, taxon: 2190 |
| Mja Pol-2 | *Methanococcus jannaschii* (*Methanocaldococcus jannaschii* DSM 2661) | Thermophile, DSM 2661, taxon: 2190 |
| Mja RFC-1 | *Methanococcus jannaschii* (*Methanocaldococcus jannaschii* DSM 2661) | Thermophile, DSM 2661, taxon: 2190 |
| Mja RFC-2 | *Methanococcus jannaschii* (*Methanocaldococcus jannaschii* DSM 2661) | Thermophile, DSM 2661, taxon: 2190 |
| Mja RFC-3 | *Methanococcus jannaschii* (*Methanocaldococcus jannaschii* DSM 2661) | Thermophile, DSM 2661, taxon: 2190 |
| Mja RNR-1 | *Methanococcus jannaschii* (*Methanocaldococcus jannaschii* DSM 2661) | Thermophile, DSM 2661, taxon: 2190 |
| Mja RNR-2 | *Methanococcus jannaschii* (*Methanocaldococcus jannaschii* DSM 2661) | Thermophile, DSM 2661, taxon: 2190 |
| Mja RtcB (Mja Hyp-2) | *Methanococcus jannaschii* (*Methanocaldococcus jannaschii* DSM 2661) | Thermophile, DSM 2661, taxon: 2190 |
| Mja TFIIB | *Methanococcus jannaschii* (*Methanocaldococcus jannaschii* DSM 2661) | Thermophile, DSM 2661, taxon: 2190 |
| Mja UDP GD | *Methanococcus jannaschii* (*Methanocaldococcus jannaschii* DSM 2661) | Thermophile, DSM 2661, taxon: 2190 |
| Mja r-Gyr | *Methanococcus jannaschii* (*Methanocaldococcus jannaschii* DSM 2661) | Thermophile, DSM 2661, taxon: 2190 |
| Mja rPol A' | *Methanococcus jannaschii* (*Methanocaldococcus jannaschii* DSM 2661) | Thermophile, DSM 2661, taxon: 2190 |

TABLE 2-continued

Naturally Occurring Inteins

| Intein Name | Organism Name | Organism Description |
| --- | --- | --- |
| Mja rPol A" | *Methanococcus jannaschii* (*Methanocaldococcus jannaschii* DSM 2661) | Thermophile, DSM 2661, taxon: 2190 |
| Mka CDC48 | *Methanopyrus kandleri* AV19 | Thermophile, taxon: 190192 |
| Mka EF2 | *Methanopyrus kandleri* AV19 | Thermophile, taxon: 190192 |
| Mka RFC | *Methanopyrus kandleri* AV19 | Thermophile, taxon: 190192 |
| Mka RtcB | *Methanopyrus kandleri* AV19 | Thermophile, taxon: 190192 |
| Mka VatB | *Methanopyrus kandleri* AV19 | Thermophile, taxon: 190192 |
| Mth RIR1 | *Methanothermobacter thermautotrophicus* (*Methanobacterium thermoautotrophicum*) | Thermophile, delta H strain |
| Mvu-M7 Helicase | *Methanocaldococcus vulcanius* M7 | Taxon: 579137 |
| Mvu-M7 Pol-1 | *Methanocaldococcus vulcanius* M7 | Taxon: 579137 |
| Mvu-M7 Pol-2 | *Methanocaldococcus vulcanius* M7 | Taxon: 579137 |
| Mvu-M7 Pol-3 | *Methanocaldococcus vulcanius* M7 | Taxon: 579137 |
| Mvu-M7 UDP GD | *Methanocaldococcus vulcanius* M7 | Taxon: 579137 |
| Neq Pol-c | *Nanoarchaeum equitans* Kin4-M | Thermophile, taxon: 228908 |
| Neq Pol-n | *Nanoarchaeum equitans* Kin4-M | Thermophile, taxon: 228908 |
| Nma-ATCC43099 MCM | *Natrialba magadii* ATCC 43099 | Taxon: 547559 |
| Nma-ATCC43099 PolB-1 | *Natrialba magadii* ATCC 43099 | Taxon: 547559 |
| Nma-ATCC43099 PolB-2 | *Natrialba magadii* ATCC 43099 | Taxon: 547559 |
| Nph CDC21 | *Natronomonas pharaonis* DSM 2160 | taxon: 348780 |
| Nph PolB-1 | *Natronomonas pharaonis* DSM 2160 | taxon: 348780 |
| Nph PolB-2 | *Natronomonas pharaonis* DSM 2160 | taxon: 348780 |
| Nph rPol A" | *Natronomonas pharaonis* DSM 2160 | taxon: 348780 |
| Pab CDC21-1 | *Pyrococcus abyssi* | Thermophile, strain Orsay, taxon: 29292 |
| Pab CDC21-2 | *Pyrococcus abyssi* | Thermophile, strain Orsay, taxon: 29292 |
| Pab IF2 | *Pyrococcus abyssi* | Thermophile, strain Orsay, taxon: 29292 |
| Pab KlbA | *Pyrococcus abyssi* | Thermophile, strain Orsay, taxon: 29292 |
| Pab Lon | *Pyrococcus abyssi* | Thermophile, strain Orsay, taxon: 29292 |
| Pab Moaa | *Pyrococcus abyssi* | Thermophile, strain Orsay, taxon: 29292 |
| Pab Pol-II | *Pyrococcus abyssi* | Thermophile, strain Orsay, taxon: 29292 |
| Pab RFC-1 | *Pyrococcus abyssi* | Thermophile, strain Orsay, taxon: 29292 |
| Pab RFC-2 | *Pyrococcus abyssi* | Thermophile, strain Orsay, taxon: 29292 |
| Pab RIR1-1 | *Pyrococcus abyssi* | Thermophile, strain Orsay, taxon: 29292 |
| Pab RIR1-2 | *Pyrococcus abyssi* | Thermophile, strain Orsay, taxon: 29292 |
| Pab RIR1-3 | *Pyrococcus abyssi* | Thermophile, strain Orsay, taxon: 29292 |
| Pab RtcB (Pab Hyp-2) | *Pyrococcus abyssi* | Thermophile, strain Orsay, taxon: 29292 |
| Pab VMA | *Pyrococcus abyssi* | Thermophile, strain Orsay, taxon: 29292 |
| Par RIR1 | *Pyrobaculum arsenaticum* DSM 13514 | taxon: 340102 |
| Pfu CDC21 | *Pyrococcus furiosus* | Thermophile, taxon: 186497, DSM3638 |
| Pfu IF2 | *Pyrococcus furiosus* | Thermophile, taxon: 186497, DSM3638 |
| Pfu KlbA | *Pyrococcus furiosus* | Thermophile, taxon: 186497, DSM3638 |
| Pfu Lon | *Pyrococcus furiosus* | Thermophile, taxon: 186497, DSM3638 |
| Pfu RFC | *Pyrococcus furiosus* | Thermophile, DSM3638, taxon: 186497 |
| Pfu RIR1-1 | *Pyrococcus furiosus* | Thermophile, taxon: 186497, DSM3638 |
| Pfu RIR1-2 | *Pyrococcus furiosus* | Thermophile, taxon: 186497, DSM3638 |
| Pfu RtcB (Pfu Hyp-2) | *Pyrococcus furiosus* | Thermophile, taxon: 186497, DSM3638 |

TABLE 2-continued

Naturally Occurring Inteins

| Intein Name | Organism Name | Organism Description |
| --- | --- | --- |
| Pfu TopA | *Pyrococcus furiosus* | Thermophile, taxon: 186497, DSM3638 |
| Pfu VMA | *Pyrococcus furiosus* | Thermophile, taxon: 186497, DSM3638 |
| Pho CDC21-1 | *Pyrococcus horikoshii* OT3 | Thermophile, taxon: 53953 |
| Pho CDC21-2 | *Pyrococcus horikoshii* OT3 | Thermophile, taxon: 53953 |
| Pho IF2 | *Pyrococcus horikoshii* OT3 | Thermophile, taxon: 53953 |
| Pho KlbA | *Pyrococcus horikoshii* OT3 | Thermophile, taxon: 53953 |
| Pho LHR | *Pyrococcus horikoshii* OT3 | Thermophile, taxon: 53953 |
| Pho Lon | *Pyrococcus horikoshii* OT3 | Thermophile, taxon: 53953 |
| Pho Pol I | *Pyrococcus horikoshii* OT3 | Thermophile, taxon: 53953 |
| Pho Pol-II | *Pyrococcus horikoshii* OT3 | Thermophile, taxon: 53953 |
| Pho RFC | *Pyrococcus horikoshii* OT3 | Thermophile, taxon: 53953 |
| Pho RIR1 | *Pyrococcus horikoshii* OT3 | Thermophile, taxon: 53953 |
| Pho RadA | *Pyrococcus horikoshii* OT3 | Thermophile, taxon: 53953 |
| Pho RtcB (Pho Hyp-2) | *Pyrococcus horikoshii* OT3 | Thermophile, taxon: 53953 |
| Pho VMA | *Pyrococcus horikoshii* OT3 | Thermophile, taxon: 53953 |
| Pho r-Gyr | *Pyrococcus horikoshii* OT3 | Thermophile, taxon: 53953 |
| Psp-GBD Pol | *Pyrococcus* species GB-D | Thermophile |
| Pto VMA | *Picrophilus torridus*, DSM 9790 | DSM 9790, taxon: 263820, Thermoacidophile |
| Smar 1471 | *Staphylothermus marinus* F1 | taxon: 399550 |
| Smar MCM2 | *Staphylothermus marinus* F1 | taxon: 399550 |
| Tac-ATCC25905 VMA | *Thermoplasma acidophilum*, ATCC 25905 | Thermophile, taxon: 2303 |
| Tac-DSM1728 VMA | *Thermoplasma acidophilum*, DSM1728 | Thermophile, taxon: 2303 |
| Tag Pol-1 (Tsp-TY Pol-1) | *Thermococcus aggregans* | Thermophile, taxon: 110163 |
| Tag Pol-2 (Tsp-TY Pol-2) | *Thermococcus aggregans* | Thermophile, taxon: 110163 |
| Tag Pol-3 (Tsp-TY Pol-3) | *Thermococcus aggregans* | Thermophile, taxon: 110163 |
| Tba Pol-II | *Thermococcus barophilus* MP | taxon: 391623 |
| Tfu Pol-1 | *Thermococcus fumicolans* | Thermophilem, taxon: 46540 |
| Tfu Pol-2 | *Thermococcus fumicolans* | Thermophile, taxon: 46540 |
| Thy Pol-1 | *Thermococcus hydrothermalis* | Thermophile, taxon: 46539 |
| Thy Pol-2 | *Thermococcus hydrothermalis* | Thermophile, taxon: 46539 |
| Tko CDC21-1 | *Thermococcus kodakaraensis* KOD1 | Thermophile, taxon: 69014 |
| Tko CDC21-2 | *Thermococcus kodakaraensis* KOD1 | Thermophile, taxon: 69014 |
| Tko Helicase | *Thermococcus kodakaraensis* KOD1 | Thermophile, taxon: 69014 |
| Tko IF2 | *Thermococcus kodakaraensis* KOD1 | Thermophile, taxon: 69014 |
| Tko KlbA | *Thermococcus kodakaraensis* KOD1 | Thermophile, taxon: 69014 |
| Tko LHR | *Thermococcus kodakaraensis* KOD1 | Thermophile, taxon: 69014 |
| Tko Pol-1 (Pko Pol-1) | *Pyrococcus/Thermococcus kodakaraensis* KOD1 | Thermophile, taxon: 69014 |
| Tko Pol-2 (Pko Pol-2) | *Pyrococcus/Thermococcus kodakaraensis* KOD1 | Thermophile, taxon: 69014 |
| Tko Pol-II | *Thermococcus kodakaraensis* KOD1 | Thermophile, taxon: 69014 |
| Tko RFC | *Thermococcus kodakaraensis* KOD1 | Thermophile, taxon: 69014 |
| Tko RIR1-1 | *Thermococcus kodakaraensis* KOD1 | Thermophile, taxon: 69014 |
| Tko RIR1-2 | *Thermococcus kodakaraensis* KOD1 | Thermophile, taxon: 69014 |
| Tko RadA | *Thermococcus kodakaraensis* KOD1 | Thermophile, taxon: 69014 |
| Tko TopA | *Thermococcus kodakaraensis* KOD1 | Thermophile, taxon: 69014 |
| Tko r-Gyr | *Thermococcus kodakaraensis* KOD1 | Thermophile, taxon: 69014 |
| Tli Pol-1 | *Thermococcus litoralis* | Thermophile, taxon: 2265 |
| Tli Pol-2 | *Thermococcus litoralis* | Thermophile, taxon: 2265 |
| Tma Pol | *Thermococcus marinus* | taxon: 187879 |
| Ton-NA1 LHR | *Thermococcus onnurineus* NA1 | Taxon: 523850 |
| Ton-NA1 Pol | *Thermococcus onnurineus* NA1 | taxon: 342948 |
| Tpe Pol | *Thermococcus peptonophilus* strain SM2 | taxon: 32644 |
| Tsi-MM739 Lon | *Thermococcus sibiricus* MM 739 | Thermophile, Taxon: 604354 |
| Tsi-MM739 Pol-1 | *Thermococcus sibiricus* MM 739 | Taxon: 604354 |
| Tsi-MM739 Pol-2 | *Thermococcus sibiricus* MM 739 | Taxon: 604354 |
| Tsi-MM739 RFC | *Thermococcus sibiricus* MM 739 | Taxon: 604354 |
| Tsp AM4 RtcB | *Thermococcus* sp. AM4 | Taxon: 246969 |
| Tsp-AM4 LHR | *Thermococcus* sp. AM4 | Taxon: 246969 |
| Tsp-AM4 Lon | *Thermococcus* sp. AM4 | Taxon: 246969 |
| Tsp-AM4 RIR1 | *Thermococcus* sp. AM4 | Taxon: 246969 |
| Tsp-GE8 Pol-1 | *Thermococcus* species GE8 | Thermophile, taxon: 105583 |
| Tsp-GE8 Pol-2 | *Thermococcus* species GE8 | Thermophile, taxon: 105583 |
| Tsp-GT Pol-1 | *Thermococcus* species GT | taxon: 370106 |
| Tsp-GT Pol-2 | *Thermococcus* species GT | taxon: 370106 |
| Tsp-OGL-20P Pol | *Thermococcus* sp. OGL-20P | taxon: 277988 |
| Tthi Pol | *Thermococcus thioreducens* | Hyperthermophile |
| Tvo VMA | *Thermoplasma volcanium* GSS1 | Thermophile, taxon: 50339 |
| Tzi Pol | *Thermococcus zilligii* | taxon: 54076 |

TABLE 2-continued

Naturally Occurring Inteins

| Intein Name | Organism Name | Organism Description |
|---|---|---|
| Unc-ERS PFL | uncultured archaeon Gzfos13E1 | isolation_source = "Eel River sediment", clone = "GZfos13E1", taxon: 285397 |
| Unc-ERS RIR1 | uncultured archaeon GZfos9C4 | isolation_source = "Eel River sediment", taxon: 285366, clone = "GZfos9C4" |
| Unc-ERS RNR | uncultured archaeon GZfos10C7 | isolation_source = "Eel River sediment", clone = "GZfos10C7", taxon: 285400 |
| Unc-MetRFS MCM2 | uncultured archaeon (Rice Cluster I) | Enriched methanogenic consortium from rice field soil, taxon: 198240 |

The split inteins of the disclosed compositions or that can be used in the disclosed methods can be modified, or mutated, inteins. A modified intein can comprise modifications to the N-terminal intein segment, the C-terminal intein segment, or both. The modifications can include additional amino acids at the N-terminus the C-terminus of either portion of the split intein, or can be within the either portion of the split intein. Table 3 shows a list of amino acids, their abbreviations, polarity, and charge.

TABLE 3

Amino Acids

| Amino Acid | 3-Letter Code | 1-Letter Code | Polarity | Charge |
|---|---|---|---|---|
| Alanine | Ala | A | nonpolar | neutral |
| Arginine | Arg | R | Basic polar | positive |
| Asparagine | Asn | N | polar | neutral |
| Aspartic acid | Asp | D | acidic polar | negative |
| Cysteine | Cys | C | nonpolar | neutral |
| Glutamic acid | Glu | E | acidic polar | negative |
| Glutamine | Gln | Q | polar | neutral |
| Glycine | Gly | G | nonpolar | neutral |
| Histidine | His | H | Basic polar | Positive (10%) Neutral (90%) |
| Isoleucine | Ile | I | nonpolar | neutral |
| Leucine | Leu | L | nonpolar | neutral |
| Lysine | Lys | K | Basic polar | positive |
| Methionine | Met | M | nonpolar | neutral |
| Phenylalanine | Phe | F | nonpolar | neutral |
| Proline | Pro | P | nonpolar | neutral |
| Serine | Ser | S | polar | neutral |
| Threonine | Thr | T | polar | neutral |
| Tryptophan | Trp | W | nonpolar | neutral |
| Tyrosine | Tyr | Y | polar | neutral |
| Valine | Val | V | nonpolar | neutral |

Disclosed herein are vectors comprising nucleic acids encoding the C-terminal intein segment as disclosed herein, as well as cell lines comprising said vectors. As used herein, plasmid or viral vectors are agents that transport the disclosed nucleic acids, such as those encoding a C-terminal intein segment and a peptide of interest, into a cell without degradation and include a promoter yielding expression of the gene in the cells into which they can be delivered. In one example, a C-terminal intein segment and peptide of interest are derived from either a virus or a retrovirus. Retroviral vectors are able to carry a larger genetic payload, i.e., a transgene or marker gene, than other viral vectors and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes; they are thermostable and can be stored at room temperature. Disclosed herein is a viral vector which has been engineered so as to suppress the immune response of a host organism, elicited by the viral antigens. Vectors of this type can carry coding regions for Interleukin 8 or 10.

Viral vectors can have higher transfection (ability to introduce genes) abilities than chemical or physical methods to introduce genes into cells. Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

The fusion DNA encoding a modified peptide can be inserted into an appropriate expression vector, i.e., a vector which contains the necessary elements for the transcription and translation of the inserted protein-coding sequence. Depending on the host-vector system utilized, any one of a number of suitable transcription and translation elements can be used. For instance, when expressing a modified eukaryotic protein, it can be advantageous to use appropriate eukaryotic vectors and host cells. Expression of the fusion DNA results in the production of a modified protein.

Also disclosed herein are cell lines comprising the vectors or peptides disclosed herein. A variety of cells can be used with the vectors and plasmids disclosed herein. Non-limiting examples of such cells include somatic cells such as blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used, as can the progenitors, precursors and stem cells that give rise to the above-described somatic and germ cells. These cells, tissues and organs can be normal, or they can be pathological such as those involved in diseases or physical disorders, including, but not limited to, infectious diseases (caused by bacteria, fungi yeast, viruses (including HIV, or parasites); in genetic or biochemical pathologies (e.g., cystic fibrosis, hemophilia, Alzheimer's disease, schizophrenia, muscular dystrophy, multiple sclerosis, etc.); or in carcinogenesis and other cancer-related processes.

The eukaryotic cell lines disclosed herein can be animal cells, plant cells (monocot or dicot plants) or fungal cells, such as yeast. Animal cells include those of vertebrate or invertebrate origin. Vertebrate cells, especially mammalian cells (including, but not limited to, cells obtained or derived from human, simian or other non-human primate, mouse, rat, avian, bovine, porcine, ovine, canine, feline and the like), avian cells, fish cells (including zebrafish cells), insect cells (including, but not limited to, cells obtained or derived from *Drosophila* species, from *Spodoptera* species (e.g., Sf9 obtained or derived from *S. frugiperida*, or HIGH FIVE™ cells) or from *Trichoplusa* species (e.g., MG1, derived from *T. ni*)), worm cells (e.g., those obtained or derived from *C. elegans*), and the like. It will be appreciated by one of skill in the art, however, that cells from any species besides those specifically disclosed herein can be advantageously used in accordance with the vectors, plasmids, and methods disclosed herein, without the need for undue experimentation.

Examples of useful cell lines include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (see Van der Buick, A. M. et al., Cancer Res. 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171 can also be used. Other mammalian cells and cell lines can be used in accordance with the present invention, including, but not limited to CHO cells, COS cells, VERO cells, 293 cells, PER-C6 cells, M1 cells, NS-1 cells, COS-7 cells, MDBK cells, MDCK cells, MRC-5 cells, WI-38 cells, WEHI cells, SP2/0 cells, BHK cells (including BHK-21 cells); these and other cells and cell lines are available commercially, for example from the American Type Culture Collection (P.O. Box 1549, Manassas, Va. 20108 USA). Many other cell lines are known in the art and will be familiar to the ordinarily skilled artisan; such cell lines therefore can be used equally well.

Once obtained, the proteins of interest can be separated and purified by appropriate combination of known techniques. These methods include, for example, methods utilizing solubility such as salt precipitation and solvent precipitation; methods utilizing the difference in molecular weight such as dialysis, ultra-filtration, gel-filtration, and SDS-polyacrylamide gel electrophoresis; methods utilizing a difference in electrical charge such as ion-exchange column chromatography; methods utilizing specific affinity such as affinity chromatography; methods utilizing a difference in hydrophobicity such as reverse-phase high performance liquid chromatography; and methods utilizing a difference in isoelectric point, such as isoelectric focusing electrophoresis. These are discussed in more detail below.

Disclosed is a method of purifying a protein of interest, the method comprising: utilizing a split intein comprising two separate peptides: an N-terminal intein segment and a C-terminal intein segment; immobilizing the N-terminal intein segment to a solid support; attaching a protein of interest to the C-terminal intein segment, wherein cleaving of the C-terminal intein segment is highly sensitive to extrinsic conditions when compared to a native intein. exposing the N-terminal intein segment and the C-terminal intein segment to each other so that they associate; washing the solid support to remove non-bound material; placing the associated the N-terminal intein segment and the C-terminal intein segment under conditions that allow for the intein to self-cleave; and isolating the protein of interest.

Also disclosed herein are kits. A kit, for example, can include the split intein disclosed herein (an N-terminal intein segment and a C-terminal intein segment) as well as a protein of interest, optionally. The kit can also include instructions for use.

C. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Modifications to Control the Npu Split Intein C-Terminal Cleaving Reaction To efficiently control C-terminal cleavage of the $Npu_C$ intein segment, the highly conserved penultimate Serine of $Npu_C$ was modified into Histidine, which is the residue found at this position in most inteins. The penultimate Histidine can stabilize the cyclization of the C-terminal intein Asparagine through hydrogen bonding, and can contribute to the pH sensitivity of some contiguous inteins. The resulting S34H $Npu_C$ mutant, $Npuc^{HN}$ was fused with Streptokinase as the test target protein for testing its cleaving behavior under various conditions. Furthermore, a modification of the +1 residue of Streptokinase was also investigated. The native +1 residue of Streptokinase is a Cysteine, which is a typical +1 extein residue that facilitates intein splicing or cleaving reactions. Since most recombinant proteins, especially the therapeutic proteins that are manufactured in mammalian cells usually start with a methionine as their +1 residue, we made a C1M mutant, namely $SK^M$ for testing the intein cleaving reaction adaptability.

The cleaving kinetics of the different mutants were initially studied in solution. The $Npu_N$ and the $Npu_C^{HN}$ mutants were expressed in *E. coli* and first purified using Ni-NTA affinity methods. To ensure a complete cleaving reaction of $Npu_C^{HN}$, a 2:1 molar ratio of $Npu_N$:$Npu_C^{HN}$ was used for all reactions. The cleaving reaction was carried out at room temperature at either pH 8.5 or pH 6.2. The mixture was sampled over 16 hours and the reaction was terminated by adding SDS-PAGE protein loading dye (375 mM Tri-HCl, 9% SDS, 50% Glycerol, 0.03% Bromophenol blue and 5% β-mercaptoethanol). The results shown in FIG. 23 indicate that the S34H mutation did not induce a notable pH sensitivity in comparison to the wild type $Npu_C$. Nevertheless, the penultimate Histidine residue seemed to accelerate the cleaving rate for both the $SK^C$ and $SK^M$ target proteins. Furthermore, the +1 Cysteine ($SK^C$) cleaved faster than the +1 Methionine ($SK^M$), as expected. The $Npuc^{HN}$-$SK^C$ mutant showed the fastest cleaving rate among the four mutants at both pH conditions. The cleaving percentage was over 50% in an hour at pH 8.5 and nearly to completion within 5 hours. However, the Histidine mutation failed to enhance the pH sensitivity, and therefore the $Npu_C^{HN}$ segment is not suitable as a controllable split intein module when combined with $Npu_N$(C.F.).

To enhance the sensitivity of the cleaving reaction to zinc ion and pH, the 04b Zinc-Binding Motif sequence (also referred to herein as a Sensitivity Enhancing Motif) (GDGHG, SEQ ID NO: 17) was engineered onto N-terminus of the $Npu_N$ (C.F.) intein segment as a "sensitivity enhancing motif", resulting in the intein referred to as Zn-$Npu_N$. Hypothetically, the Zinc-Binding Motif should largely enhance the sensitivity of the split intein system to zinc. Therefore, to obtain inhibition of cleaving small amounts of zinc ion would be required. To demonstrate this idea, the same cleaving kinetic study with zinc titration at pH 8.5 and 6.2 was carried out using Zn-$Npu_N$ at room temperature.

FIG. 24 shows the cleaving results of Zn-$Npu_N$ with all four Npuc-SK mutants ($SK^M$ and $SK^C$ with and without the HN mutation). The cleaving reactions of the four $Npu_C$ mutants were all effectively inhibited at pH 8.5 even in the absence of $ZnCl_2$. More interestingly, the cleaving activity was reversibly restored when shifting the pH to 6.2 but only with the $Npu_C^{HN}$ mutants. At pH 6.2, $Npu_C^{HN}$-$SK^C$ and $Npu_C^{HN}$-$SK^M$ still revealed a gradient response to zinc titration, while the wild type $Npu_C$ remained inactive.

A more detailed analysis is shown in FIG. 25. The cleaving reactions were all carried out in the absence of $ZnCl_2$ and simply controlled by pH. The samples were collected over 16 hours, and at each time point the cleaving reaction was terminated by mixing with SDS-PAGE protein loading dye. As shown in the results, the combination of Zn-$Npu_N$ with $Npu_C^{HN}$-$SK^M$ or $Npu_C^{HN}$-$SK^C$ exhibited pH sensitivity for C-terminal cleavage, while the wild type $Npu_C$ had no obvious differences. Thus, the Zinc-Binding Motif sequence (GDGHG SEQ ID NO: 17) serves as a highly effective "sensitivity enhancing motif" for pH-dependent cleaving of $Npu_C^{HN}$ in combination with Zn-$Npu^N$.

A noteworthy point was that the $Npuc^{HN}$-$SK^M$ tended to cleave faster than the $Npuc^{HN}$-$SK^C$. This can imply that the Zinc-Binding Motif not only contributed to the pH sensitivity but also affected the nucleophilic attack at the +1 extein residue. Nevertheless, Methionine is the main beginning residue of most recombinant proteins, so the success with the $SK^M$ mutant is encouraging for the application of this strategy to other target proteins.

a. Materials and Methods (a) Plasmid Construction of $Npu_N$ (Cysteine-Free) and Zn-$Npu_N$ To silence the native cysteine residues of the $Npu_N$ intein segment, Cys29 and Cys60 were both mutated into serine, while Cys1 was mutated into Ala, resulting in the $Npu_N$ (cysteine-free, or C.F.). A zinc binding motif (GDGHG, SEQ ID NO: 17) was encoded directly onto a PCR primer to PCR-amplify the $Npu_N$ (cysteine-free) gene, resulting in the Zn-$Npu_N$ intein segment. Two unique restriction enzyme sites: NdeI and XhoI were designed at the 5' and 3' end, respectively, of $Npu_N$ (C.F.) and Zn-$Npu_N$. The PCR products were digested with the two unique enzymes and then ligated into a pET vector for protein expression in E. coli.

(b) Plasmid Construction of $Npu_C$ or $NpuC^{HN}$ Tagged Target Proteins for E. coli and IVT Expression The $Npu_C$ or $Npu_C^{HN}$ split intein segment and the $SK^M$ and $SK^C$ target protein genes were fused through overlap PCR. Two unique restriction enzymes: NdeI and XhoI were designed at 5'- and 3'-end of the PCR product, respectively. The PCR-amplified fusion protein genes were digested with NdeI and XhoI and ligated into a pET expression vector for E. coli expression.

(c) Recombinant Protein Expression in E. coli

The constructed intein segment fusion plasmids were transformed into the Escherichia coli strain BLR(DE3) (F-ompT hsdSB(rB-,mB-) gal dcm (DE3)). Transformed cells were cultured in 5 ml Luria Broth media (10 g NaCl, 5 g Yeast extract, 10 g Tryptone per liter) supplemented with 100 µg/ml ampicillin, vigorously shaken at 37° C., 200 rpm for 16-18 hours. Overnight cultures were then diluted at a ratio of 1:100 (v/v) into 2× Luria Broth media (10 g NaCl, 10 g Yeast extract, 20 g Tryptone per liter) supplemented with 100 µg/ml ampicillin, and shaken at 37° C., 200 rpm until reaching the $OD_{600}$ of 0.6-0.8. The cells were then induced for protein expression by adding isopropyl β-D-1-thiogalactopyranoside (IPTG) at a final concentration 0.4 mM. The expression was carried out at 16° C. for 24 hours.

2. Example 2: Covalent Immobilization of $Npu_N$ (Cysteine-Free)

Figure 2B:
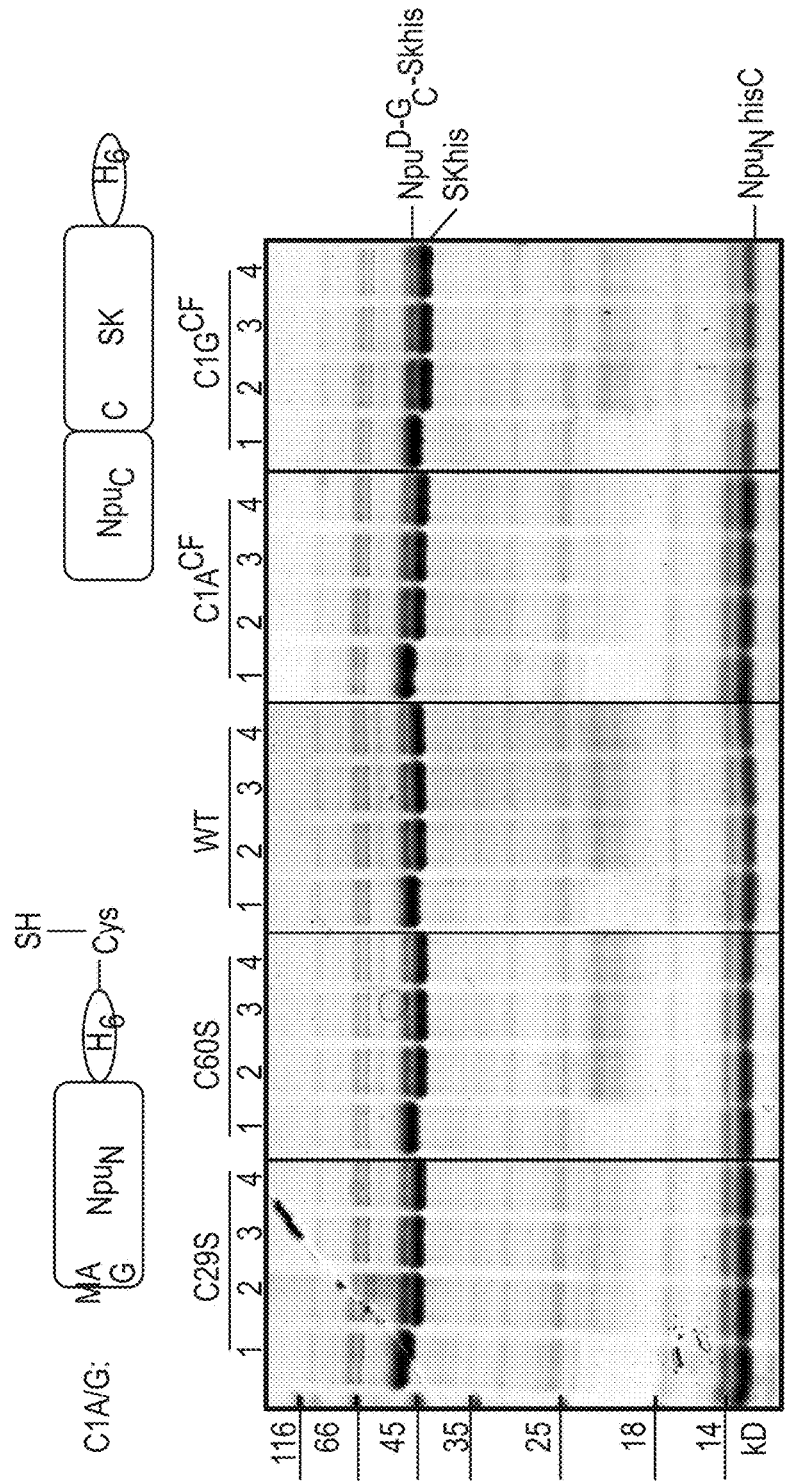
Figure 3A:
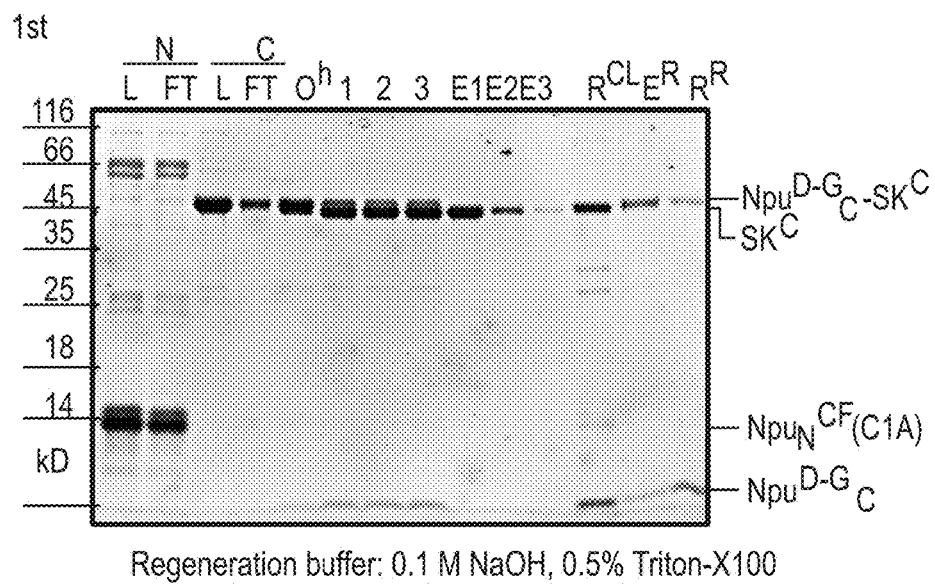
FIGS. 3A and 3B show the characterization of the covalent, immobilized intein resin being used to purify the example SK target protein.
Figure 3B:
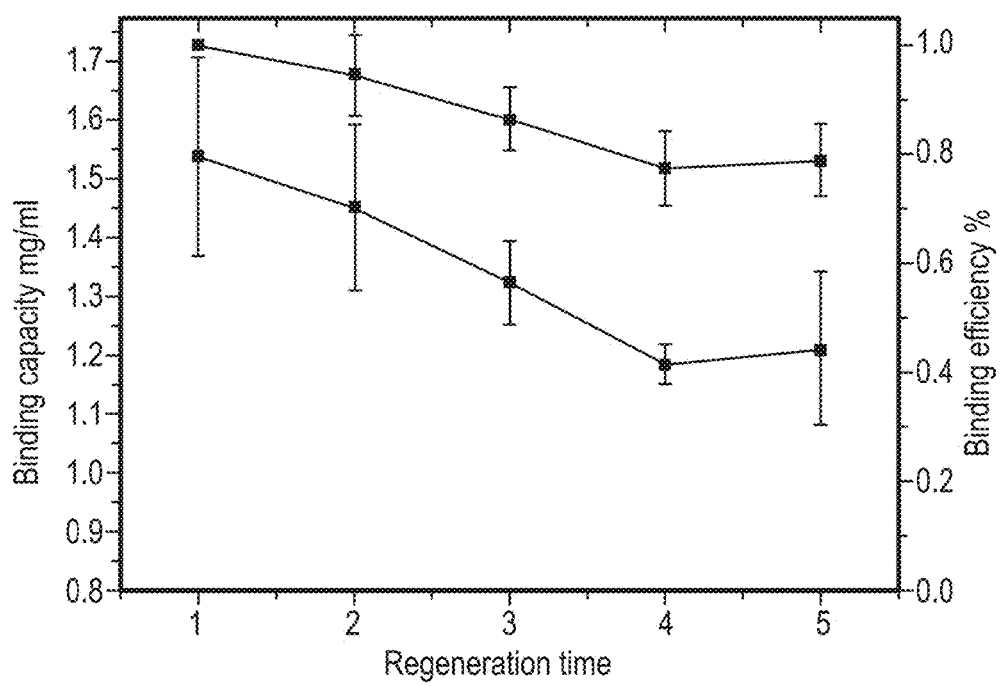
Figure 4:
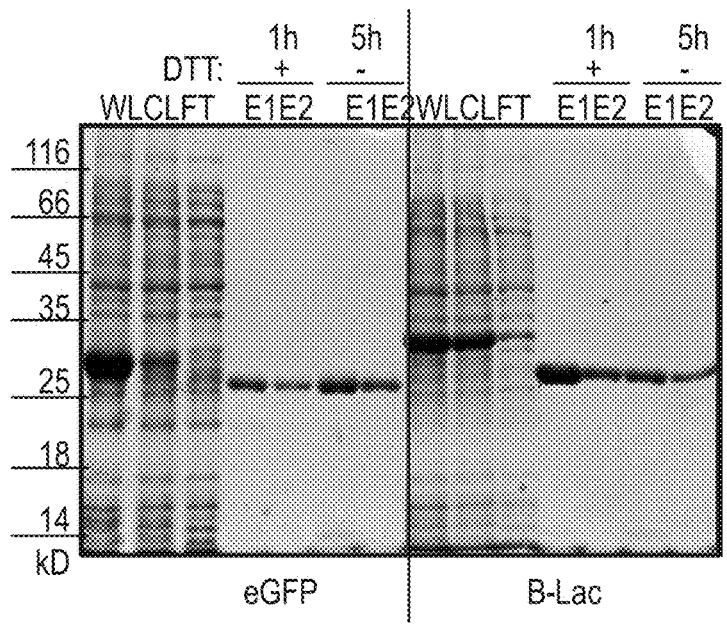
FIG. 4 shows the purification of two additional example targets (eGFP=enhanced green fluorescent protein; B-Lac=beta lactamase) directly from a bacterial expression lysate. Bacterial cells overexpressing each fusion protein (the Npuc intein segment joined to the example target) are lysed in a lysis buffer. Overexpressed fusion proteins are clearly visible as heavy bands in the WL and CL lanes at the left of eah gel. The clarified lysates are then diluted in an appropriate binding buffer and directly flowed through the pre-packed $Npu_N^{CF}$ covalently immobilized intein resin column as above at a flow rate of 0.5 ml/min. The contaminants are then washed out using clean binding buffer, and the intein is induced to cleave off the target either with 50 mM DTT at RT for 1 hour (DTT+), or without DTT (DTT−) at 37° C. for 5 hours. KEY: WL, whole lysate; CL, clarified lysate; FT, flow-through; E1, E2, elution fractions collected after cleaving has occurred. Note that the recovered, tagless target proteins are slightly smaller in size than the tagged target protein bands appearing in the WL and CL lanes.
Figure 5:
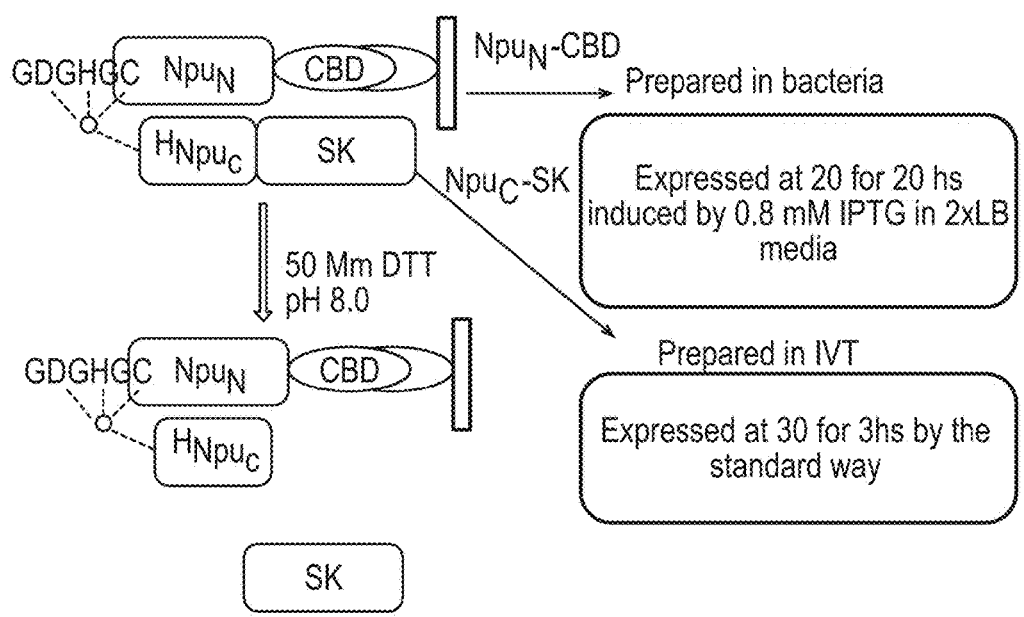
FIG. 5 shows application of the fast split intein to the purification of the example SK target protein expressed in an in vitro translation (IVT) expression system. In this case, the N-terminal intein segment is immobilized by fusion to a conventional chitin-binding domain (CBD) affinity tag and association onto a commercially available chitin resin. The sequence GDGHGC preceding the intein is the sensitivity-enhancing motif described later in this patent. Intein association, washing and cleaving take place as with the covalently immobilized intein described in FIG. 3.

To create an $Npu_N$ intein that exhibits uniform orientation upon immobilization, the three cysteine residues in $Npu_N$ were first mutated to serine or alanine at Cys 29, Cys 60 and Cys1. Since the potential impacts of theses mutations on the cleaving activity was unknown, the cleaving behavior of the individual mutants were investigated, and the results were compared to the wild type $Npu_N$. In FIG. 2B, $Npu_C$-$SK^M$ was mixed with various $Npu_N$ mutants in solution and then incubated at room temperature for an hour to allow C-terminal cleavage. The three $Npu_N$ mutants, C29S, C60S and $Npu_N$ (C.F.) behaved similarly to the wild type $Npu_N$ under all three cleaving conditions, indicating that the mutation of cysteine to serine at any of the locations did not alter the cleaving properties. Consequently, we confirmed the feasibility of using $Npu_N$ (C.F.) as our immobilization target and $Npu_N$ (C.F) was used as a parent intein for all characterization studies.

The $Npu_N$ (C.F.) was immobilized to an agarose-based SulfoLink resin through a thiol-ether bonding, as described in the materials and methods session. The pre-purified $Npu_N$ was quantified using Bradford assay before immobilization. To evaluate the efficiency and capacity of the covalent immobilization, various amounts of $Npu_N$ were loaded to multiple chromatographic columns, where 1 ml of Sulfo-Link resin was packed individually. The unbound proteins in the flow-through sample and washes were collected and quantified using Bradford assays. An estimation of the immobilization efficiency could thus be calculated using the amount of loaded protein and subtracting the amount of proteins in the flow-through and wash. As shown in Table 4, the approximate average amount of immobilized $Npu_N$ on SulfoLink resin was 2.88 mg/ml.

TABLE 4

Npu$_N$ (C.F.) immobilization test
Table 4. The immobilization efficiency calculation.
All protein samples were quantified using Bradford assay.

| Loaded (mg) | 15.0 | 10.0 | 5.0 | 2.5 |
|---|---|---|---|---|
| Flow-through and Wash (mg) | 11.2 | 7.2 | 2.2 | 0.4 |
| Binding (mg/ml) | 3.8 | 2.8 | 2.8 | 2.1 |

Average of Immobilized NpuN (C.F.) on SulfoLink Resin: 2.88 mg/ml

The immobilized Npu$_N$ resin was then tested for its binding capacity. Npu$_C$-SK$^M$ was used as the model protein for examining the purification module. *E. coli* expressed Npuc-SK$^M$ was pre-purified using Ni-NTA and quantified using Bradford assay. Various amounts of Npu$_C$-SK$^M$ were loaded to the Npu$_N$ resin-packed columns, which allowed the binding of Npu$_C$-SK$^M$. The unbound proteins in the flow-through sample and the wash sample were collected and quantified using Bradford assay. The result showed an approximate 2.3 mg/ml of binding capacity of the Npu$_N$ resin (Table 5).

TABLE 5

Npu$_N$ (C.F.) Resin Capacity test
The binding capacity of Npu$_N$-SulfoLink resin. Various amounts of Npu$_C$-SK$^M$ were loaded to multiple chromatographic columns where 0.2 ml of Npu$_N$-SulfoLink resin was packed individually. The residuals collected in flow-through and wash samples were quantified by Bradford assay.

| Loaded (μg) | 1200 | 600 | 400 | 100 | 50 |
|---|---|---|---|---|---|
| Flow-through and Wash (μg) | 628.1 | 147.8 | 29.5 | 2.2 | Undetectable |
| Binding Percentage (%) | 47.6% | 75.4% | 92.7% | 97.8% | 100% |
| Binding (mg/ml) | 2.86 | 2.26 | 1.85 | N/A | N/A |

Average Capacity of NpuN (C.F.)-SulfoLink Resin: 2.32 ± 0.5 mg/ml a. Materials and Methods (a) Plasmid Construction of Npu$_N$ (Cysteine-Free) and Zn-Npu$_N$ To silence the native cysteine residues of the NpuN intein segment, Cys29 and Cys60 were both mutated into serine, while Cys1 was mutated into Ala, resulting in the Npu$_N$ (cysteine-free, or C.F.). A zinc binding motif (GDGHG, SEQ ID NO: 17) was encoded directly onto a PCR primer to PCR-amplify the Npu$_N$ (cysteine-free) genes, resulting in the Zn-Npu$_N$ intein segment. To add an additional His tag and cysteine residues to the C-terminus of Npu$_N$, overlap PCR was used according to conventional methods. Two unique restriction enzyme sites: NdeI and XhoI were designed at the 5' and 3' end, respectively, of Npu$_N$ (C.F.) and Zn-Npu$_N$. The PCR products were digested with the two unique enzymes and then ligated into a pET vector for protein expression in *E. coli*. The expressed Npu$_N$ intein segment is shown as SEQ ID #3.

(b) Recombinant Protein Expression in *E. coli*

The constructed intein segment fusion plasmids were transformed into the *Escherichia coli* strain BLR(DE3) (F-ompT hsdSB(rB-,mB-) gal dcm (DE3)). Transformed cells were cultured in 5 ml Luria Broth media (10 g NaCl, 5 g Yeast extract, 10 g Tryptone per liter) supplemented with 100 μg/ml ampicillin, vigorously shaken at 37° C., 200 rpm for 16-18 hours. Overnight cultures were then diluted at a ratio of 1:100 (v/v) into 2x Luria Broth media (10 g NaCl, 10 g Yeast extract, 20 g Tryptone per liter) supplemented with 100 μg/ml ampicillin, and shaken at 37° C., 200 rpm until reaching the OD$_{600}$ of 0.6-0.8. The cells were then induced for protein expression by adding isopropyl τ3-D-1-thiogalactopyranoside (IPTG) at a final concentration 0.4 mM. The expression was carried out at 16° C. for 24 hours.

(c) Covalent Immobilization of Npu$_N$ (Cysteine-Free)

The Npu$_N$ was immobilized through the interaction between the sulfhydryl group of the engineered cysteine at the C-terminus of Npu$_N$ (SEQ ID NO: 3) and the Iodoacetyl group on a beaded agarose support. The agarose coupling bead was purchased from Thermo Scientific (SulfoLink Coupling Resin, #20401). The Iodoacetyl groups on the SulfoLink Coupling Resin react specifically with free sulfhydryls, as shown in the FIG. 2. The 12-atom spacer arm minimizes steric hindrance, ensuring efficient binding interactions with the coupled molecule. This resin is ideal for conjugating peptides or proteins and can immobilize approximately one milligram sulfhydryl-containing peptide per milliliter of settled resin.

To make a 1 ml of Npu$_N$-SulfoLink resin, about 50-60 ml of *E. coli* expressed Npu$_N$ (cysteine-free) was pre-purified using Ni-NTA and dissolved in 1 ml of Coupling Buffer (50 mM Tris, 5 mM EDTA-Na; pH 8.5). A final concentration 25 mM of Tris (2-carboxyethyl) phosphine (TCEP, Thermo Product No. 77720), was added to the Npu$_N$ (cysteine-free) to remove the excess disulfide bonds. The SulfoLink resin slurry was first transferred to a chromatographic column and allowed to settle to obtain a 1 ml bed volume. The column was then equilibrated with 10 column-volume of Coupling Buffer before immobilization. To couple the Npu$_N$, 1 ml of dissolved protein was added to 1 ml SulfoLink resin and mixed by gently shaking for at least an hour at room temperature or for 16 hours at 4° C. After the covalent immobilization, the resin was washed with another 10 column-volumes of Coupling Buffer to remove the unbound Npu$_N$. The coupling resin was then incubated in a 50 mM L-Cysteine-HCl in Coupling Buffer for an hour to block the nonspecific binding sites on the agarose beads. Lastly, 1M NaCl was used to rinse out the residual conatimants on the resin. The final Npu$_N$-coupling resin was stored in 20% ethanol at 4° C.

3. Example 3: Recombinant Protein Purification Using Zn-Npu$_N$ Resin with pH-Controlled Cleavage Given the promising pH sensitivity property of using Zn-Npu$_N$ and Npuc$^{HN}$ as a purification module (Example 1), the applicability of this split intein system was evaluated for on-column purification of several target proteins. The Zn-Npu$_N$ segment was immobilized onto the agarose-based SulfoLink resin as described previously (Example 2). The purification scheme relies on a pH 8.5 buffer for inhibiting C-terminal cleavage during purification, and a pH 6.2 buffer for induction of cleaving after purification. On-column purification of proteins expressed in three different host cell systems: *E. coli*, an IVT system, and a mammalian cell expression system was used.

Figure 8:
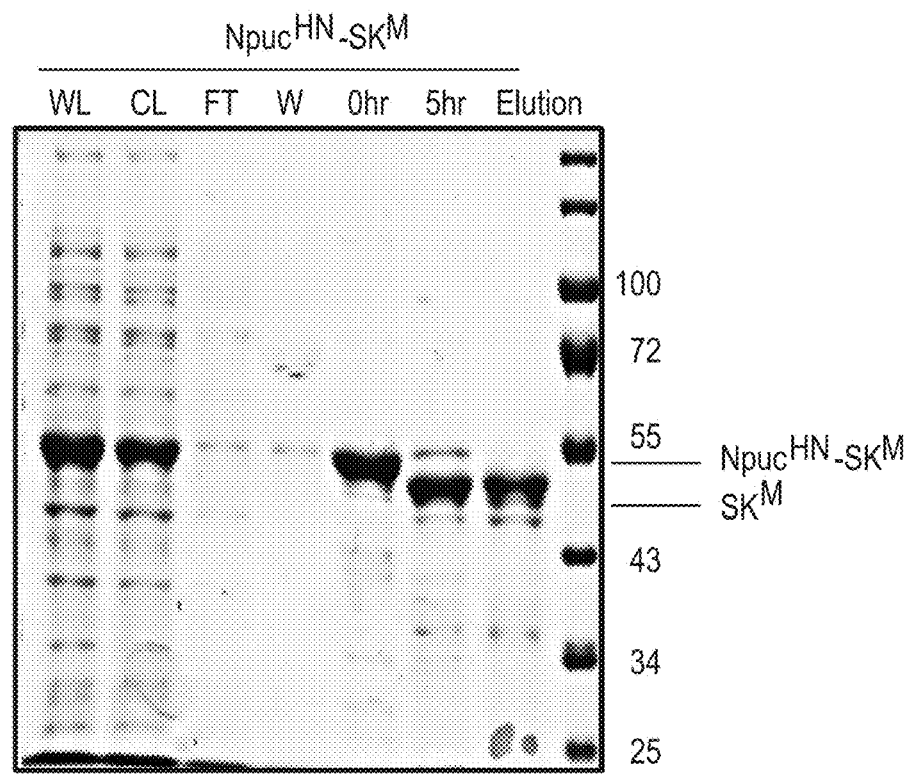
FIG. 8 shows that a C-terminal intein segment with a serine to histidine mutation ($Npu_c^{HN}$) was expressed in fusion to the streptokinase test protein ($SK^M$), which was then purified using an N-terminal intein segment with a sensitivity-enhancing motif ($Zn-Npu_N$). In this case, $SK^M$ notation refers to the SK target protein with the native methionine as the first amino acid. The target protein ($SK^M$) was properly cleaved and separated (lane 'Elute'). Specifically, $Npu_c^{HN}$-$SK^M$ was expressed in a 20 ml culture of the E. coli expression strain BLR, and was then purified directly from the clarified cell lysate using 500 μl of immobilized $Zn-Npu_N$ SulfoLink™ resin. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2.
Figure 9:
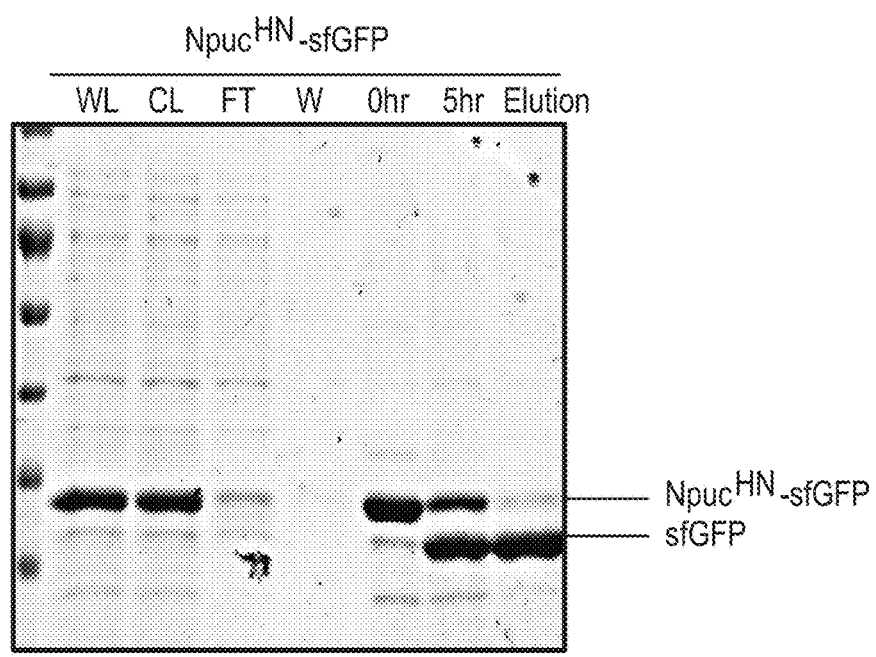
FIG. 9 shows a C-terminal intein segment with a serine to histidine mutation ($Npu_c^{HN}$) expressed with sfGFP (superfolder green fluorescent protein), which was then purified on-column as above. Specifically, $Npu_c^{HN}$-sfGFP was expressed in a 50 ml culture of the E. coli expression strain BLR, and was then purified using 500 μl of the immobilized $Zn-Npu_N$ SulfoLink™ resin. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2. Cleaving occurred at room temperature.
Figure 10:
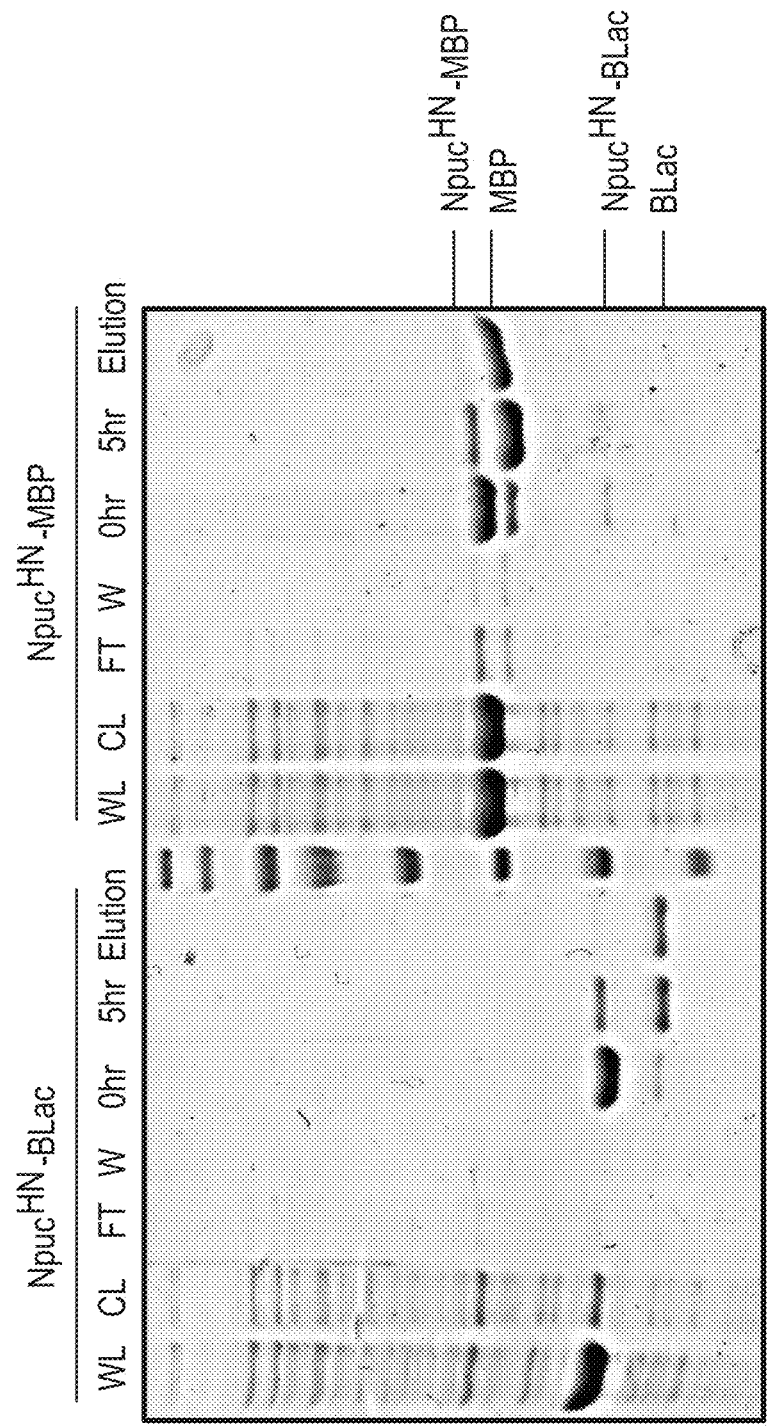
FIG. 10 shows a C-terminal intein segment with a serine to histidine mutation ($Npu_c^{HN}$) expressed with β-Lactamase (β-Lac) and with maltose binding protein (MBP) as test target proteins, which were then purified on-column as above. Specifically, $Npu_c^{HN}$-β-Lac and $Npu_c^{HN}$-MBP were expressed in 50 ml of recombinant E. coli BLR cells, and then purified using 500 μl of the $Zn-Npu_N$ SulfoLink™ resin. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2.
Figure 11:
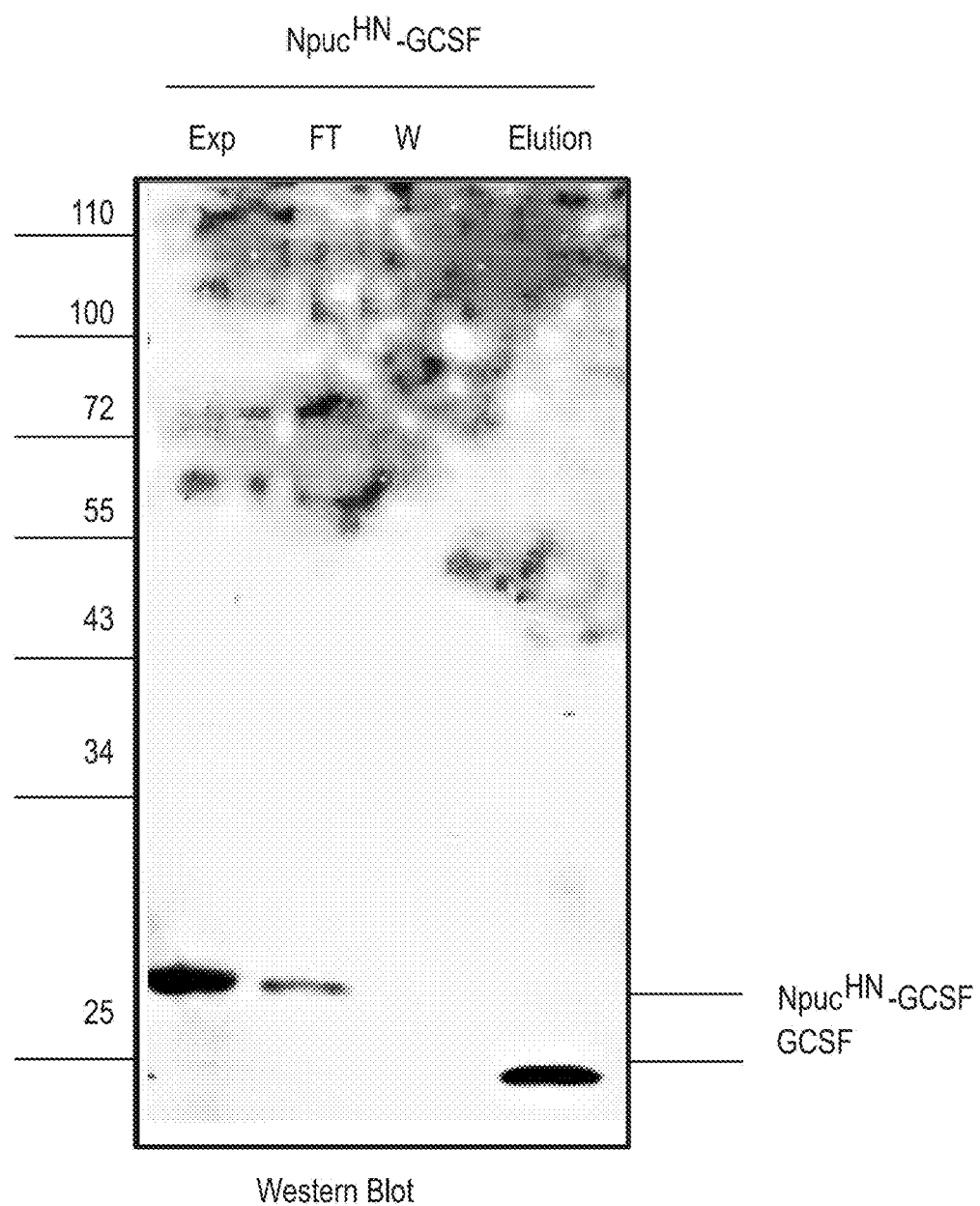
FIG. 11 shows expression and purification of granulocyte-colony stimulating factor (G-CSF, also known as Neupogen) using a C-terminal intein segment with a serine to histidine mutation ($Npu_c^{HN}$). In this case, the protein was expressed in a 400 μL IVT (in vitro translation) reaction (CHO-IVT) for 16 hours at 30° C. G-CSF was purified using 200 μL of the $Zn-Npu_N$ SulfoLink™ immobilization resin. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2. The intein cleaving reaction occurred at room temperature for 5 hours, and the products were analyzed by Western blot using an anti-GCSF antibody.
Figure 12:
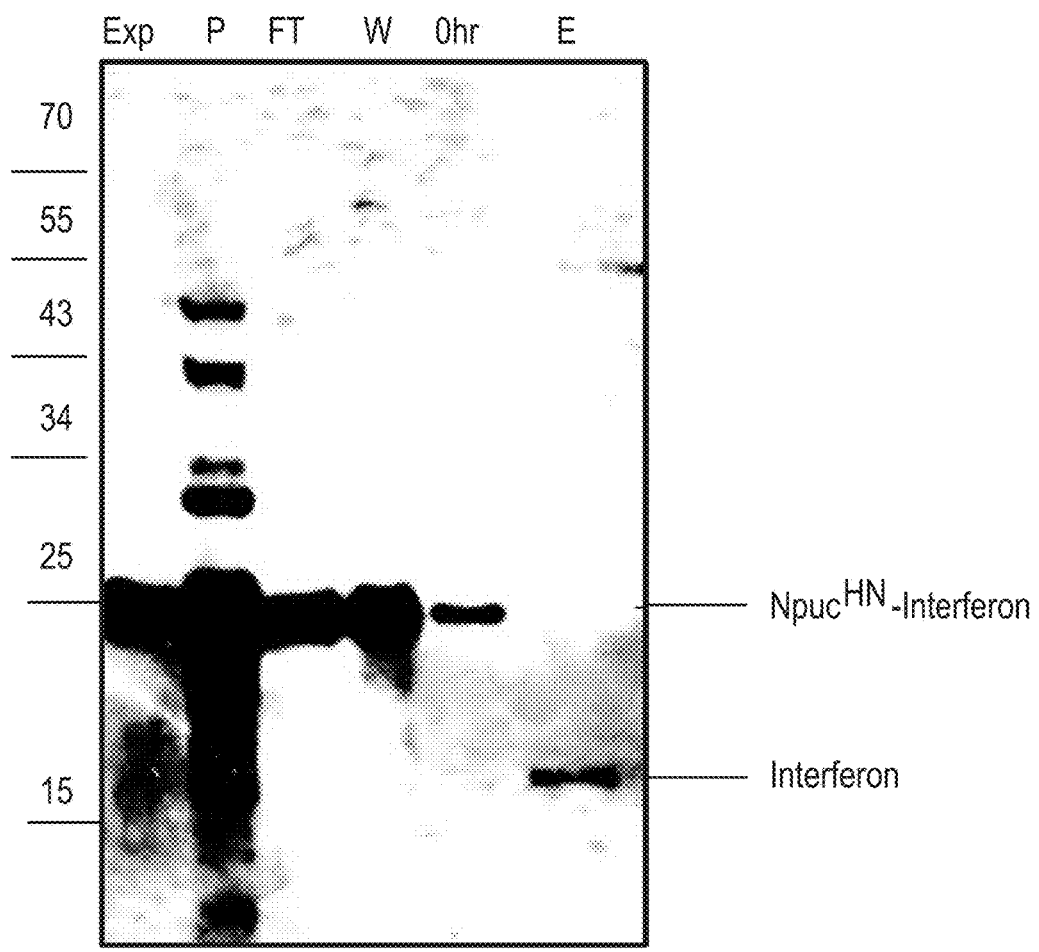
FIG. 12 shows expression and purification of the test target protein interferon in CHO-IVT using a C-terminal intein segment with a serine to histidine mutation ($Npu_c^{HN}$). As above with G-CSF, a 400 μL IVT reaction was used to express the $Npu_c^{HN}$-tagged interferon for 16 hours at 30° C. Interferon was purified using 200 μL of the $Zn-Npu_N$ SulfoLink™ immobilization resin. A binding/washing buffer of 20 mM AMPD/PIPES and 500 mM NaCl was used, with a pH of 8.5. The cleaving buffer used was 20 mM AMPD/PIPES and 500 mM NaCl with a pH of 6.2. The intein cleaving reaction occurred at room temperature for 5 hours.
Figure 13A:
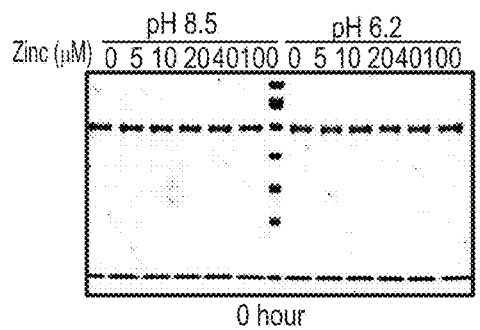
FIGS. 13A-E shows the cleaving kinetics of C-terminal intein segment ($Npu_c$) fused to the target protein streptokinase ($SK^M$), and N-terminal intein segment with a sensitivity-enhancing motif ($Zn-Npu_N$), as a function of pH and zinc concentration at room temperature. The intein protein segments were expressed in E. coli (BLR culture), and then purified using Ni-NTA affinity chromatography. The purified $Zn-Npu_N$ and $Npu_c$-$SK^M$ segments were then mixed in solution at a molar ratio of 2:1, respectively. Cleaving occurred at room temperature. The buffer used was 20 mM AMPD/PIPES, and 500 mM NaCl, with the pH adjusted using NaOH or HCl as needed.
Figure 13B:
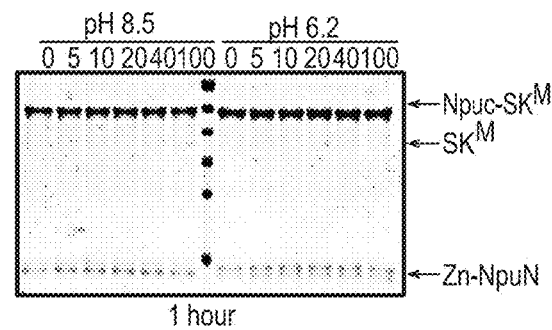
Figure 13C:
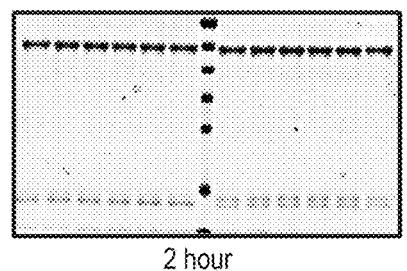
Figure 13D:
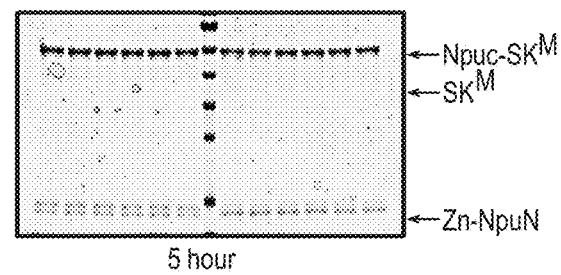
Figure 13E:
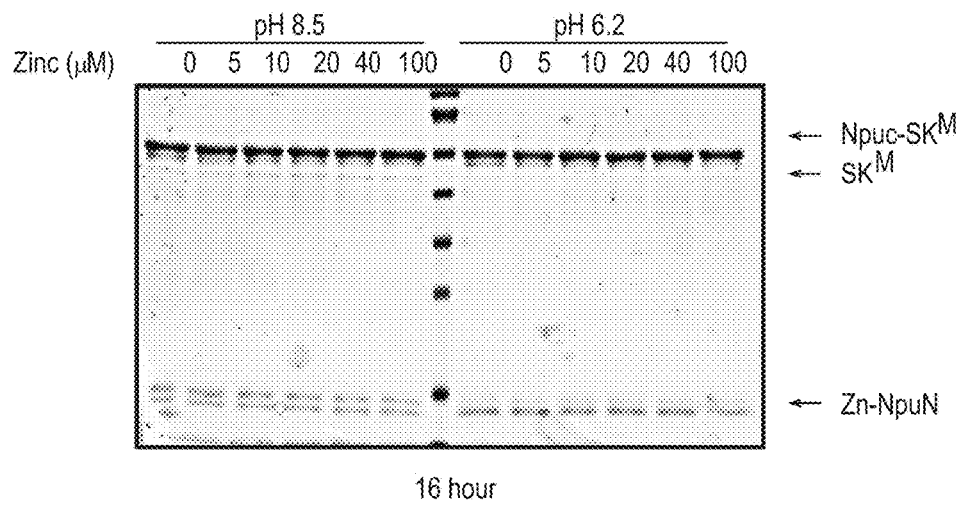
Figure 14A:
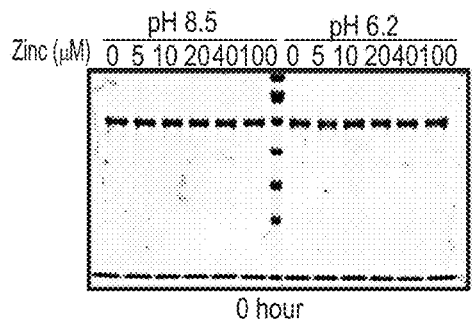
FIGS. 14A-E show the cleaving kinetics of a C-terminal intein segment ($Npu_c$) and the target protein streptokinase (SK$^C$), using an N-terminal intein segment with a sensitivity-enhancing motif (Zn-Npu$_N$), as a function of pH and zinc concentration at room temperature. The intein protein segments were expressed in *E. coli* (BLR culture), and then purified using Ni-NTA affinity chromatography. The purified Zn-Npu$_N$ and Npu$_C$-SK$^C$ segments were then mixed in solution at a molar ratio of 2:1, respectively. Cleaving occurred at room temperature. The buffer used was 20 mM AMPD/PIPES, and 500 mM NaCl, with the pH adjusted using NaOH or HCl as needed.
Figure 14B:
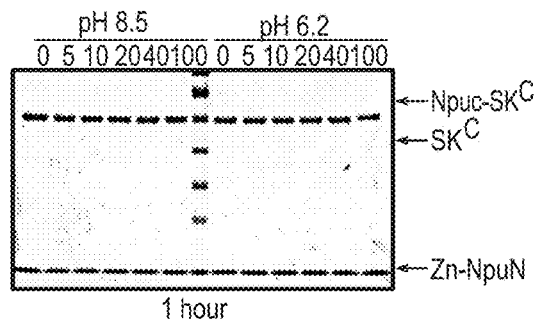
Figure 14C:
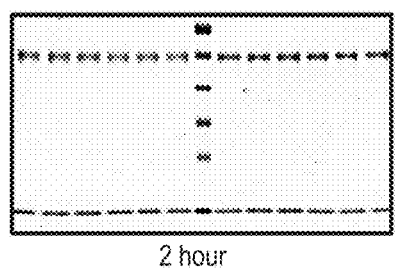
Figure 14D:
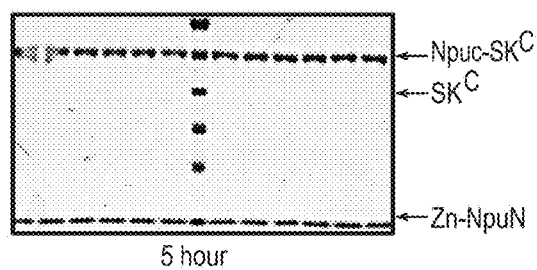
Figure 14E:
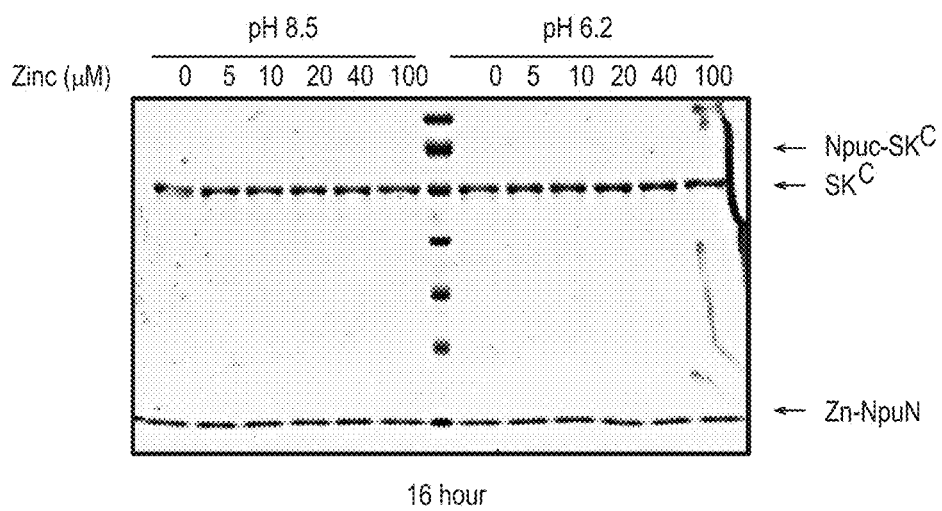
Figure 15A:
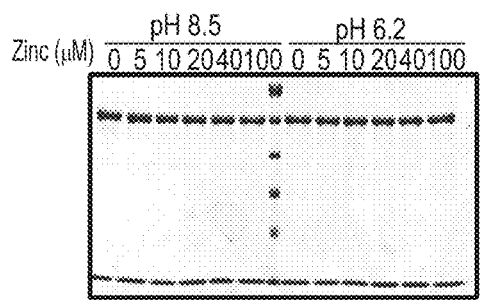
FIGS. 15A-E show the cleaving kinetics of a C-terminal intein segment with a serine to histidine mutation (Npu$_C^{HN}$) and the target protein streptokinase (SK$^M$), using an N-terminal intein segment with a sensitivity-enhancing motif (Zn-Npu$_N$), as a function of pH and zinc concentration at room temperature. The intein protein segments were expressed in *E. coli* (BLR culture), and then purified using Ni-NTA affinity chromatography. The purified Zn–Npu$_N$ and Npu$_C^{HN}$–SK$^M$ segments were then mixed in solution at a molar ratio of 2:1, respectively. Cleaving occurred at room temperature. The buffer used was 20 mM AMPD/PIPES, and 500 mM NaCl, with the pH adjusted using NaOH or HCl as needed.
Figure 15B:
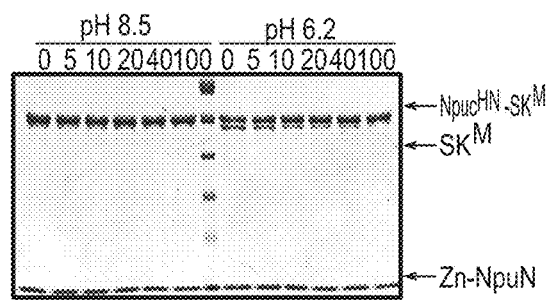
Figure 15C:
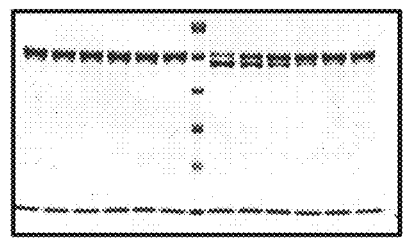
Figure 15D:
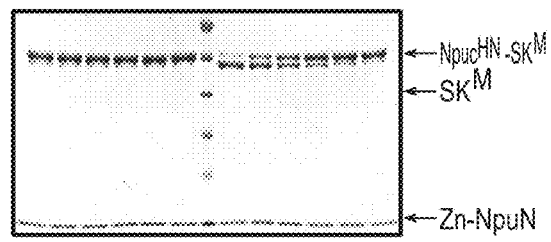
Figure 15E:
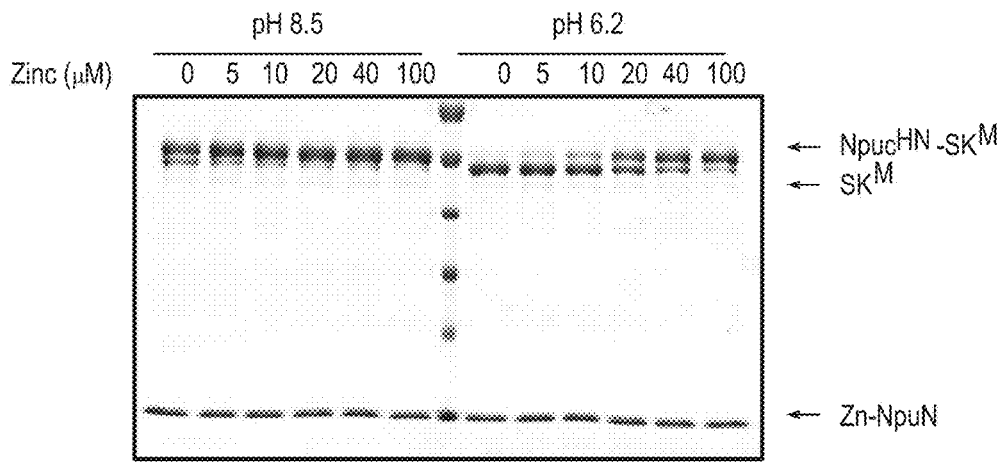
Figure 16A:
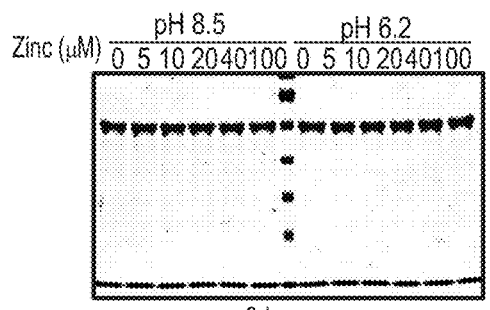
FIGS. 16A-E show the cleaving kinetics of a C-terminal intein segment with a serine to histidine mutation (Npu$_C^{HN}$) and the target protein streptokinase (SK$^C$), using an N-terminal intein segment with a sensitivity-enhancing motif (Zn-Npu$_N$), as a function of pH and zinc concentration at room temperature. The intein protein segments were expressed in *E. coli* (BLR culture), and then purified using Ni-NTA affinity chromatography. The purified Zn-Npu$_N$ and Npu$_C^{HN}$–SK$^C$ segments were then mixed in solution at a molar ratio of 2:1, respectively. Cleaving occurred at room temperature. The buffer used was 20 mM AMPD/PIPES, and 500 mM NaCl, with the pH adjusted using NaOH or HCl as needed.
Figure 16B:
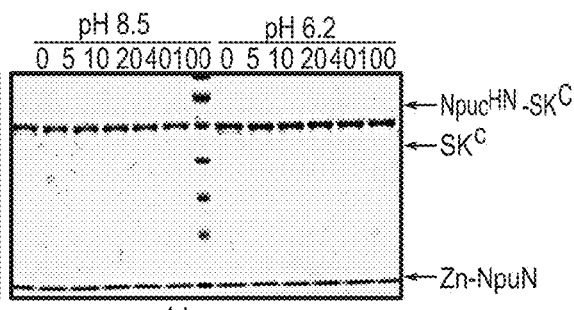
Figure 16C:
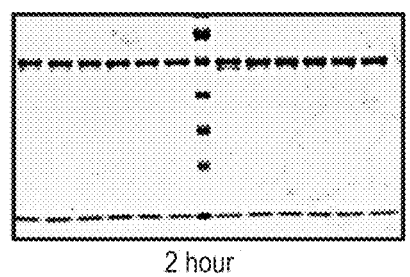
Figure 16D:
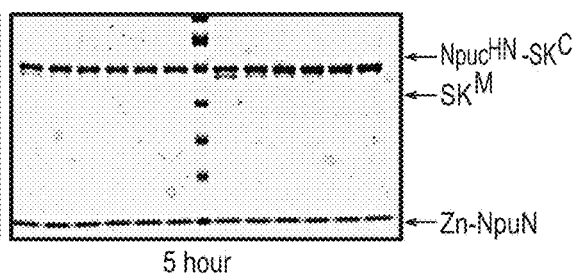
Figure 16E:
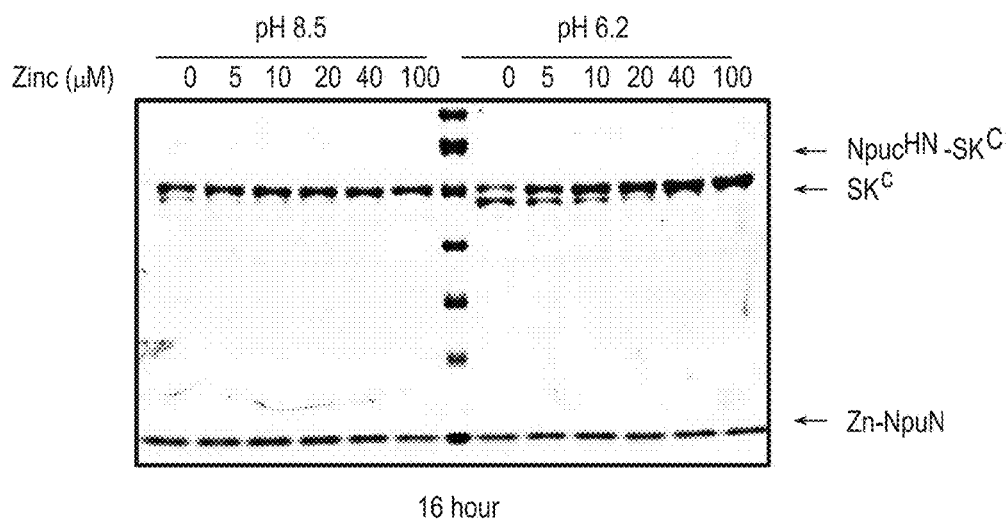
Figure 17A:
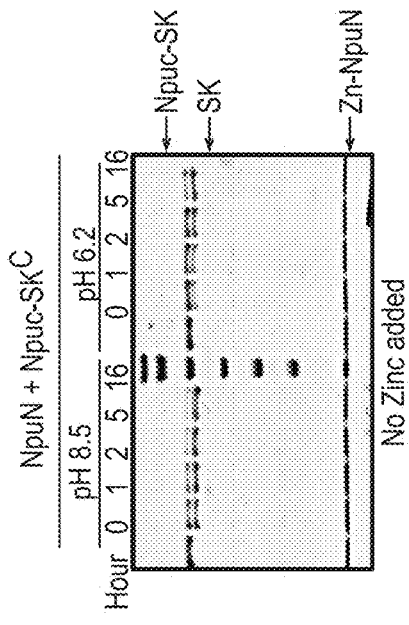
FIGS. 17A-B show cleaving kinetics of the intein segments lacking either the sensitivity-enhancing motif or the serine to histidine mutation. Specifically.
Figure 17B:
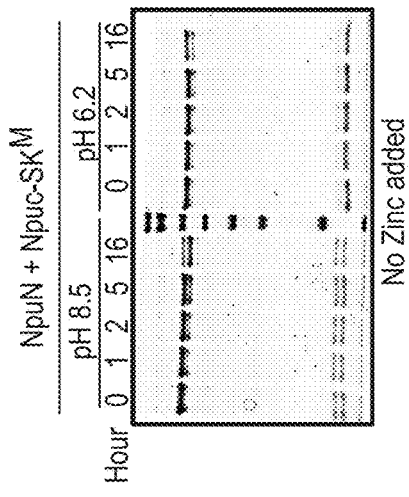
Figure 18A:
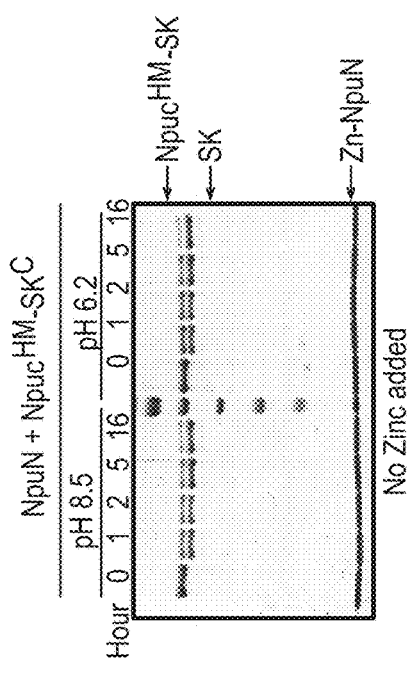
FIGS. 18A-B show cleaving kinetics of the intein segments where the Npu$_C$ intein segment has the serine to histidine mutation, but there is no sensitivity-enhancing motif on the Npu$_N$ intein segment. Specifically.
Figure 18B:
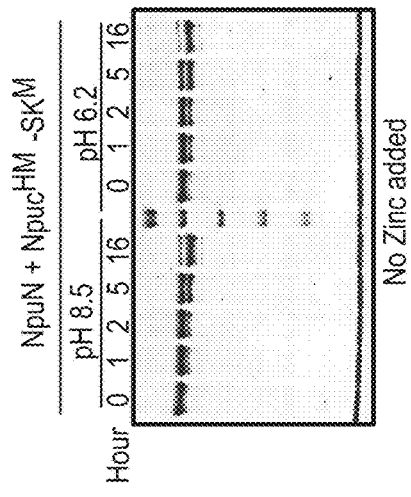
Figure 24A:
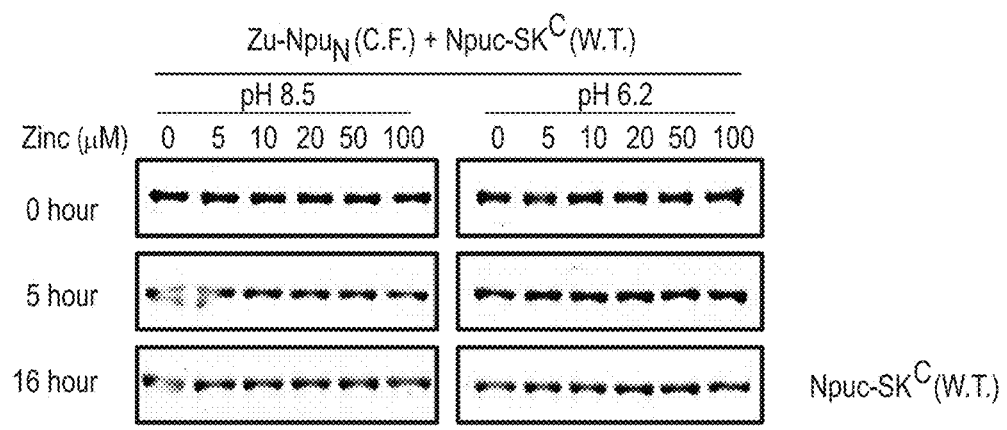
FIGS. 24A-D shows the titration of $ZnCl_2$ and the pH effect in the Npu split intein cleaving reaction. (A) The mixture of $Zn\text{-}Npu_N$ and $Npu_C$-SKC; (B) $Zn\text{-}Npu_N$ and $Npu_C^{HN}$-SKC; (C) $Zn\text{-}Npu_N$ and $Npu_C$-SKM; (D) $Zn\text{-}Npu_N$ and $Npuc^{HN}$-SKM. The cleaving reaction was carried out at room temperature over 16 hours in solution.
Figure 24B:
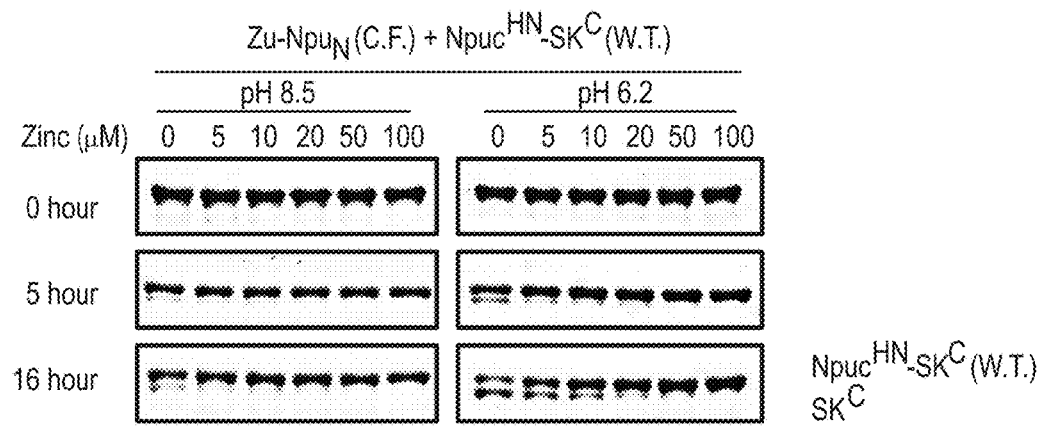
Figure 24C:
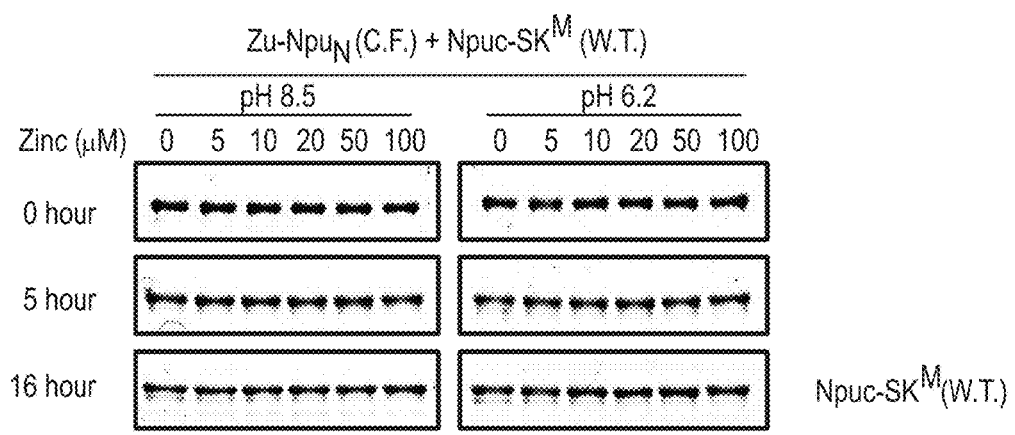
Figure 24D:
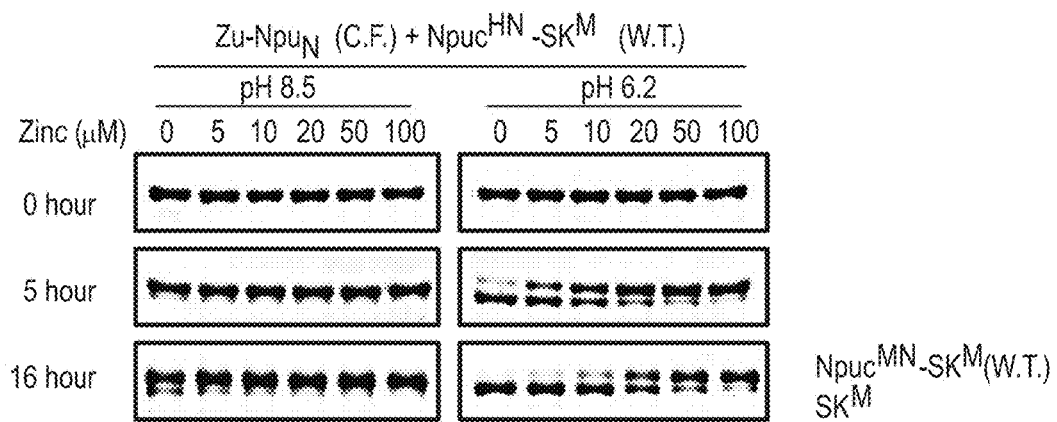

FIGS. 8-10 show the results for four recombinant proteins expressed in *E. coli* and purified using the Zn-Npu$_N$ resin. The clarified cell lysate after protein expression was diluted 5-fold in binding buffer to ensure a pH of 8.5 before loading onto the column. The binding and washing steps were carried out at pH 8.5, typically within an hour. Lane 0 hr represented the resin sample after binding and washing, showing the uncleaved, tagged target protein bound to the resin. Under the pH control, a clear band of the precursor protein could be seen while only a negligible amount of the cleaved product was observed on the gel. This indicates the successful inhibition of the cleaving reaction during the purification process. After 5 hours of cleaving reaction, the mixture of resin and the cleaved product was also collected and analyzed via SDS-PAGE. It was observed that the Npuc$^{HN}$-SK$^M$ fusion cleaved to completion within 5 hours as expected. The Npuc$^{HN}$-MBP fusion cleaved slightly slower than SK$^M$ but also showed over 80% cleavage after the pH shift to pH 6.2. Superfolder Green Fluorescent Protein (sfGFP) and β-Lactamse (β-Lac) cleaved much slower than the other two proteins, where about 50% cleavage was observed in both cases. Notably, however, in all cases a clearly purified band of target protein could be eluted from the column after each cleaving reaction.

To investigate the feasibility of using the Zn-Npu$_N$/Npuc$^{HN}$ split intein in other expression systems, the Npuc$^{HN}$-SK$^M$ and Npuc$^{HN}$-sfGFP fusion protein genes were recloned for CHO-IVT expression. To produce the tagged target proteins, 400 μL of CHO-IVT expression was carried out at 30° C. for 16 hours. The harvested expression reactions were first clarified by centrifugation and then the supernatant was transferred to the Zn-Npu$_N$ column, where 200 μL of Zn-Npu$_N$ resin was packed. The purification results were analyzed using SDS-PAGE silver staining, which is more sensitive than Coomassie stain for detecting protein bands on the gel. The results are shown in FIG. 8. Lane 0 hr represents the resin sample with the captured precursor proteins under the pH control. Cleavage took place for 5 hours after initiation with a pH shift to pH 6.2. The released target proteins were collected and analyzed in the Elution lanes. The detection of proteins by silver stain on SDS-PAGE generally allows visual observation of proteins in a single band down to nanogram levels. From the elution results, the target protein band is very clear, while no significant signals of impurities could be observed, suggesting the purity of the final products was fairly good (FIG. 27).

a. Recovery Analysis Using Streptokinase Activity Assay

A SK activity assay allowed us to quantitatively analyze how much SK target protein could be recovered after the purification process. The specific chemical conversion of plasminogen to plasmin by active Streptokinase results in a yellow end-product that can be detected by optical absorbance at 405 nm. The activity assay was validated to show that no signal would be generated by host cell proteins or any other impurities in the expression system. Consequently, the signal detected at 405 nm would only come from either the precursor protein (Npuc$^{HN}$-SK$^M$) or the cleaved product (SK$^M$).

Figure 28:
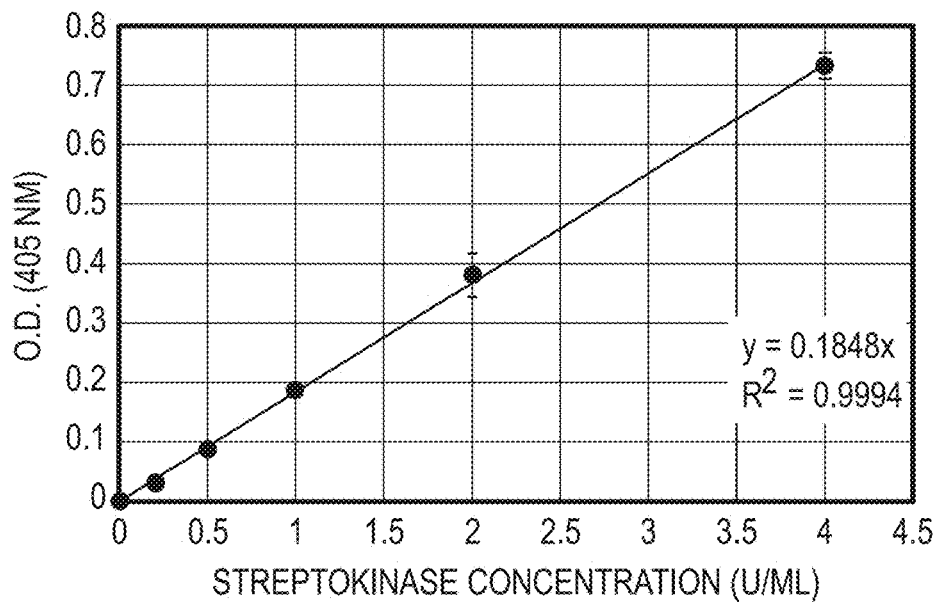
FIG. 28 shows the standard calibration curve of Streptokinase activity assay. The error bar refers to the standard deviation of three independent experiments.

A standard Streptokinase purchased from Sigma (Cat. # S3134) was first analyzed for generating the standard activity curve, as shown in FIG. 28. The slope obtained from the standard curve was then used for quantifying the expressed Streptokinase. The precursor protein (Npuc$^{HN}$-SK$^M$) harvested from the CHO-IVT mixture and the final purified product (SK$^M$) were quantified using activity assay.

The calculation of protein recovery was based on the total amount of Streptokinase in the final purified product divided by the total amount of precursor proteins in the CHO-IVT mixture:

$$\text{Protein Recovery} = \frac{\text{amount of purified SK (total Units)}}{\text{amount of expressed precursor (total Units)}}$$

Figure 29:
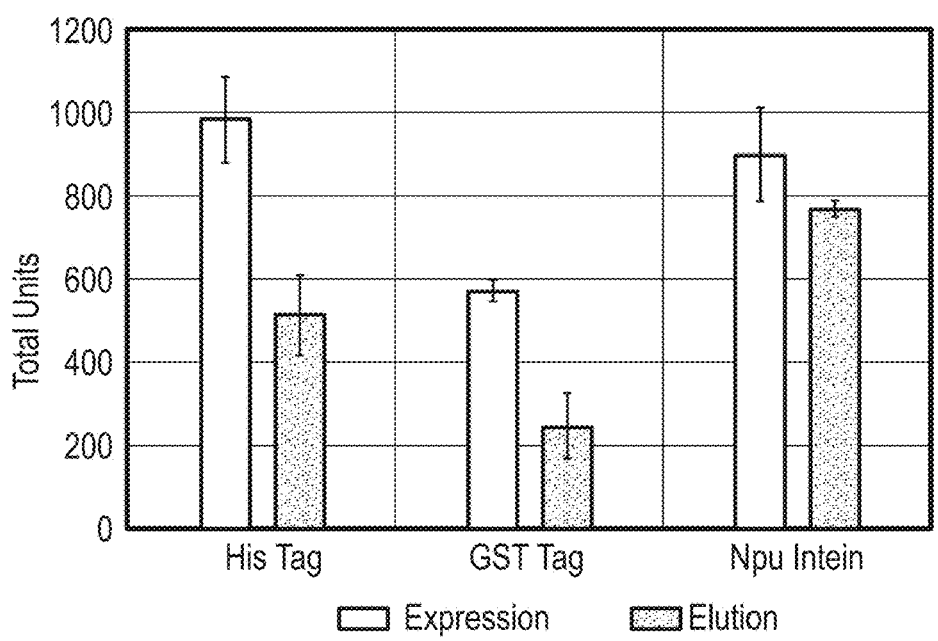
FIG. 29 shows a comparison of protein recovery using different purification schemes. The quantitative data were obtained from Streptokinase activity assay. The error bar refers to the standard deviation of three independent experiments.

For comparison, two conventional affinity tag-based purification methods, His tag and GST tag, were also examined for their protein recovery. Table 6 and FIG. 29 summarize the comparison results of the three different purification schemes. The Npu split intein purification showed a relatively high recovery among the three affinity tags. The remarkable recovery may be the result of rapid association of the split intein fragments and the effective control of cleavage.

TABLE 6

The comparison of protein recovery using different purification schemes.

| Affinity Tag | Expression (total Units) | Elution (total Units) | Recovery (%) |
|---|---|---|---|
| His tag | 988.8 ± 100.4 | 518.8 ± 95.7 | 52.5% |
| GST tag | 577.1 ± 22.7 | 248.8 ± 75.4 | 43.1% |
| Npu Intein | 904.3 ± 113.4 | 778.1 ± 16.3 | 86% |

The standard deviation was derived from three independent experiments.

4. Example 4: Recombinant Protein Purification Using Zn-Npu$_N$ Resin for Proteins Expressed in Mammalian Cell Systems The incentive of developing the split intein system for recombinant protein purification was to resolve the issue of in vivo premature cleavage, which has been particularly problematic for proteins expressed in conventional mammalian cell hosts. Given all the successful demonstrations in *E. coli* and the IVT system, the ultimate goal is to apply the Npu split intein technology to mammalian cell systems. Here the results of mammalian cell expression Npu$_C^{HN}$-tagged glycoproteins and their purification using Zn-Npu$_N$ are shown. Secreted Alkaline Phosphatase (SEAP) was selected as the target protein. This target was selected because SEAP is a disulfide-bonded glycoprotein that catalyzes the hydrolysis of p-Nitrophenyl phosphate, producing a yellow product. Thus, SEAP has many of the features of complex mammalian glycoproteins, along with a simple activity assay. The quantification of SEAP is based on the detection of the yellow end-product using a spectrophotometer at 405 nm.

The Npu$_C^{HN}$-SEAP precursor protein was transiently expressed in 50 ml of HEK293 or CHO-K1 cell culture. A signal peptide derived from immunoglobulin kappa-chain was fused to the N-terminus of the tagged SEAP protein to target the SEAP for glycosylation and secretion. Since the Npu$_C^{HN}$ split intein fragment has no splicing or cleaving activity, the possibility of in vivo premature cleavage has been completely eliminated. The clarified cell culture media with the secreted precursor proteins was harvested from the cell culture reactor, and then loaded onto the chromatographic column containing 200 μL of Zn-Npu$_N$ resin. The purification results are shown in FIG. 1. The major bands shown in the expression, flow-through and wash samples were the albumin in the fetal bovine serum (FBS), which was added at a concentration of 5% to provide required nutrients. For this reason, the main contaminant during the purification would be the albumin derived from FBS. In the 0 hr resin sample, a precursor band was observed near 72 kDa, which is about the correct size of the tagged target protein (SEAP is 68 kDa, Npuc is 4 kDa). After 5 hours of cleavage at pH 6.2, the cleaved SEAP was eluted from the column. The silver stained SDS-PAGE gel revealed that the purity of the final product was fairly decent.

Figures 31A, 31B:
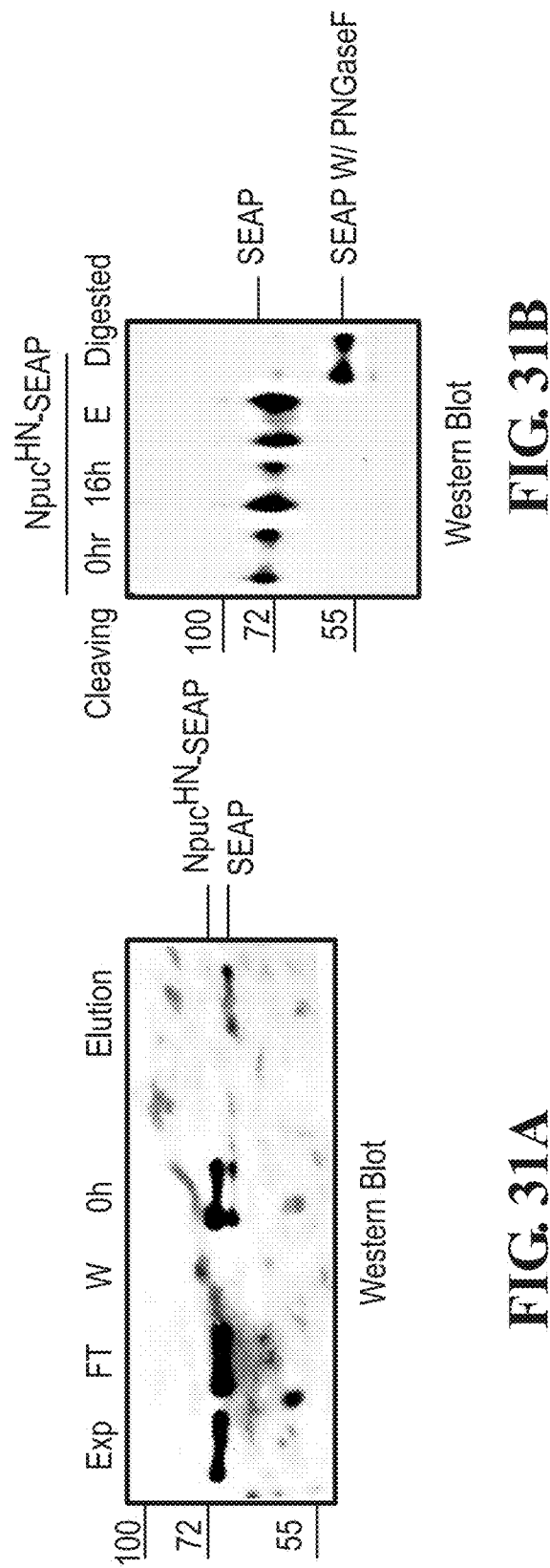
FIGS. 31A and B show the results of the purification process.

FIG. 31 is a Western Blot result to confirm the purification process. A clear band-shift between the 0 hr and the elution bands indicates the removal of the Npu$_C^{HN}$ tag. The final purified SEAP was then treated with PNGaseF to examine the glycosylation. After treating with PNGaseF, the glycans on proteins would be cleaved, resulting a band shift, as shown in FIG. 31 (B). This band shift between the elution and the digested samples suggests that the purified SEAP was glycosylated and therefore implied that the fusion with the intein tag did not affect the glycosylation pathway.

The biological activity of the purified SEAP to hydrolyze p-nitrophenyl phosphate and quantified the amount based on the colorimetric assay was also assayed.

The obtained O.D. 405 nm data was converted into the actual yield through the calibration curve that generated using standard SEAP. The yield was defined as:

$$\text{Yield} = \frac{\text{amount of purified SEAP }(\mu g)}{\text{volume of cell culture }(L)}$$

Figure 32:
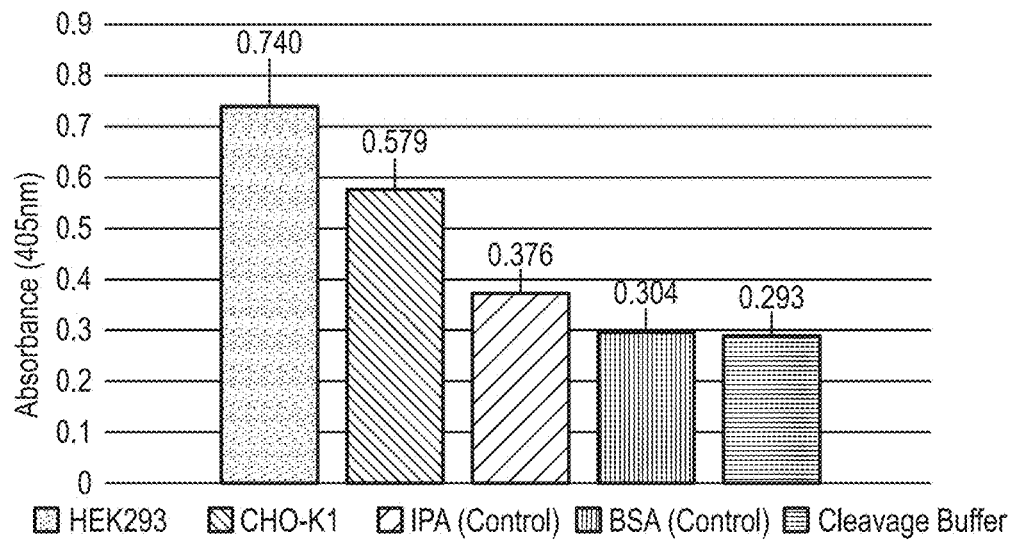
FIG. 32 shows the colorimetric assay of the purified SEAP from HEK293 and CHO-K1 cell culture. The yellow end-product was detected at O.D. 405 nm and quantified using the standard calibration curve. tPA expressed in HEK293 or CHO-K1 and a standard BSA were used as the negative control. The cleavage buffer (20 mM AMPD/PIPES, 500 mM NaCl, pH 6.2) was set as the background. The error bars referred to the standard deviation of three independent experiments.

As summarized in FIG. 32 and Table 7, the purified SEAP from both HEK293 and CHO-K1 were active, indicating the correct folding and the native protein structure was retained after intein purification.

TABLE 7

The quantified yield of the final purified SEAP from mammalian cell culture. The standard deviation referred to three independent experiments.

| Host Cell | Yield (μg/L) |
|---|---|
| HEK293 | 5.33 ± 0.40 |
| CHO-K1 | 3.39 ± 0.87 | a. Materials and Methods (a) Plasmid Construction of Npuc or NpucHN Tagged Target Proteins for Mammalian Cell Expression The Npuc or NpucHN split intein and the target protein genes were fused through overlap PCR. To enhance the tagged target protein secretion, a signal peptide derived from an immunoglobulin kappa (METDTLLLWVLLLWVPG-STGD, SEQ ID NO: 28) was engineered to the front of the tagged target protein. The Kozac sequence was also optimized for mammalian cell expression. Two unique restriction enzymes: HindIII and AfeI were designed at 5'- and 3'-end of the PCR product, respectively. The PCR-amplified precursor protein genes were digested with HindIII and AfeI and then ligated into the pTT vector for HEK293 or CHO-K1 cell transient expression.

(b) Transient Expression in Mammalian Cell System

The mammalian cell line HEK293 (ATCC® CRL-10852™) and CHO-K1 (ATCC® CCL-61™) were purchased from ATCC. The cells were cultured in Dulbecco's modified Eagle's medium (DMEM) supplemented with 4 mM L-glutamine and 10% fetal bovine serum in a T-75 tissue culture flask. The cells were incubated at 37° C. with 5% CO$_2$ in air atmosphere. For transient transfection, the plasmids were mixed with polyethylenimine (PEI) as a transfection vector at a 1:3 ratio (w/w). The DNA-PEI mixture was incubated at room temperature for 30 minutes and then sterilized through a 0.22 μm syringe filter. In general, 1 μg of plasmid DNA per 1 ml of culture was transfected when the cell confluency was in the range of 40 to 60%. The sterile DNA-PEI mixture was gently added to the cell culture media without shaking. The expressed protein was then harvested 3 days after transfection.

(c) A General Protocol for Recombinant Protein Purification Using Npu$_N$-Coupled Resin To purify the Npuc or Npu$^{HN}$-tagged proteins, 200 μL (bed volume) of the Npu$_N$-coupled SulfoLink resin was packed into a chromatographic column and equilibrated with 10 column-volume of binding buffer (20 mM AMPD/PIPES, 500 mM NaCl, pH 8.5). The expressed protein mixtures (or lysates in the cases of E. coli expression) were first diluted 5-fold in binding buffer and clarified by centrifugation at 10,000 g, 4° C. for 2 minutes. The collected supernatant was loaded onto the NpuN column for binding and then washed with at least 10 column-volumes of wash buffer (20 mM AMPD/PIPES, 500 mM NaCl, pH 8.5) to thoroughly remove the impurities. The C-terminal cleaving reaction was induced by adding one column-volume of cleavage buffer (20 mM AMPD/PIPES, 500 mM NaCl, pH 6.2) and sealed for 5 hours at room temperature. The final cleaved product was then eluted from the column. To regenerate the Npu$_N$-coupled SulfoLink resin, 0.1M NaOH, 0.5% Triton X100 and 2 mM ZnCl$_2$ was added to denature the split intein assembly at 40° C. for at least 40 minutes.

(d) Streptokinase Activity Assay

The activity assay of Streptokinase is based on the potency of converting plasminogen to plasmin. Plasminogen activation by streptokinase can be quantitatively assayed using the synthetic chromogenic substrate S-2251™ (Chromogenix cat. no. 820332). The SK-converted plasmin accelerates the hydrolysis of S-2251, resulting in the formation of a yellow end-product that can be detected at an optical absorbance of 405 nm. The native Glu-Plasminogen was purchased from ThermoFisher (Catalog#: RP-43078). Substrate S-2251 was used for testing the amount of SK-converted plasmin in the reaction. To perform the assay, the SK samples were diluted in sample buffer (5 mL Tris-HCl pH 7.4 (from 0.5M stock) 25 μL NaCl (from 1M stock) 250 mg BSA (Sigma cat. no. A3311) filtered diH$_2$O to 50 mL) to a desired dilution for the assay. To assay in a 96-well plate format, 60 μL of diluted SK sample was mixed with 45 μL of glu-plasminogen, and 40 μL of substrate solution (1 mL 0.5M Tris-HCl pH 7.4 1 mL 3 mM S-2251 5 μL 10% Tween 20), mixed thoroughly. The plate was then incubated at 37° C. for one hour and then read the absorbance at 405 nm.

Figure 33:
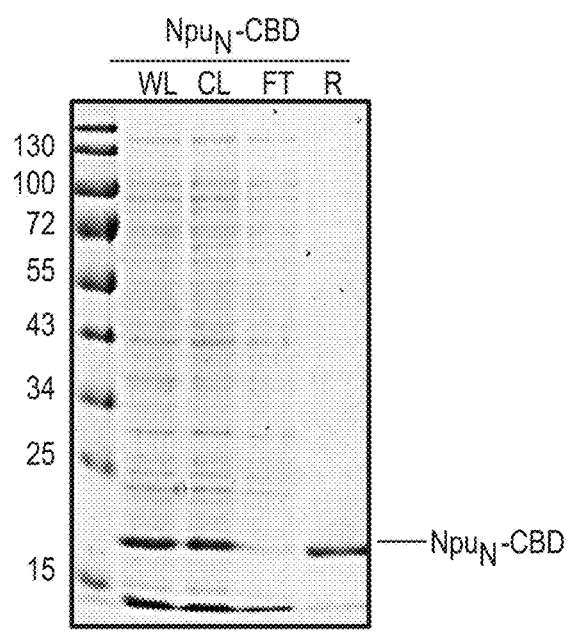
FIG. 33 shows the immobilization of $Npu_N$-CBD onto a chitin resin. Lane WL: whole cell lysate; Lane CL: clarified lysate; Lane FT: the flow-through sample from the chitin column; Lane R: the resin sample of the pure immobilized $Npu_N$-CBD Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

5. Example 5: A Npu Split Intein-Mediated Recombinant Protein Purification Using a Conventional Affinity Tag Immobilization Method The Npu$_N$ intein segment is fused at its C-terminus to a conventional affinity tag, in this case a chitin binding domain (CBD), to demonstrate a chromatographic purification method. The Npu$_N$-CBD was expressed in E. coli and then purified directly from the E. coli cell lysate using CBD tag. After removing the impurities, the Npu$_N$-CBD bound to the chitin resin effectively forms an Npu$_N$-conjugated resin, as shown in FIG. 33. This Npu$_N$-conjugated resin was then used for capturing the Npuc-tagged target through split intein segment (Npu$_N$ and Npu$_C$) association.

Figure 6:
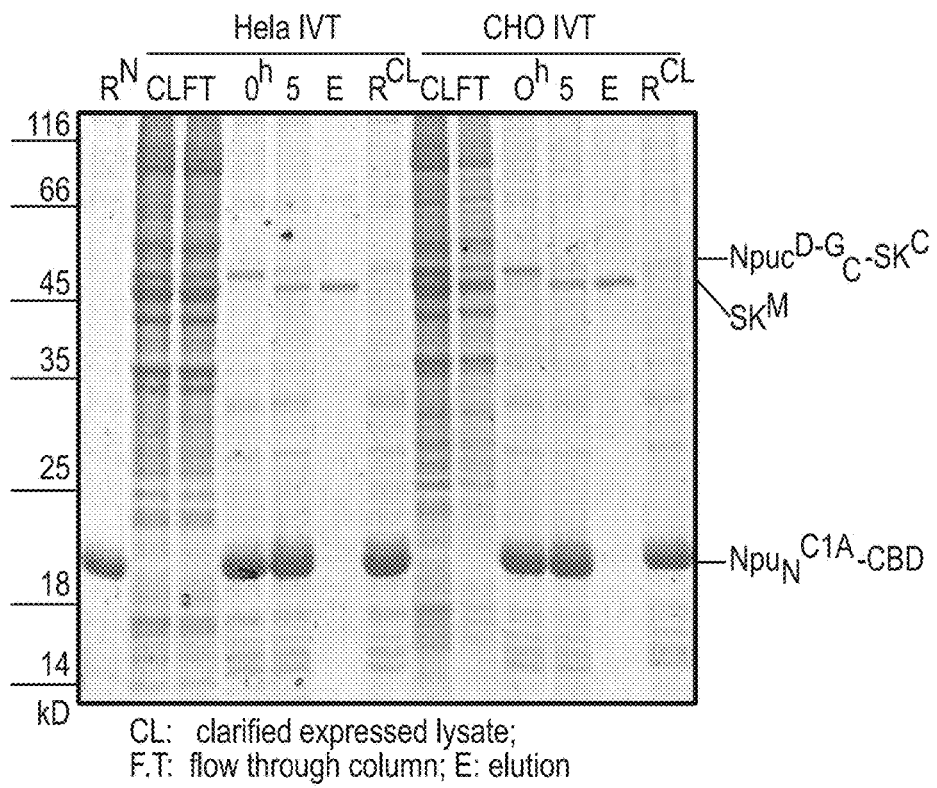
FIG. 6 shows the purification of the streptokinase (SK) test protein using the CBD affinity tag method with the split intein and IVT expression system described above. Expression products (CL=clarified lysate; FT=flow through), resin samples ($0^h$=bound purified proteins at zero hours incubation; 5=proteins in the column at 5 hours incubation) and purified protein (E=eluted protein) were examined via Coomassie stained SDS-PAGE. In this case, the intein cleaving reaction was carried out by incubation for 5 hours at 37° C. in the absence of DTT. Lane R is the proteins recovered from the column during regeneration by SDS. These data represent the purification of tagless SK (without a His-tag) directly from the IVT translation mixture, showing the relatively high purity of the cleaved SK target protein and near complete cleaving of the intein tag over 5 hours at 37° C.

To demonstrate the actual application of this chromatographic purification scheme, the Npuc-SK precursor protein was expressed in a separate IVT (In vitro translation) system. Two IVT lysates were used here; the HeLa-IVT and CHO-IVT, resulting from lysis or HeLa and CHO cells, respectively; and both of which have been evaluated for synthesizing therapeutic proteins, including monoclonal antibodies. A total of 200 μL of Npu$_N$-conjugated resin was packed in a chromatographic column and equilibrated with 20 column-volumes of binding buffer (20 mM AMPD/PIPES, 500 mM NaCl, pH 8.5). FIG. 6 presents the actual purification procedure. After binding and washing, Lane 0 hr showed a clear band of the captured Npu-SK precursor, representing the assembly of the $Npu_N$-CBD and Npuc-SK. The cleaving reaction was carried out at room temperature for 5 hours in the absence of DTT. The final eluted Streptokinase showed a fairly decent purity, indicating the high selectivity of using this split intein system. Further, the C-terminal cleaving reaction went to nearly completion within the given time span.

A. Materials and Methods:

(a) Plasmid Construction with Naturally Occurring Split Intein (Npu DNAe)

The Npuc split intein segment and the streptokinase (SK) genes were fused using overlapping PCR. Two unique restriction enzymes: NdeI and XhoI were designed at the 5'- and 3'-ends of the PCR product, respectively. The PCR-amplified genes ($Npu_C$-SK) were digested with NdeI and XhoI and ligated into the pET or pT7CFE1-CHis vectors for E. coli or CHO-IVT expression. The $Npu_N$-CBD fusion was created using overlapping PCR with unique restriction enzyme sites: NdeI and XhoI at the 5'- and 3'-end, respectively. The resulting PCR product was then digested with NdeI and XhoI and cloned into a pET vector for E. coli. Expression. Table 8 lists the primers used for making the split intein fusion proteins.

TABLE 8

The primers used in making split itein-mediated clones (C. H. Shi et al., 2013)

| Primers | Sequence (5' - 3') |
|---|---|
| NpuN-forward | 5'-GGCCATATGATGGCCTTAAGCTATGAAACGGAAAT-3' (SEQ ID NO: 29) |
| NpuN-CBD-overlap-F | 5'-GATAATTTGCCGAATGGTGGAGGAGGATCTGGGGGT GGTGGTTCTATGACGACAAATCCTGGTGTATC-3' (SEQ ID NO: 30) |
| NpuN-CBD-overlap-R | 5'-AGGATTTGTCGTCATAGAACCACCACCCCCAGATCC TCCTCCACCATTCGGCAAATTATCAACCCGCAT-3' (SEQ ID NO: 31) |
| NpuN-reverse | 5'-GGCCTCGAGTGCGGCCGCAAGCTTTTA-3' (SEQ ID NO: 32) |
| Npuc-SK-forward | 5'-GGCCATATGCATCATCATCATCACATCAAAATAG CCACACGTAAATA-3' (SEQ ID NO: 33) |
| Npuc-SK-reverse | 5'-GTGGTGGTGCTCGAGTCATTATTTGTCATTGGGATT GTCGGG-3' (SEQ ID NO: 34) |

(b) Immobilization of Chitin Binding Domain Tagged-$Npu_N$ ($Npu_N$-CBD)

The $Npu_N$-CBD genes were expressed in *Escherichia coli* strain BLR(DE3) (F-ompT hsdSB(rB-,mB-) gal dcm (DE3)), following typical procedures. The harvested cell lysate solutions were clarified by centrifugation at 6000 g, 4° C. for 10 min. For immobilization, the collected supernatants were loaded onto a chromatography column packed with 1 ml of equilibrated chitin-agarose resin (NEB, Cat. # S6651S). The CBD-tagged $Npu_N$ binds to the chitin resin through the affinity tag. The column was washed with 20 column-volumes of wash buffer (20 mM AMPD/PIPES, 500 mM NaCl, pH 8.5) to completely remove the impurities. Lastly, the $Npu_N$-CBD-coupled resin was stored in 20% ethanol at 4° C. for future use.

(c) Recombinant Protein Expression in In Vitro Translation (IVT) Systems

The HeLa-IVT or CHO-IVT system was purchased from Thermo Fisher Scientific (CHO Lysate, Accessory Proteins, 5× Reaction Mix, 4× Dialysis Buffer, Cat. #88894). To express proteins in a 100 μL reaction, the materials are mixed in the following order: Lysate 50 μL, Accessory Proteins 10 μL, 5× Reaction Mix 20 μL. The plasmids constructed with the precursor protein genes as described previously were added to the mixture to a total amount of 4 μg DNA. The whole reaction mixture was then transfered to a micro-dialysis tube (Thermo, Cat. #88891Y) and immersed into a 2 ml micro-centrifuge tube supplied with 1400 μL of dialysis buffer. The mixture was incubated at 30° C. for 16 hours to allow expression of the tagged target protein.

(d) Protein Purification Using Split Intein ($Npu_N$-CBD)-Coupled Resin

To purify the Npuc-tagged SK target proteins, 200 μL of the $Npu_N$-CBD-coupled resin was packed into a gravity column, and equilibrated with 20 column-volumes of wash buffer (20 mM AMPD/PIPES, 500 mM NaCl, pH 8.5). IVT reactions with expressed proteins were first diluted in 5 volumes of wash buffer and then clarified by centrifugation at 10,000 g, 4° C. for 2 minutes. The collected supernatant was loaded onto the $Npu_N$-CBD column and then washed with 20 column-volumes of wash buffer. After thoroughly washing out the impurities, one column-volume of elution buffer (20 mM AMPD/PIPES, 500 mM NaCl, pH 8.5) was added to the column and the column was sealed for 5 hours and incubated at 37° C. to allow cleavage.

6. Example 6: Sensitivity Enhancing Motifs

Intein modification summary: the −1 residue is the first amino acid before the intein, while the +1 amino acid is formally the first amino acid of the intein. The zinc binding motifs include the amino acids before the intein, occasionally along with the first amino acid of the intein.

TABLE 9

Extein/Intein Controlling Ability

| Extein/Intein | −1 | +1 | Controlling Ability |
|---|---|---|---|
| LN001 | GEGH (SEQ ID NO: 24) | HLAEGTRI (SEQ ID NO: 25) | + |
| LN002 | GEGH (SEQ ID NO: 24) | CLAEGTRI (SEQ ID NO: 26) | Cannot get the precursors in E. coli |
| LN003 | GEGHH (SEQ ID NO: 14) | ALAEGTRI (SEQ ID NO: 27) | ++ |
| LN003b | GDGHH (SEQ ID NO: 16) | ALAEGTRI (SEQ ID NO: 27) | ++++ |
| LN004 | GEGHG (SEQ ID NO: 15) | CLAEGTRI (SEQ ID NO: 26) | +++ |
| LN004b | GDGHG (SEQ ID NO: 17) | CLAEGTRI (SEQ ID NO: 26) | ++++ |

DNA sequences (modifications, including the +1 amino acid are underlined):

```
01: GGAGAGGGACATCACCTCGCAGAGGGCACTCGGAT        (SEQ ID NO: 18)

02: GGAGAGGGACATTGCCTCGCAGAGGGCACTCGGAT        (SEQ ID NO: 19)

03: GGAGAGGGACATCATGCCCTCGCAGAGGGCACTCG        (SEQ ID NO: 20)

04: GGAGAGGGACATGGATGCCTCGCAGAGGGCACTCGG       (SEQ ID NO: 21)

3b: GGAGATGGACATCATGCCCTCGCAGAGGGCACTCGGA      (SEQ ID NO: 22)

4b: GGAGATGGACATGGATGCCTCGCAGAGGGCACTCGGA      (SEQ ID NO: 23)
```

Table 10 shows $EC_{50}$ values for the modifications:

|  | CM | LN003 | LN004 | LN003b | LN004b |
|---|---|---|---|---|---|
| $EC_{50}$ (µM) | 100.49 | 107.23 | 52.13 | 23.21 | 17.30 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

7. REFERENCES

Iwai H, Zuger S, Jin J, Tam P H (2006) Highly efficient protein trans-splicing by a naturally split DnaE intein from Nostoc punctiforme. Febs Letters 580: 1853-1858.

Mootz H D, Dhar T (2011) Modification of transmembrane and GPI-anchored proteins on living cells by efficient protein trans-splicing using the Npu DnaE intein. Chemical Communications 47: 3063-3065.

Ramirez M, Valdes N, Guan D, Chen Z (2013) Engineering split intein DnaE from Nostoc punctiforme for rapid protein purification. Protein Eng Des Sel 26: 215-223.

Guan D, Ramirez M, Chen Z (2013) Split intein mediated ultra-rapid purification of tagless protein (SIRP). Biotechnol Bioeng 110: 2471-2481.

Wood D W, Wu W, Belfort G, Derbyshire V, Belfort M (1999) A genetic system yields self-cleaving inteins for bioseparations. Nature Biotechnology 17: 889-892.

Shi C, Tarimala A, Meng Q, Wood D W (2014) A general purification platform for toxic proteins based on intein trans-splicing. Appl Microbiol Biotechnol 98: 9425-9435.

Vila-Perello M, Liu Z, Shah N H, Willis J A, Idoyaga J, et al. (2013) Streamlined expressed protein ligation using split inteins. J Am Chem Soc 135: 286-292.

Perler, F. B., et al., (1994) Nucleic Acids Res 22, 1125-1127

Perler, F. B. (2002) Nucleic Acids Res 30, 383-384. [19]

Saleh, L., et al. (2006) Chem Rec 6, 183-193.

Liu, X. Q., et al. (2003) J Biol Chem 278, 26315-26318

Yang, J., et al. (2004) Mol Microbiol 51, 1185-1192.

Telenti, A., et al. (1997) J Bacteriol 179, 6378-6382.

Wu, H., Xu, M. Q., et al. (1998) Biochim Biophys Acta 1387, 422-432.

Derbyshire, V., et al. (1997) Proc Natl Acad Sci USA 94, 11466-11471.

Duan, X., et al. (1997) Cell 89, 555-564.

Ichiyanagi, K., et al. (2000) J Mol Biol 300, 889-901.

Klabunde, T., et al. (1998) Nat Struct Biol 5, 31-36.

Ding, Y., et al. (2003) J Biol Chem 278, 39133-39142. [29]

Xu, M. Q., et al. (1996) Embo J 15, 5146-5153.

Scott, C. P., et al. (1999) Proc Natl Acad Sci U.S.A. 96, 13638-13643.

Xu, M. Q., et al., (2001) Methods 24, 257-277.

Evans, T. Cl Jr., et al. (2000) J Biol Chem 275, 9091-9094.

Kwon, Y. et al., (2006) Angew Chem Int Ed 45, 1726-1729

---

What is claimed is:

1. A protein purification system, wherein the system comprises a split intein comprising two separate peptides: an N-terminal intein segment and a C-terminal intein segment, wherein the N-terminal intein segment comprises one or more amino acids at its C-terminus which allows for covalent immobilization of the N-terminal intein segment to a solid support, and wherein cleaving of the C-terminal intein segment is more sensitive to extrinsic conditions compared to a native intein, wherein a protein of interest (POI) is attached to the C-terminal intein segment at its C-terminus.

2. The protein purification system of claim 1, wherein the split intein has been derived from a native intein.

3. The protein purification system of claim 2, wherein the intein is derived from an Npu DnaE intein.

4. The protein purification system of claim 2, wherein the N-terminal intein segment has been modified so as not to comprise any internal cysteine residues.

5. The protein purification system of claim 4, wherein at least one of the internal cysteine residues have been mutated to serine residues.

6. The protein purification system of claim 1, wherein a purification tag is attached to the N-terminal intein segment at its C-terminus.

7. The protein purification system of claim 6, wherein the purification tag comprises one or more histidine residues.

8. The protein purification system of claim 1, wherein the amino acids at the C-terminus are cysteine residues.

9. The protein purification system of claim 1, wherein the N-terminal intein segment is immobilized on a solid chromatographic resin backbone.

10. The protein purification system of claim 1, wherein the N-terminal intein segment further comprises a sensitivity-enhancing motif, which renders it more sensitive to extrinsic conditions.

11. The protein purification system of claim 10, wherein the sensitivity-enhancing motif is on the N-terminus of the N-terminal intein segment.

12. The protein purification system of claim 10, wherein the extrinsic condition is pH, temperature, or both.

13. The protein purification system of claim 1, wherein the N-terminal intein segment comprises SEQ ID NO: 2.

14. The protein purification system of claim 1, wherein the N-terminal intein segment comprises SEQ ID NO: 3.

15. The protein purification system of claim 1, wherein the N-terminal intein segment comprises SEQ ID NO: 4.

16. The protein purification system of claim 1, wherein the N-terminal intein segment comprises SEQ ID NO: 5.

17. The protein purification system of claim 1, wherein the N-terminal intein segment comprises SEQ ID NO: 6.

18. The protein purification system of claim 1, wherein the C-terminal intein segment comprises SEQ ID NO: 9.

19. A method of purifying a protein of interest, the method comprising:
   a. utilizing a split intein comprising two separate peptides: an N-terminal intein segment and a C-terminal intein segment;
   b. covalently immobilizing the N-terminal intein segment to a solid support;
   c. attaching a protein of interest to the C-terminal intein segment, wherein cleaving of the C-terminal intein segment is more sensitive to extrinsic conditions compared to a native intein;
   d. exposing the N-terminal intein segment and the C-terminal intein segment to each other so that they associate;
   e. washing the solid support to remove non-bound material;
   f. placing the associated the N-terminal intein segment and the C-terminal intein segment under conditions that allow for the intein to self-cleave;
   g. isolating the protein of interest.

* * * * *